(12) United States Patent
Fritsch et al.

(10) Patent No.: US 7,169,272 B2
(45) Date of Patent: Jan. 30, 2007

(54) MICROFABRICATED RECESSED DISK MICROELECTRODES: CHARACTERIZATION IN STATIC AND CONVECTIVE SOLUTIONS

(75) Inventors: Ingrid Fritsch, Fayetteville, AR (US); Charles Sherman Henry, Starkville, MS (US); Benjamin P. Bowen, Tempe, AZ (US); Walter Vandaveer, Lawrence, KS (US); Nicole Bratcher, Pittsburg, OK (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 434 days.

(21) Appl. No.: 10/104,756

(22) Filed: Mar. 22, 2002

(65) Prior Publication Data

US 2003/0015422 A1    Jan. 23, 2003

Related U.S. Application Data

(63) Continuation-in-part of application No. 09/946,259, filed on Sep. 4, 2001, now abandoned, which is a continuation-in-part of application No. 09/775,937, filed on Feb. 2, 2001, now abandoned, which is a continuation-in-part of application No. 09/255,950, filed on Feb. 23, 1999, now abandoned, which is a continuation-in-part of application No. 09/071,356, filed on Apr. 30, 1997, now abandoned.

(60) Provisional application No. 60/075,955, filed on Feb. 23, 1998, provisional application No. 60/042,100, filed on Apr. 30, 1997.

(51) Int. Cl.
*G01N 27/327* (2006.01)
*C12N 11/00* (2006.01)

(52) U.S. Cl. .................... 204/403.01; 204/403.07; 435/174

(58) Field of Classification Search ............ 204/ 403.9–403.14; 435/174
See application file for complete search history.

(56) References Cited

U.S. PATENT DOCUMENTS

| 4,779,031 A | 10/1988 | Arends et al. ............ 318/565 |
| 4,891,242 A | 1/1990 | Ito et al. ................... 427/53.1 |
| 4,961,806 A | 10/1990 | Gerrie et al. ............... 156/252 |

(Continued)

FOREIGN PATENT DOCUMENTS

WO    WO 90/12314 A1 * 10/1990

(Continued)

OTHER PUBLICATIONS

English language translation of Urban et al. (WO 90/12314 A1).*

(Continued)

*Primary Examiner*—Alex Noguerola
(74) *Attorney, Agent, or Firm*—Head, Johnson & Kachigian

(57) ABSTRACT

Construction and characterization of microfabricated recessed disk microelectrodes (RDMs) of 14 and 55 μm diameter are reported. The work reported here makes several new contributions to the current literature on microfabricated RDMs. Hybrid blamers were constructed by fusion of vesicles of dimyristoylphosphatidyl choline (DMPC), which forms the top layer, with ethanol-rinsed SAMs of hexadecanethiol on gold, which form the bottom layer. Gramicidin A was included in the modifying solutions to incorporate it into hybrid blamers.

3 Claims, 28 Drawing Sheets

U.S. PATENT DOCUMENTS

| | | | | |
|---|---|---|---|---|
| 4,972,470 | A | 11/1990 | Farago | 380/3 |
| 5,053,920 | A | 10/1991 | Staffiere et al. | 361/383 |
| 5,159,427 | A | 10/1992 | Ogura et al. | 357/48 |
| 5,204,239 | A * | 4/1993 | Gitler et al. | 435/7.1 |
| 5,253,156 | A | 10/1993 | Sakurai et al. | 363/98 |
| 5,313,150 | A | 5/1994 | Arakawa et al. | 318/768 |
| 5,355,301 | A | 10/1994 | Saito et al. | 363/147 |
| 5,365,405 | A | 11/1994 | Hoenlein et al. | 361/766 |
| 5,384,691 | A | 1/1995 | Neugebauer et al. | 361/794 |
| 5,410,107 | A | 4/1995 | Schaper | 174/255 |
| 5,412,558 | A | 5/1995 | Sakurai et al. | 363/98 |
| 5,432,675 | A | 7/1995 | Sorimachi et al. | 361/719 |
| 5,434,745 | A | 7/1995 | Shokrgozar et al. | 361/735 |
| 5,452,182 | A | 9/1995 | Eichelberger et al. | 361/749 |
| 5,488,542 | A | 1/1996 | Ito | 361/793 |
| 5,495,394 | A | 2/1996 | Kornfeld et al. | 361/764 |
| 5,516,890 | A * | 5/1996 | Tomich et al. | 530/326 |
| 5,532,512 | A | 7/1996 | Fillion et al. | 257/686 |
| 5,544,017 | A | 8/1996 | Beilin et al. | 361/790 |
| 5,604,383 | A | 2/1997 | Matsuzaki | 257/778 |
| 5,608,192 | A | 3/1997 | Moriizumi et al. | 174/255 |
| 5,608,617 | A | 3/1997 | Morrison et al. | 363/147 |
| 5,616,888 | A | 4/1997 | McLaughlin et al. | 174/260 |
| 5,619,108 | A | 4/1997 | Komurasaki et al. | 318/140 |
| 5,629,559 | A | 5/1997 | Miyahara | 257/666 |
| 5,629,574 | A | 5/1997 | Cognetti et al. | 310/71 |
| 5,634,267 | A | 6/1997 | Farnworth et al. | 29/840 |
| 5,641,944 | A | 6/1997 | Wieloch et al. | 174/252 |
| 5,756,355 | A * | 5/1998 | Lang et al. | 435/7.21 |

FOREIGN PATENT DOCUMENTS

WO    WO 94/25862 A1 * 11/1994

OTHER PUBLICATIONS

Plant ("self-Assembled Phospholipid /Alkanethiol Biomimetic Bilayers on Gold," Langmuir 1993, 9, 2764-2767).*

Hennestahl et al. (Pore-Spanning Lipid Bilayers Visualized by Scanning Force Microscopy, J. Am. Chem. Soc. 2000, 122, 8085-8086) Web release date Aug. 8, 2000.*

*Stock Product Catalog 501, Baldor Motors and Drives, Jan. 1, 1997.

*The Animatics SmartMotor, Animatics Corporation, Santa Clara, CA.

*Kaplan, Gadi, Senior Technical Editor, Industrial Electronics, IEEE Spectrum, Jan., 1998, Technology 1998 Analysis & Forecast, pp. 73-78.

*Burgers, K.C., Olejniczak, J.K., Ang, S.S., Porter, E., The Use of Multichip Module Technology for Power Electronics Miniaturization and Packaging, Dept. of Electrical Engineering and High Density Electronics Center, University of Arkansas, Fayetteville, AR, IEEE, 1997, pp. 35-41.

*Clark, Rose A., Hietpas, Paula Beyer, Ewing, Andrew G., Electrochemical Analysis in Picoliter Microvials, Analytical Chemistry, vol. 69, No. 2, Jan. 15, 1997, pp. 259-263.

Osborn, Thor D., Yager, Paul, Formation of Planar Solvent-Free Phopholipid Bilayers by Langmuir—Blodgett Transfer of Monolayers to Micromachined Apertures in Silicon, Langmuir, vol. 11, No. 1, 1995, pp. 8-12.

*Ha, Joomi, Henry, Charles S., Fritsch, Ingrid, Methods for Assembling Biological Molecules Within Lipid Environments Onto Electrodes, Electrochemical Society Proceedings vol. 96-9, pp. 197-211.

*Bond, Alan M., Luscombe, Darryl, Oldham, Keith B., Zoski, Cynthia G., A Comparison of the Chronoamperometric Response at Inlaid and Recessed Disc Microelectrodes, J. Electroanal. Chem., 249 (1988) 15-24.

*Niwa, Osamu, Morita, Masao, Tabei, Hisao, Fabrication and Characteristics of Vertically Separated Interdigitated Array Electrodes, J. Electroanal. Chem., 267 (1989) 291-297.

* cited by examiner

MICROFABRICATED RECESSED DISK MICROELECTRODES: CHARACTERIZATION IN STATIC AND CONVECTIVE SOLUTIONS

CROSS-REFERENCE TO RELATED APPLICATIONS

This application is a continuation-in-part of U.S. patent application Ser. No. 09/946,259, abandoned, filed on Sep. 4, 2001, which is a continuation-in-part of U.S. patent application Ser. No. 09/775,937, abandoned, filed Feb. 2, 2001, which is a continuation-in-part of U.S. patent application Ser. No. 09/255,950, abandoned, filed Feb. 23, 1999, which claims priority to U.S. provisional application Ser. No. 60/075,955, filed Feb. 23, 1998. This application claims priority to U.S. provisional application Ser. No. 60/055,527, filed Aug. 8, 1997. This application is also a continuation-in-part to U.S. patent application Ser. No. 09/071,356, abandoned, filed Apr. 30, 1998, which claims priority to U.S. provisional application Ser. No. 60/042,100, filed Apr. 30, 1997. Each of these applications are hereby incorporated by reference.

STATEMENT REGARDING FEDERALLY SPONSORED RESEARCH OR DEVELOPMENT

Not applicable.

REFERENCE TO A SEQUENCE LISTING, A TABLE OR A COMPUTER PROGRAM LISTING COMPACT DISC

Not applicable.

BACKGROUND OF THE INVENTION

1. Field of the Invention.

The present invention relates to microfabricated recessed disk microelectrodes. More specifically, this invention relates to microcavities containing microelectrodes and being separated from surrounding media by a lipid bilayer that is anchored to the rim of the microcavity. The invention also relates to microcavities having a hole in the bottom in order to relieve osmotic pressure. The invention also relates to arrays of such microcavities.

2. Prior Art

Microelectrode based electrochemical analysis systems are advantageous over systems containing macroelectrodes. First, microelectrodes can be made very small, for example bands with widths 32 nm and single microdisks with diameters of 2 nm. Second, the current density for microelectrodes is greater than that at macroelectrodes due to radial diffusion. This results in a measurable steady state current at electrodes of the dimensions described above. Finally, uncompensated resistance does not induce large potential drops due to the small currents drawn by micro electrodes.

Microelectrodes have been used for analysis in small volumes. Two general approaches have been used for the analysis, differentiated by the construction of the system. The first type of system uses single electrodes placed in solution. The second type of system uses microfabrication techniques to pattern the electrodes. The smallest volumes, 0.6 nL, using this technique have been demonstrated.

Microelectrodes have been used for analysis in convective systems. One example of this is the use of microelectrodes as detectors in liquid chromatography and capillary electrophoresis. The baseline noise, which also helps determine the limit of detection is dependent upon the flow rate (i.e. convection). A number of different geometries have been reported, with the band and disks being among the most common.

Microelectrodes, in general, have been studied extensively and reviews have been published. Microelectrodes have been used in complex media such as blood and urine. They have also been used to provide spatially-resolved information from surfaces and cell membranes. A host of biosensor applications has been reported.

The most commonly studied microelectrode geometry is the disk because it is relatively simple to construct and can attain true steady state current. Both planar (PDM) and recessed disk (RDM) microelectrodes have been studied. A recessed microdisk resides at the bottom of a cavity whose walls are made of insulator material. Although the current measured at RDMs is typically less than that at PDMs of equal radius, it can be independent of convection outside of the cavity, depending upon the cavity's dimensions and the strength of the convective forces. Two components give an RDM its unique properties: the size of the electrode and its position, which is set back from the main plane of the insulating layer of the substrate.

Recessed microdisk electrodes were originally constructed from in-plane microdisk electrodes. Either chemical or electrochemical etching has been used to etch the electrodes away from the surface plane of the insulator. The depth of the cavity and surface roughness of these electrodes are difficult to control. The early applications included chemical measurements in convective systems.

The incorporation of membrane proteins and enzymes into modifying layers on surfaces is of interest for model systems of biomembranes and for the development of chemical sensors. Membrane protein structure and function are highly dependent on the surrounding environment, and thus, it is essential to design materials on surfaces that provide the necessary characteristics to host such proteins. Langmuir-Blodgett (LB) techniques have been used to assemble phospholipids onto surfaces to provide biomembrane-like environments. These assemblies have been characterized by AC impedance measurements, X-ray photoelectron spectroscopy (XPS), and atomic force microscopy. Another more recent method that has the advantage over LB methods of ease of formation involves vesicle fusion to surfaces to form hybrid bilayers. In this method, the chemistry of the strong interaction of sulfur with gold is used to form self-assembled monolayers (SAMs) to produce a first layer. This layer provides the driving force for deposition of a second layer of phospholipids by hydrophobic coupling of phospholipid vesicles to the SAM layer. The first layer is chemisorbed rather than physisorbed and highly ordered, which provides a more ordered foundation for additional multilayer construction. Also in forming the second layer, a water rinse, rather than an organic solvent rinse, flushes away unbound vesicles and lipids without removing biomolecules incorporated within the surface-confined layers.

An area of great importance is the incorporation of biological molecules onto electrodes to aid in electrochemical detection of analytes. An important aspect is the chemistry behind modifying the electrode without destroying the activity of the biological molecule, many chemical methods have been developed to modify electrode surfaces. Immobilizing methods for biological molecules such as enzymes include covalent bonding, adsorption, monolayer deposition, entrapment, and microencapsulation. Currently, SAMs are being studied as immobilization tools because of the ease with which they create highly ordered organic films. A recent example is use of SAMs of alcohol-terminaled alkanethiols and glucose oxidase on gold electrodes to prepare a glucose sensor.

Providing the necessary hydrophobic and hydrophilic properties on the electrode surface is a challenging problem. The native environment for many proteins and enzymes is the cellular biomembrane. Several methods are being developed to artificially recreate that environment on electrode surfaces. Surface-confined lipid membranes on electrodes have been formed with Langmuir-Blodgett (LB) techniques and by combining SAMs with phospholipid vesicles. Controlling access to the underlying surface has been demonstrated using gate sites through a monomolecular LB film.

Bilayer formation using SAMs and phospholipid vesicles has been studied by electrochemistry and surface plasmon resonance properties of hybrid bilayers by cyclic voltammetry using $Fe(CN)_6^{3-}$ as the redox species in an electrolyte solution of 1 M KCl and determined that the presence of the hybrid bilayer reduces the rate of electron transfer by approximately two orders of magnitude from that of the bare electrode. Plant has also compared capacitance values obtained by impedance measurements of SAMs of alkanethiols to those of hybrid bilayers of octadecanethiol ($C_{18}SH$) and 1-palmitoyl-2-oleoylphosphhatidylcholine (POPC) and reports that hybrid bilayers are sufficiently flexible to accommodate a molecule such as a pore forming mellitin. A glucose sensor that is based on a similar bilayer-self assembling technique has also been reported. This method involves using tetracyanoquinodimethane (TCNQ) that resides within a dodecanethiolphosphatidylcholine and phosphatidylethanolamine bilayer, and serves as a mediator between the underlying electrode and overlying, cross-linked glucose oxidase. However, the bilayer thickness, estimated from impedance measurements, was smaller than typical values reported in the literature, and the TCNQ diffused out of the bilayer during electrochemical measurements.

Membrane assembly methods have been used in conjunction with enzyme reconstitution procedures to modify the electrode surface and study the electron-transfer reaction of immobilized bovine cytochrome c oxidase. Cyclic voltammetry and potential step chronoabsorptometry were used to show the direct electron transfer between the gold substrates and the cytochrome c oxidase incorporated in a dodecanethiol and 1-palmitoyl-2-oleoylphosphhatidylethanolamine (POPE) and POPC layers. In addition, the immobilized enzyme was shown to both reduce and oxidize the cytochrome c in solution. Others have used vesicles formed from molecules with head groups having a net positive or negative charge such as dimethyldioctadecylammoniumbromide (DODAB) and dimyristoyl phosphatidylglycerol (DMPG), respectively. Lipid bilayers and trilayers on solid supports can be formed by fusing these charged vesicles to a charged monolayer such as carboxylate mercaptans directly or via a cation linkage. These layers have been analyzed by impedance and surface plasmon resonance to determine the mean thickness of the membranes. Impedance analysis combined with spectroscopy has provided discrimination in identifying between specific and non-specific adsorption of streptavidin and biotinated-lipids.

Techniques to create supported bilayers using vesicles that form a top fluid layer of phospholipids onto a fixed SAM have also been demonstrated. Permeation of ions through these bilayers was studied upon incorporating the pore-forming peptide mellitin. A glucose sensor that is based on a similar bilayer-self assembling technique has also been reported. The assembly involved tetracyanoquinodimethane which resides within an alkanethiol/phospholipid bilayer, and serves as a mediator between the underlying electrode and overlying, cross-linked glucose oxidase.

Because of its simple composition and characteristic function dependence on structure, Gramicidin A is used as a convenient probe to evaluate modifying layers on electrodes. This small ion channel-forming peptide is one of the best characterized and most extensively studied membrane polypeptides. It is an antibiotic that is isolated from *Bacillus brevis* and is active against Gram-positive bacteria. It consists of an alternating L, D pentadecapeptide with the primary sequence of $HCO-L-Val-Gly-L-Ala-D-Leu-L-Ala-D-Val-L-Val-D-Val-(L-Trp-D-Trp)_3-L-Trp-NHCH_2CH_2OH$. The 3-dimensional conformation of gA is complex and dependent upon its environment. In biological or model membrane systems, gA adopts an ion channel conformation which allows the passage of water and small, monovalent cations. The channel is in the form of two β-helical monomers that dimerize end to end with the formyl-NH ends associated in the center of a lipid bilayer. The length of the dimer is approximately 26 Å. The peptide backbone forms a hydrophilic pore that has a diameter of about 4 Å. Gramicidin A has been characterized in only a few electrode-modified systems. Evidence has been presented of the selectivity of gA toward metal mono cations on electrode surfaces. Gramicidin was incorporated into dioleoyl phosphatidylcholine and bovine brain phosphatidylserine monolayers using LB techniques on mercury drop electrodes. By cyclic voltammetry, selective permeability to $Tl^+$ over $Cd^{2+}$ for layers containing gA is consistent with the gA being in the ion channel conformation. This system is not easily conducive to further evaluations by spectroscopy due to the nature of mercury. Different preparation techniques for supported lipid layers have been evaluated by impedance analysis. Gramicidin has been incorporated into one type of film, a SAM of 3-mercaptopriopionic acid, covered with a bilayer of DODAB, formed from fusion of DODAB vesicles, to create trilayer films. Again, spectroscopic characterization was not performed. However, electrochemical behavior was observed in the presence of $Cs^+$ and $Sr^{2+}$ that might be interpreted as gramicidin channels controlling ion permeation through the film.

It is therefore desirable to produce both tubular nanoband and recessed disk microelectrodes within a microcavity capable of detecting electrical currents undistorted by convection of a solution.

It is also desirable to produce microcavities having microelectrodes and a lipid bilayer extending across the top of the microcavity.

It is also desirable to produce microcavities having microelectrodes, a lipid bilayer, and a hole in the bottom to reduce osmotic effects.

It is also desirable to produce arrays of microcavities.

It is also desirable to develop an accurate, efficient and reproducible method for creating microcavities or arrays thereof having microelectrodes, lipid bilayers and holes to reduce osmotic effects.

BRIEF SUMMARY OF THE INVENTION

Construction and characterization of microfabricated recessed disk microelectrodes (RDMs) of 14 and 55 μm diameter are reported. For evaluation of electrode function, both faradaic current in $Ru(NH_3)_6^{3+}$ solution and charging current in $KNO_3$ solution were measured with cyclic voltammetry. The experimental maximum current was measured and compared to values calculated, assuming radial and linear diffusion. At slow scan rates (0.1 Vs$^{-1}$), where radial diffusion dominates, the steady state measured with 55 μm RDM is 53.5±0.48 nA and the 14 μm RDM is 5.39±0.96 nA. The calculated current based on recessed disk theory for these diameters of electrodes is 34.9 and 6.10 nA respectively. The calculated current based upon planar recessed disk microelectrode theory is 41.4 and 10.5 nA respectively. At fast scan rates (204 Vs$^{-1}$), where linear diffusion dominates, the current measured with the 55 μm RDM is 784.6±42.0 nA and the 14 μm RDM is 35.4±9.5 nA. The predicted current, based on linear diffusion, is 1274 nA and 82.6 nA, respectively. The large deviations at fast scan rates are due to uncompensated resistance. The dependence of capacitance on scan rate of the RDMs was found to be similar to that of a macroelectrode, indicating good adhesion between the insulator and the electrode. Also, the application of the RDMs to convective systems is discussed. Chronoamperometry of $Ru(NH_3)_6^{3+}$ in $KNO_3$ in both static and stirred solutions was performed using the RDMs and the current is compared to those from a planar disk microelectrode (PDM). The signal-to-noise ratio of the RDM compared to the PDM is on average four times greater for both of the stirred solutions.

The work reported here makes several new contributions to the current literature on microfabricated RDMs. First, the microfabricated RDMs are smaller (14 and 55 μm diameters) than those reported by others (~1 mm), with greater depth-to diameter ratios (0.29 and 0.07, compared to 0.015 and 0.04), which should improve performance in convective systems. Scanning electron microscopy was used to evaluate the general shape and quality of the cavities. Second, we present a detailed evaluation of the eltrochemical responses of the mircofabricated RDMs and compare them to theory. Although characterization has been performed previously on RDMs that were not microfabricated, conclusions based on those studies may not be valid for microfabricated RDMs. A different behavior may result because of the difference in materials used and extensive processing involved. The electrochemical response in $Ru(NH_3)_6^{3+}$ is compared to theory for linear and radial diffusion. Capacitance was determined from cyclic voltammetry in 0.5 M $KNO_3$ and is compared to that for a macroelectrode. This latter comparison elucidates the quality of the seal between the insulator and the electrode. Third, evidence from chronoamperametry in stirred $Ru(NH_3)_6^{3+}$ solution shows the advantages of microfabricated RDMs vs. PDMs in convective systems.

The characterization and application of a cavity electrode system (CES) containing individually-addressable recessed microdisk and tubular nanoband electrodes is discussed. Two diameters of CES, 13 and 53 μm, are described. The depth of each cavity is 8 μm. Each of the electrodes is characterized in $Ru(NH_3)_6^{3+}$ and $KNO_3$ solution at 0.1 Vs$^{-1}$. The experimental current measured at the electrodes in the 53 μm CES were within error of models for radial diffusion to the respective geometry. The experimental current for both electrodes in the 13 mm CES deviated from the models. The band electrode exceeded the model (6.31±0.28 nA compared to 3.98 nA). The disk electrode was less than the model predicted (2.13±0.46 nA compared to 3.81 nA). The formation and stability of a Ag/AgI pseudo reference electrode on the band electrode is shown. The E° for $Ru(NH_3)_6^{3+/2+}$ measured with the Ag/AgI electrode is −0.053±0.016 V. The reference electrode was found to be stable over multiple experiments without supporting electrolyte. The complete electrochemical cell (working electrode, reference and auxiliary electrode) was used for analysis in small volumes (1 and 10 μL) of hydroquinone and $Ru(NH_3)_6^{3+}$. Finally, the CES was used in stirred solutions. The signal-to-noise ratio (SNR) from 13 μm CES showed no dependence upon stir rate up to 150 rotations per minute (rpm). The SNR from the 55 μm CES showed only a small change with stir rates up to 150 rpm.

Hybrid bilayers were constructed by fusion of vesicles of dimyristoylphosphatidyl choline (DMPC), which forms the top layer, with ethanol-rinsed SAMs of hexadecanethiol on gold, which form the bottom layer. Gramicidin A was included in the modifying solutions to incorporate it into hybrid bilayers. Results from Polarization-modulation Fourier-transform infrared reflection-absorption spectroscopy (pM-FTIRRAS) and X-rayphotoelectron spectroscopy (XPS) on such hybrid bilayers are reported for the first time. A comparison is made between those results and ellipsometric and electrochemical measurements in $KNO_3$ and $Mg(NO_3)_2$ solutions. Capacitance determinations by cyclic voltammetry (at 0.0 and 0.4 V VS. Ag/AgCl) and AC impedance (at 0.0 V vs. Ag/AgCl) are discussed. PM-FTIRRAS and ellipsometry reproducibly demonstrate that bilayers are indeed formed. XPS analysis of the bilayers showed evidence of the presence of DMPC and gA, although results were not very reproducible, presumably due to sample damage during analysis. The capacitance in $KNO_3$ solution for the gA-containing bilayer is higher than that for bilayers without gA. The opposite trend occurs for solutions of $Mg(NO_3)_2$. PM-FTIRRAS and XPS of the SAM layers alone, assembled in the presence of gA do not show evidence of the presence of gA. However, those SAMs exhibit higher relative capacitance in $KNO_3$, but a lower relative capacitance in $Mg(NO_3)_2$ than SAMs assembled in the absence of gA.

Gramicidin A was assembled into organic films on electrodes to create and study possible materials for electrochemical sensing One assembly method involves self-assembled "monolayers" (SAMs) from hexadecanethiol ($C_{16}SH$)+gA mixtures followed by different solvent rinses. Ethanol rinses yield monolayers, but appear to remove gA. Water rinses form multiple layers of $C_{16}SH$ and gA. A second assembly method reproducibly forms bilayers by disruption or gA-containing vesicles or dimyristoyl phosphatidylcholine (DMPC) onto ethanol-rinsed SAMs of $C_{16}SH$+gA followed by a water rinse. Ellipsometry verified the number or layers or molecules in the films on the surfaces. Permeation or $Fe(CN)_6^{3-}$ is essentially negligible at all films. Electrochemical responses to $K^+$ and $Mg^{2+}$ at bilayers and to $Ag^+$ and $Pb^{2-}$ at water-rinsed SAMs is consistent with the selectivity of the channel former of gA. The mere presence of gA might also cause this selectivity. Exact conformation of gA in these films has not yet been determined.

Two ways are demonstrated to assemble membrane proteins onto electrode surfaces for the purposes of developing chemical sensors and studying protein-membrane interactions. Gramicidin A is incorporated into these assemblies. The gA serves as a probe of the surrounding molecular environment and allows selective permeation of monovalent cations and blocks multivalent cations and anions. One means of assembly is the simultaneous self assembly of gA with hexadecanethiol to form mono- or multilayers onto a gold electrode surface. The spontaneous adsorption of organothiols onto gold to form SAMs has become popular due to its simplicity, versatility, reproducibility and many possible applications. The second assembly structure is a supported hybrid bilayer that is formed from a combination of SAMs of hexadecanethiol with gA and vesicles of phospholipids containing gA. Studies on these molecular assemblies involved ellipsometry, capacitance measurements, and permeation of redox molecules.

DETAILED DESCRIPTION OF THE INVENTION

Alkanethiols bind to both gold and fatty acids. These qualities are taken advantage of in order to create microcavities having lipid bilayers extended across their openings. Various membrane proteins may be inserted into these bilayers using the methods described below. This facilitates the study of protein mediated membrane transport, especially of molecules that are readily susceptible to electrochemical detection. A hole may be made in the bottom of the cavities in order to relieve osmotic pressure, thereby increasing the accuracy of electrochemical transport analysis. It is also possible to create large arrays of these bilayer covered cavities. This allows for faster gathering of more data and also provides the ability to study a variety of electrochemically susceptible molecular species within a single solution sample. The methods for forming these structures, as well as the physical characteristics of these microcavities is discussed in detail in the following examples:

EXAMPLE 1

Materials

All chemicals were reagent grade and used as received. Aqueous solutions were prepared with high purity deionized water (Mille-Q, model RG). A gold coin (Credit Suisse, 99.99%) and chromium plated tungsten rod (R.D. Mathis) served as sources for thermal evaporation. Silicon wafers (5", (100) were obtained from Silicon Quest International (Santa Clara, Calif.). Potassium nitrate, sulfuric acid, hydrochloric acid, nitric acid and 30% hydrogen peroxide were purchased from Fisher Scientific. Hexaamine-ruthenium (III) chloride was obtained from Alderich Chemical Co. Positive photoresist (AZ330RS) and photoresist developer (AZ00K) were purchased from Hoechst-Celanese. Polymide (Pyralin PI-2721, DuPont) was purchased from DuPont. A gold 10 μm diameter PDM (BioAnalytical Systems) BAS was used as the control.

Electrochemical Measurements

A BAS-100B potentiostat and PA-1 preamplifier controlled with BAS-100W electrochemical software were used to perform cyclic voltammetry (CV) and chronoamperometry (CA). The electromechemical cell contained a Pt flag auxiliary electrode and Ag/AgCl (saturated KCl) reference electrode. For CV experiments, a solution of 5.0 mM $Ru(NH_3)_6^{3+}$ and 0.5 M $KNO_3$ was purged with Ar to minimize the oxygen content. Stirring studies involved CA and were performed on a Corning PC-320 stir plate with ½" magnetic stir bar (Fisher Scientific). The cell volume was 40 mL and was not purged prior to CA. The rotation rate was determined by counting the rotations of the stir bar over a given period. Au macroelectrodes were made by depositing 15 Å of Cr followed by 2000 Å of Au on an oxidized Si wafer. the preparation of the Si wafer and formation of a passivating oxide layer is the same as described below for the mircofabrication. Uncompensated resistance measurements were made using the BAS-100B. A 25 mV DC potential was applied in a 0.5 M $KNO_3$ solution.

Construction of Recessed Disk Microelectrodes

Figure 1:
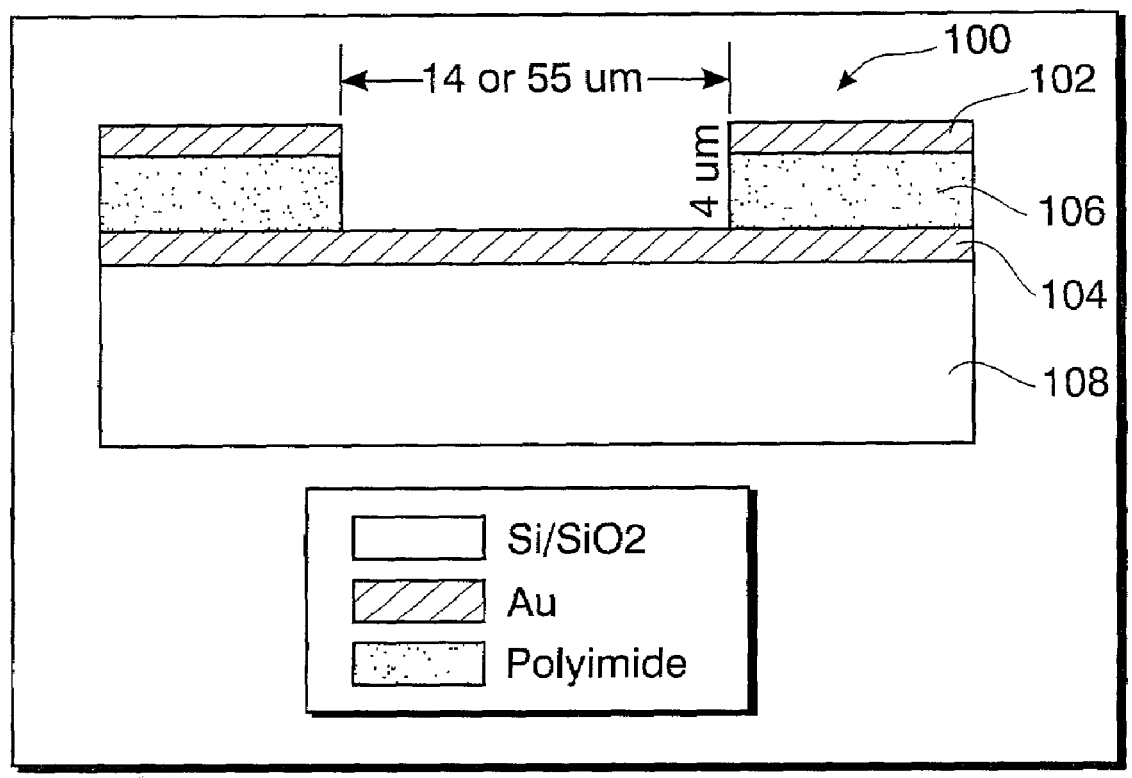
FIG. 1 shows a diagram of a cross-section view (not to scale) of a single cavity.

The fabrication or RDMs was accomplished by forming a hole through a Au and polymide layer exposing an underlying Au Disk. FIG. 1 shows a cross-section view of an RDM 100. Bottom Au layer 104 is a recessed disk microelectrode. It is separated from top Au layer 102 by insulating layer 106. Substrate 108 is typically a silicon wafer, but may be comprised of a number of other materials. The top later of Au 102, while not used in the electrochemical measurements is essential in the fabrication process so that cavities with well-defined, vertical walls can be produced. Cavity devices, that accommodate two individually-addressable electrodes, are described elsewhere. Here we focus on the use of the same design for a more simplified electrode configuration.

Figure 2:
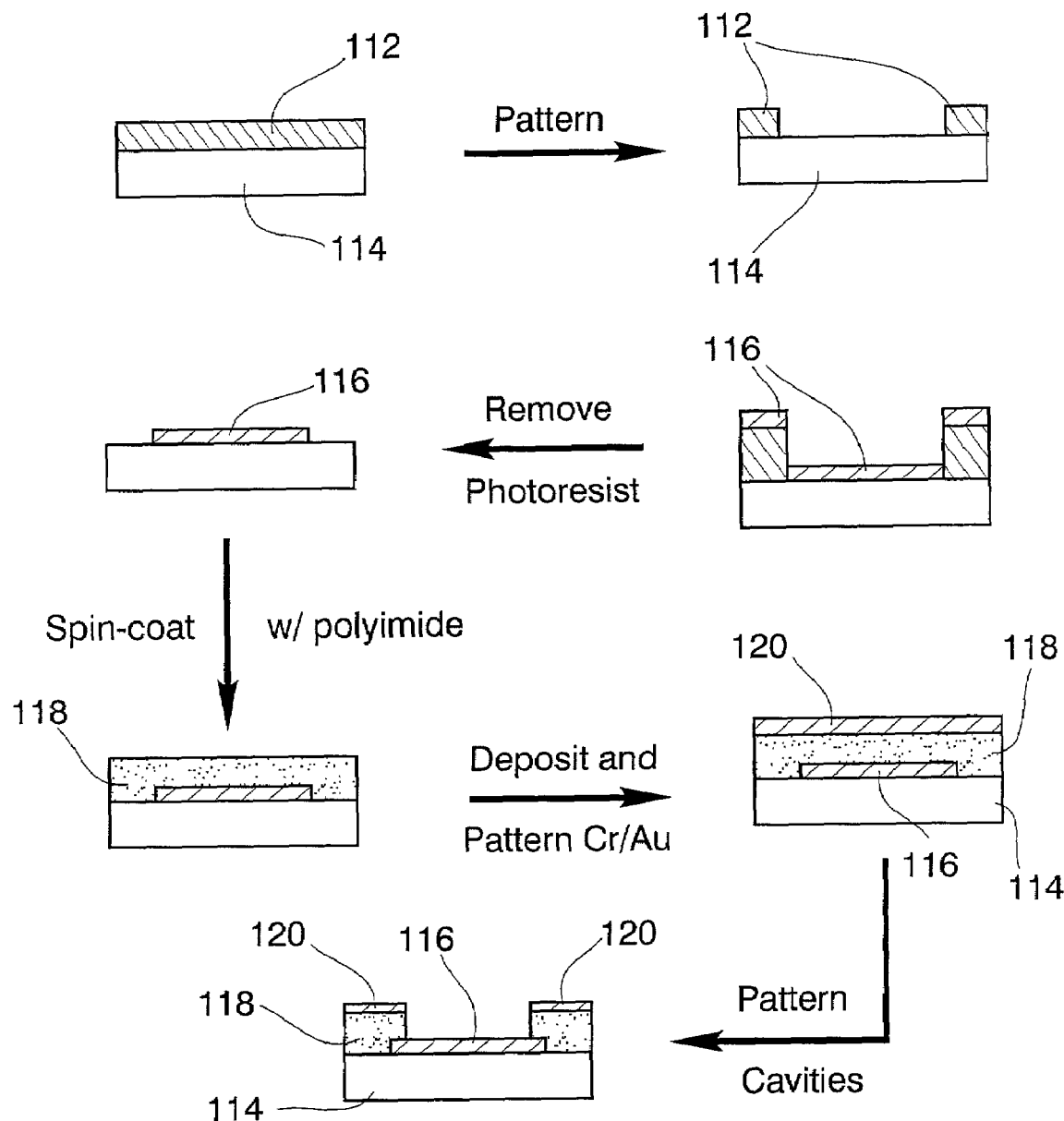
FIG. 2 shows a fabrication schematic, cross-section view.
Figure 2:
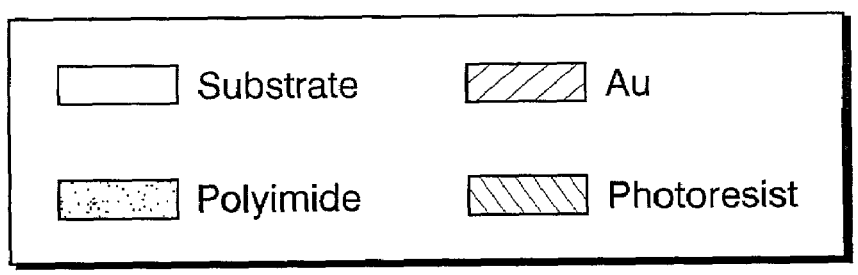

The fabrication of RDMs consists of four steps. The process is shown as a cross-section schematic in FIG. 2. A 2 μm $SiO_2$ film was grown on a Si wafer 114 by thermal oxidation. The wafer was spin-coated with a positive photoresist 112 and exposed to UV light (400 W, 300 nm) through a photolithographic mask (HTA Photomask). The photoresist was developed, leaving the pattern of a series of parallel lines, which eventually become the contact leads and microdisk electrodes. A 15 Å Cr film, which serves as an adhesion layer, and 1000 Å Au layer 116 were deposited on the photoresist by thermal evaporation (Edwards 306 Auto). The wafer was sonicated for 15 min in acetone, which dissolves the photoresist, causing lift-off of the metal on top.

After drying for 30 minutes at 125° C., the wafer was spin-coated with polymide 118 (4 μm thick). The polymide was polymerized by exposure to UV light and then cured at 150° C. for 30 minutes and 250° C. for 30 minutes to cross-link the polymer. Cr (15 Å) and Au (1000 Å) 120 were deposited on top of the polymide 118 by thermal evaporation. The wafer was spin-coated with positive photoresist. The photoresist was patterned by UV-exposure through a second photolithographic mask (HTA Photomask). The Au and Cr were etched simultaneously with 50% aqua regia (1 $HNO_3$: 3 HCl). The remaining photoresist was stripped with acetone and the wafer was dried for 30 minutes at 125° C. This left a layer of Au/Cr 116 covering the electrode lines with an area over the end of the lines left open for contact purposes.

The wafer was spin-coated with photoresist and patterned using a third photolithographic mask (Photronics). This step leaves a circular opening through the photoresist over each region defined by the lines in the first gold layer. The topmost layer of Au was etched using radio frequency (RF) sputtering (5 minutes, 50 sccm Ar, 30 mT, 500 V). The polymide was etched with reactive ion etching (RIE) (13 min, 40 sccm $O_2$, 10 sccm $SF_6$, 300 mT, 300 W). Before use, the electrodes were cleaned by sonicating in acetone for 30 s. The electrode pattern design includes 4 lines of Au underlying the polyimide. Each has one cavity of a different nominal diameter: 50 µm, 10 µm, 5 µm, and 2 µm. Only the 50 and 100 µm cavities could be formed with this set of microfabrication conditions. Scanning electron microscopy (SEM) was performed with a Hitachi S-2300 scanning electron microscope (20 kV accelerating voltage). A profilometer (Dektak 3030) was used to measure the polymide thickness.

Physical Characterization

Figure 3A:
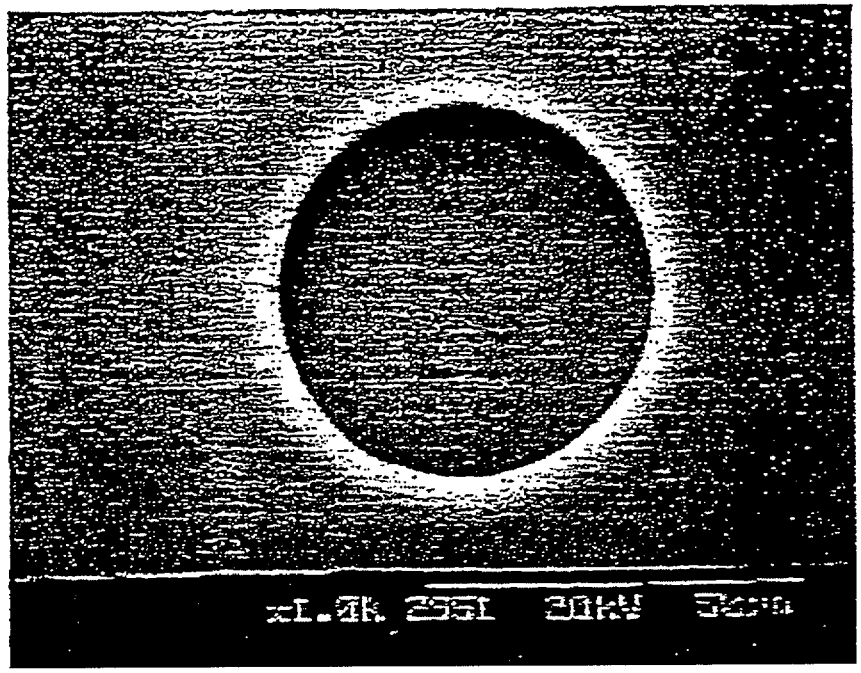
FIG. 3 shows scanning electron micrographs of (a) 55 μm and (b) 14 recessed disk microelectrodes that are 4 μm deep the 14 μm RDM micrograph shows some irregularities along the walls of the opening.
Figure 3B:
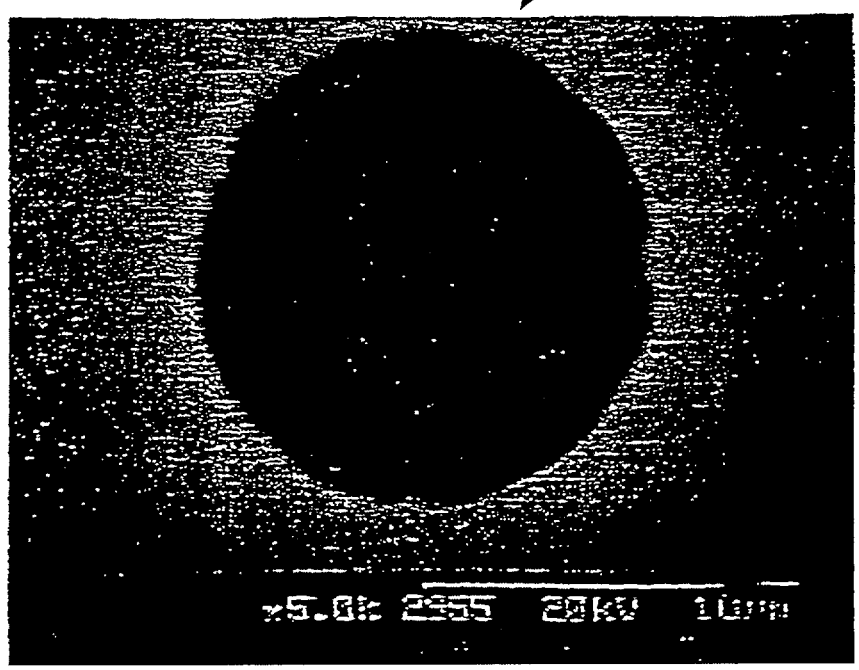

Recessed disk microelectrodes were characterized by SEM to determine shape and dimensions. FIGS. 3a and 3b show top down electron micrographs of RDMs of 14 µm 124 and 55 µm 126 diameter, respectively. The circle defines the edge of the disk at the bottom of the cavity. The larger cavity appears to have a smooth, circular opening at 1000× magnification. The opening of the 14 µm diameter cavity seems less regular (3000× magnification). The black halo that is seen around the brighter center in (b) is due to perspective effects of the SEM. Inspection with an optical microscope reveals no polymide lip between the top layer of Au and the RDM. The average diameter of the small RDMs is 14±0.28 µm (n=3 cavities). The average diameter of the large RDMs is 55.2 µm±0.0(n=3 cavities). The average diameter of the large RDMs is 55.2 µm±0.0 (n+3cavities).

The depth of the cavities was not measured directly. The small diameter of the cavity prevented the use of atomic force microscopy or a profilometer. To obtain an approximate measure of the depth, the thickness of the polymide layer was measured after patterning using a profilometer. The thickness of the polymide was consistently 4 µm.

Faradaic Response

Cyclic voltammetry was used to characterize the electrochemical response of the RDMs. Ru $(NH_3)_6^{3+}$ was chosen as a probe because of its well-established electromechanical properties. A 10 µm PDM was used for comparison. One advantage of using disk microelectrodes is that true steady state currents can be attained. Steady state current is a result of constant flux to the electrode surface. For static systems it is obtained when the mass transport is dominated by radial diffusion. In a steady state CV, at very slow scan rates where the diffusion layer is large relative to the size of the electrode, the current of the reverse scan should retrace that of the forward scan in a sigmoidal shape. In this case, pseudo steady state occurs when the time scale is short enough and the diffusion layer is thin enough so that transport involves both linear and radial diffusion. Cyclic voltammograms in this scan rate are expected to be sigmoidal, with a separation between the forward and reverse currents.

Figure 13:
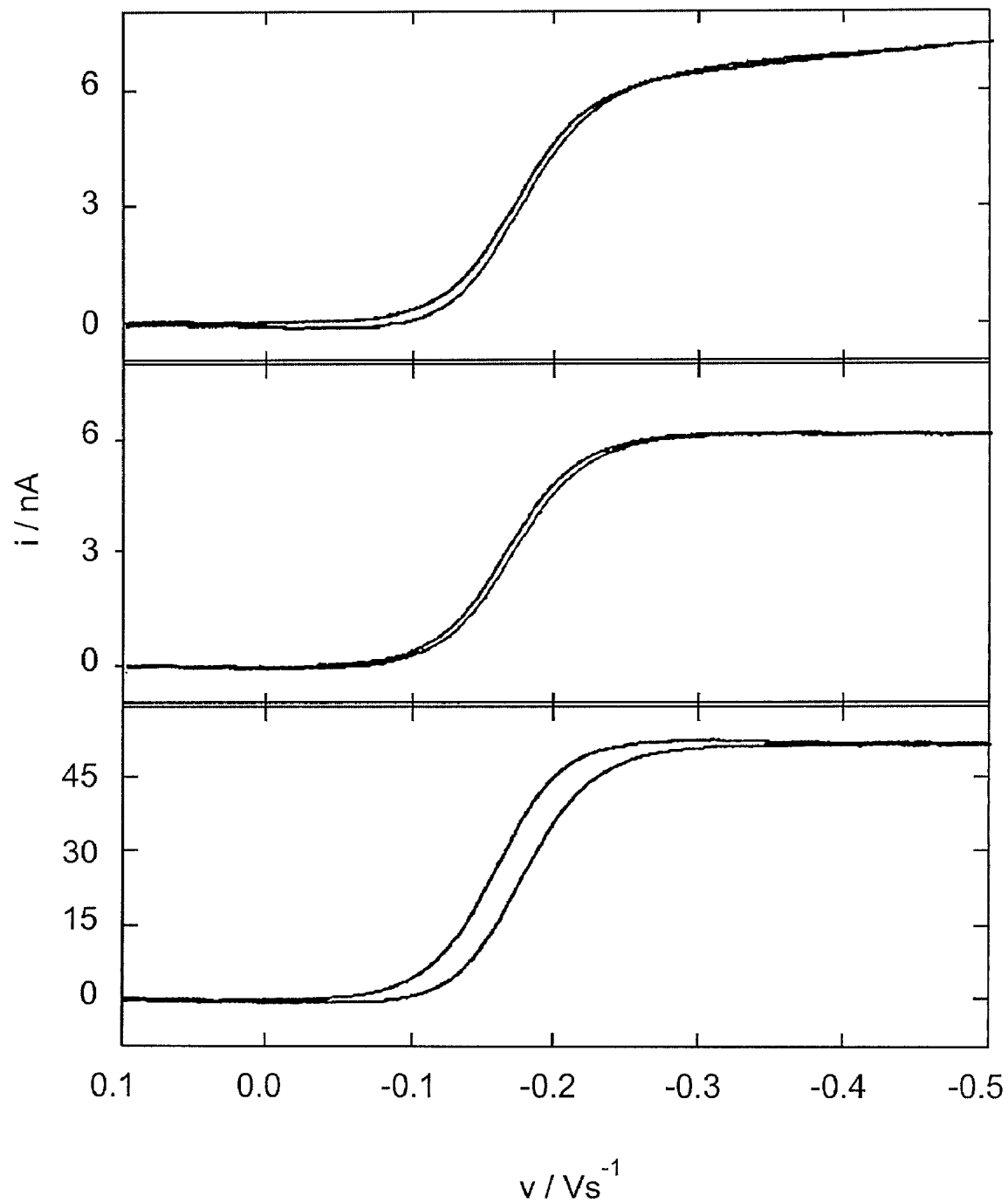
FIG. 13 shows a comparison of the CV response at 0.12 $Vs^{-1}$ in 5 mM $Ru(NH_3)_6^{3+}$ and 0.5 M $KNO_3$ from a (a) 10 um PDM (b) 14 urn RDM, and (c) 55 um RDM.

FIG. 13 shows CV responses from the 10 µm PDM (a) and the 14 µm (b) and 55 µm (c) RDMs. All three were obtained in 5.0 mM $Ru(NH_3)_6^{3+}$ and 0.5 M $KNO_3$ at 0.1 $Vs^{-3}$. At this scan rate, none of the microelectrodes exhibit true steady-state behavior. The 10 µm PDM is the closest, while the 55 µm RDM is the furthest from this behavior. The deviation occurs for two reasons. As electrode size increases, the contribution of linear diffusion to the total flux for a given time scale increases. This is the case in comparing CV responses from the 14 and 55 µm RDMs. Secondly, the walls of the cavity prevent radial diffusion from occurring as long as the diffusion layer is within the cavity. This is demonstrated by comparing CV responses of the 10 µm PDM and the 14 µm RDM.

The microelectrodes were further investigated to understand the effects of the cavity. The thickness of the diffusion layer is inversely proportional to the square of the scan rate and can be approximated by Equation 1, $$x = (2Dt)^{1/2} \quad (1)$$

where x is the thickness of the diffusion layer, D is the diffusion coefficient for $Ru(NH_3)_6^{3+}$ ($7.8 \times 10^{-6}$ $cm^2 s^{-1}$), and t is the time spent on the reducing side of $E^0$, divided by the scan rate. The scan rate at which the diffusion layer thickness is equal to the depth of the cavity (4 µm) is 58.5 $Vs^{-1}$.

Three current regions are defined. At slow scan rates, the current should be independent of scan rate (i.e. steady state). The equation used to calculate this current is shown below.

$$i_{ss} = (4\pi n FC^* D r^2)/(4L + \pi r) \quad (2)$$

where n is the moles of electrons per mole of analyte involved in the reaction, F is the Faraday constant (98485 coul*mol electrons$^{-1}$), C* is the concentration of $Ru(NH_3)_6^{3+}$, L is the depth of the cavity, and r is the radius of the disk. A decrease in current relative to planar disk microelectrodes (PDMs) of the same radius is expected. For PDMs (where L=0), the steady state current is.

$$i^{ss} = 4nFC^*Dr \quad (3)$$

At faster scan rates, there will be a transition region where neither steady state nor linear diffusion models completely apply. At fast scan rates relative to the depth of the cavity and area of the electrode, the current should follow the model for linear diffusion and be proportional to the square root of scan rate, $v^{1/2}$.

$$i_p = (2.69 \times 10^5) n^{3/2} A D^{1/2} v^{1/2} C^* \quad (4)$$

where A is the area of the electrode ($\pi r^2$).

Figure 5:
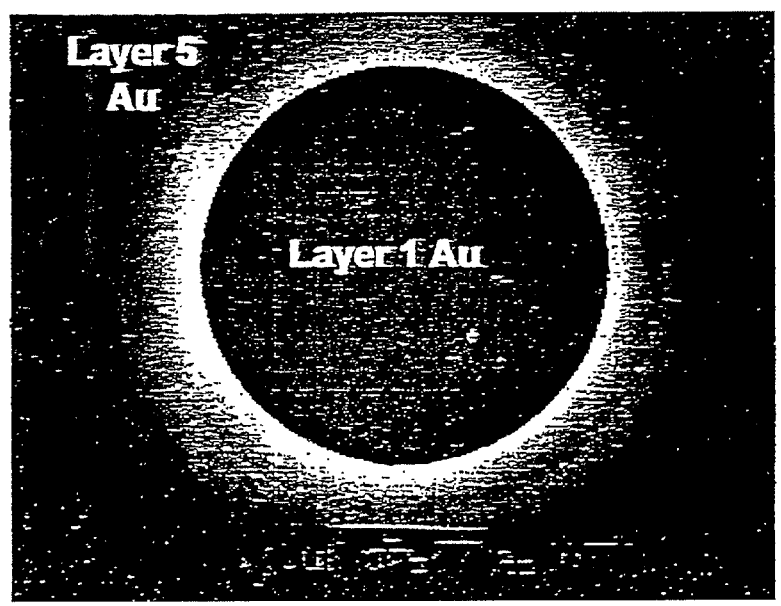
FIG. 5 shows scanning electron micrograph (SEM) of the cavity microelectrode system. This top down view shows only layer 5 and layer 1 (Au).
Figure 6:
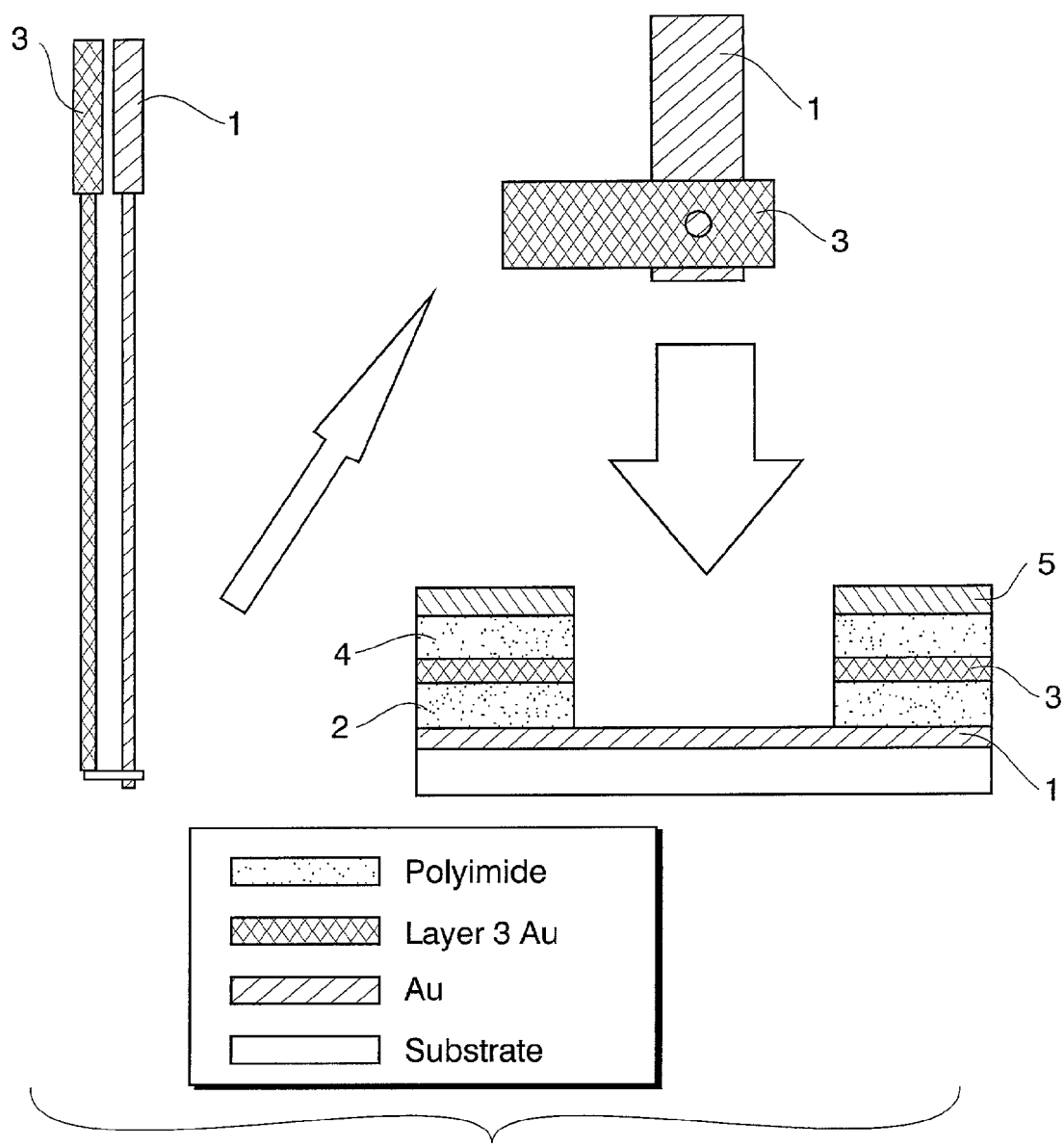
FIG. 6 shows a schematic of CES showing (a) the top-down view of two electrodes of the pattern, (b) an enlargement of the region where the cavity is located, and (c) a cross section of the cavity.
Figure 7:
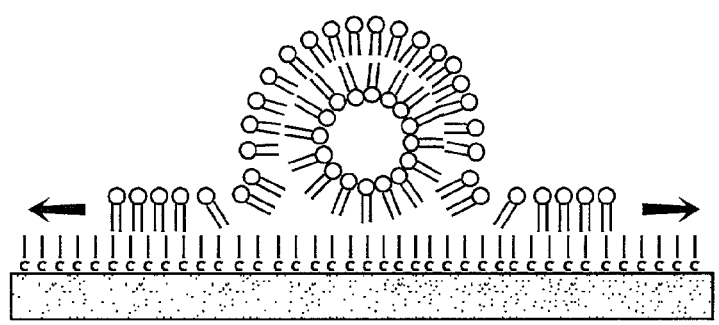
FIG. 7 shows how bilayers were constructed by allowing phospholipid vesicles to assemble from an aqueous suspension onto ethanol-rinsed, SAM-modified electrodes.
Figure 8:
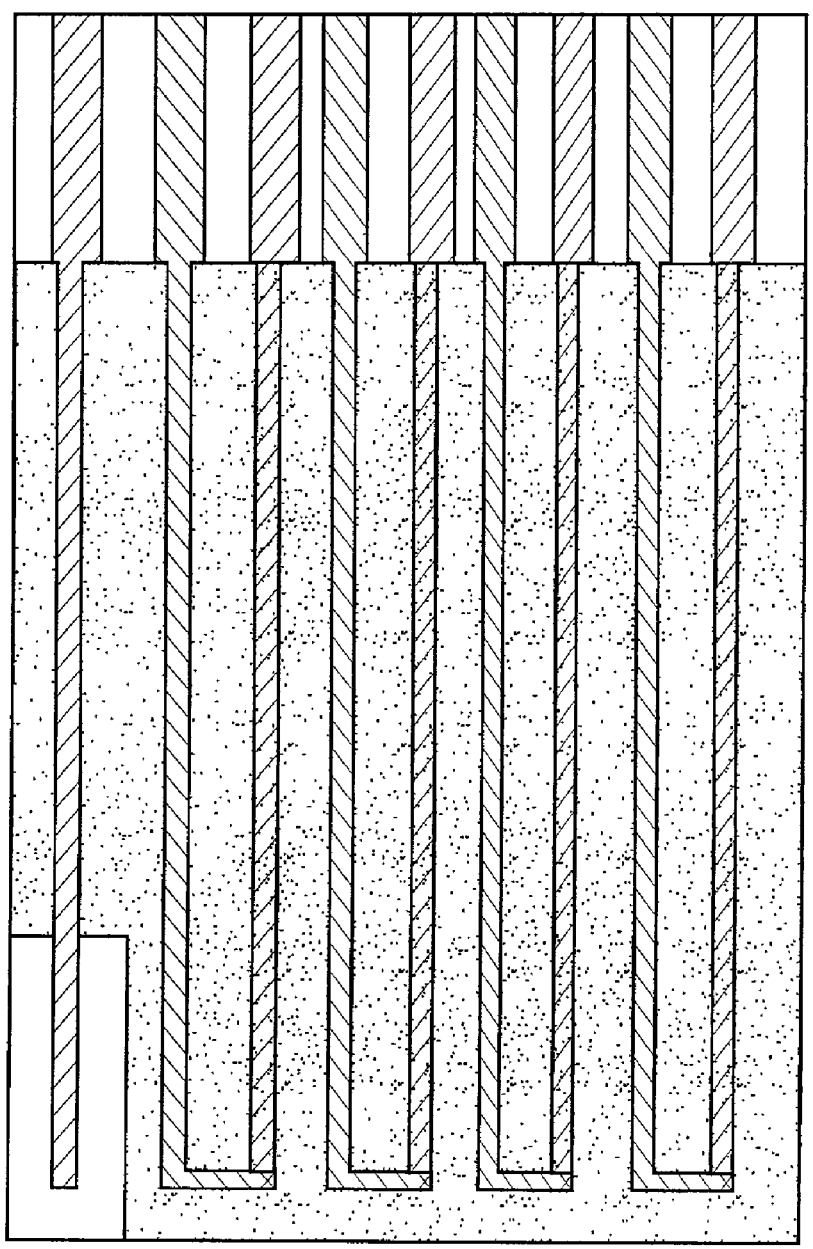
FIG. 8 shows a top down view of the electrode array showing the layers and positioning of the individual electrodes. The electrodes colored blue are in the bottom plane and constitute the disk electrodes shown in FIG. 9. The two insulator layers are represented by the cross-hatched areas. The insulator is polymide for these devices. The red colored electrodes are the second electrode layer. They are the tubular band electrodes in FIG. 9. The top later is gold. This layer was necessary to defined a cavity with straight walls. (See FIG. 9) In this figure, it is also defined by the cross-hatched area.
Figure 8:
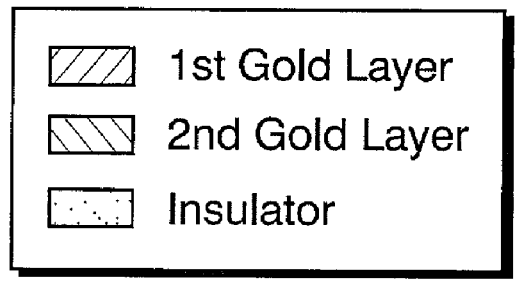
Figure 9:
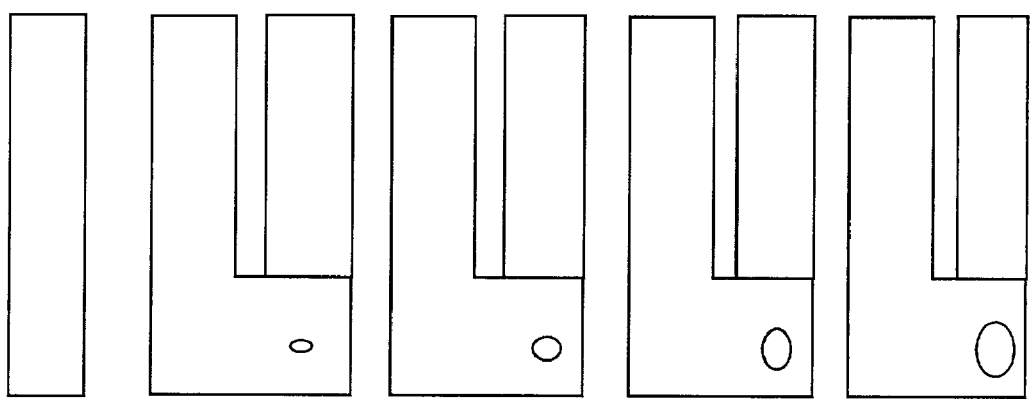
FIG. 9 shows the location and size of the cavities from the top down view and a side view of a representative cavity showing the arrangement of layers. The cavities are located in the overlap region of the two electrode layers (top schematic). The four possible cavity diameters are shown. The bottom schematic shows the altering of material inside the cavity. The black section is the silicon substrate that is used to support the electrode system. The blue and red layers correspond to appropriate electrode layers. The cross hatched sections are insulator (polymide) layers. The green layer is the protective gold layer that protects the upper lip of the cavity during processing so the shape and vertical walls of the cavity are maintained.
Figure 9:
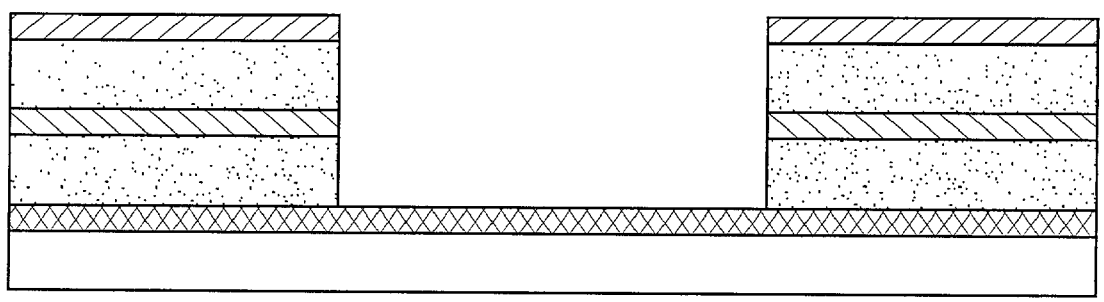
Figure 10:
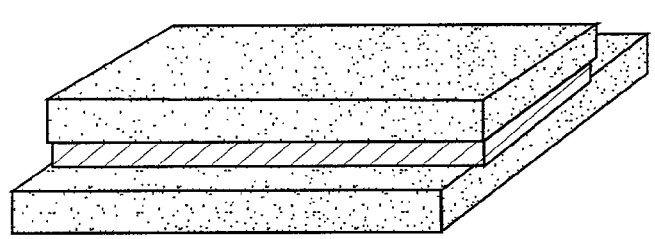
FIG. 10 shows two kinds of electrode devices and their general dimensions that will be discussed in the talk. The top one is only a 2-layer device, where lines have been etched through, exposing linear edge band electrodes along the walls and which we have presented in the past. The bottom figure is of a cross-section of a 5-layer microcavity device, which is relatively new.
Figure 10:
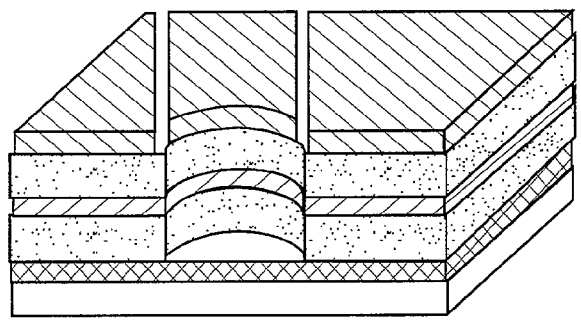
Figure 11:
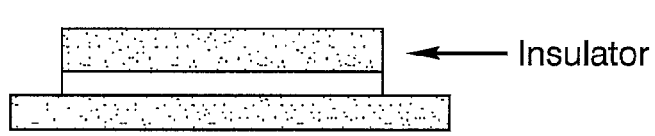
FIG. 11 shows the advantage of stacking alternating layers of insulator and conductor metal layers to increase the three dimensional functionality of the devices, while using the same substrate area. This idea has been presented on many occasions before. The multilayer microactivity electrode devices beautifully put this idea into practice.
Figure 11:
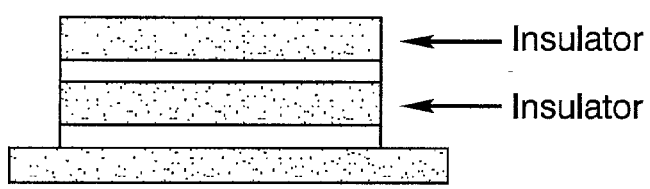
Figure 12A:
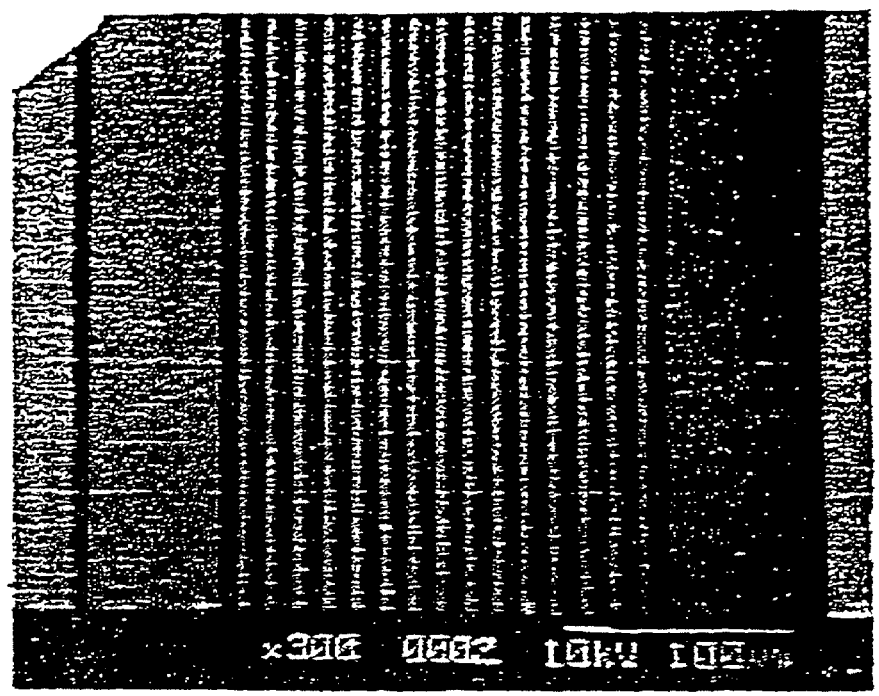
FIG. 12 shows scanning Electron Microscopy (SEM) images of (a) a top view of chromium, gold, and silicon nitride on top of glass, patterned to form 15, 4 mm band features flanked by 2,50 mm features and (b) a side view of one of the edges which contains a submicron band electrode.
Figure 12B:
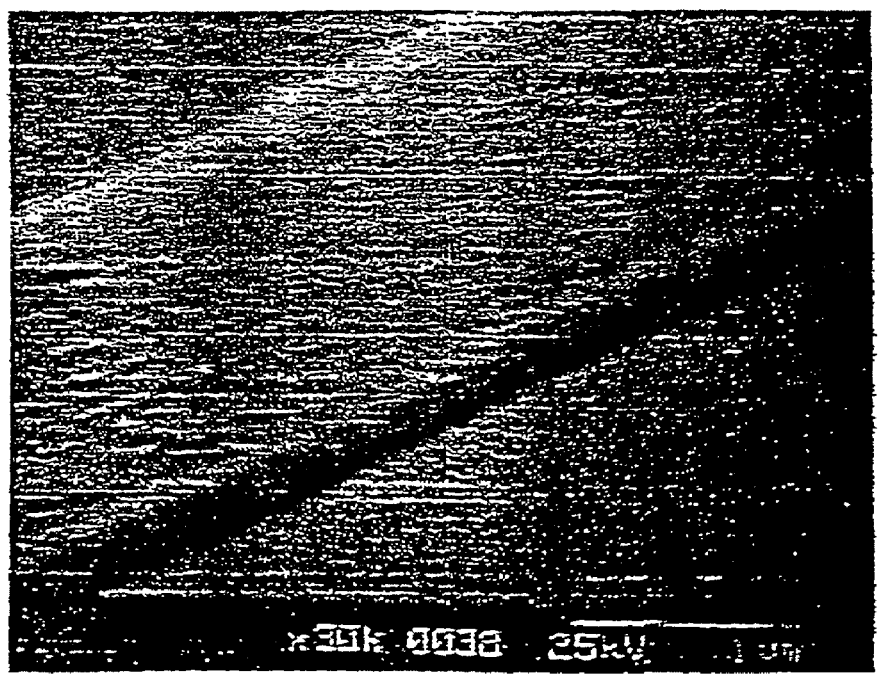

A scan rate study was performed to compare our RDMs with these models. The maximum current ($i_{max}$) was measured from the CV responses. If no peak is present, then $i_{max}$ is measured to the peak. Charging current was subtracted out. In FIGS. 5 and 6, $i_{max}$ for the microelectrodes is compared to $i_{ss}$ and $i_p$ from Equations 2 and 4 as a function of $v^{1/2}$ The top half (a) of each figure shows scan rates from 0.01 $Vs^{-1}$ to 10 $Vs^{-1}$.

For the 55 µm RDM (L=4 µm), steady state current persists to a scan rate of 0.1 $Vs^{-1}$. The steady state current for the 55 µm RDM is 53.50±0.48 nA. The steady state current predicted by Equation 2 by 34.9 nA. The steady state current predicted by Equation 3 is 41.4 nA. The steady state current predicted by Equation 3 is 41.4 nA. From this comparison, the 55 µm RDMs follow theory for RDMs better than theory for RDMs. The lower calculated current may be due to an inaccurate area determination. At faster scan rates, the current increases with scan rate in a fashion like that predicted for Equation 4. At 204 $Vs^{-1}$, where the diffusion layer is thin and the electrodes should follow theory for linear diffusion (Eq. 5), the maximum current is 784.6±41.2 nA. The current predicted by Eq. 5 is 1274 nA. This deviation between measured and predicted current is discussed below.

For the 14 µm RDM, steady state current persists up until 1 $Vs.^{-1}$ is reached. The maximum current measured at the 14 µm RDMs (5.39±0.96 nA) fits the recessed disk model of Eq. 3 (6.10 nA) better than the PDM model of Eq. 4 (10.5 nA). For the 14 µm RDM, the curves for $i_p$ and $i_{ss}$ vs. $v^{1/2}$ cross at 1 $Vs^{-1}$. Above this scan rate, the current increases with increasing scan rate. At 204 $Vs^{-1}$, the current measured at the 14 µm RDMs is 35.37±9.51 nA. The current predicted by Eq. 5 is 82.58 nA. Again, there is no apparent transition region between steady state and linear models for this size of RDM.

At fast scan rates, the current at both the 55 μm and 14 μm RDMs should be predicted by Equation 4. However, the magnitude for both RDMs is significantly lower. This is due to uncompensated resistance. The uncompensated resistance, $R_u$, was measured with the BAS. The resistance was found to be 96.6 kΩ for the 55 μm RDM and 209 kΩ for the 14 μm RDM. This is higher than that at the 10 μm paM (49 kΩ). This effect has been observed previously for RDMs 15 and for recessed microelectrode ensembles, however the resistance was not reported to be as high (15–30 kΩ).

The effect of uncompensated resistance on peak current was modeled by computer simulation. The peak current at two scan rates, 50 Vs$^{-1}$ and 204 Vs$^{-1}$, was measured from simulations at both 0Ω and either 96.6 or 209 kΩ, depending on which was appropriate. A simple ratio was obtained by dividing the current influenced by uncompensated resistance, $i_R$, by the ideal current. A similar ratio was obtained from the experimental data by dividing the experimentally measured current by the current calculated from Eq. 4 for a given scan rate. For the 55 μm RDM, the experimental ratio at 204 Vs$^{-1}$ is 0.616. At 50 Vs$^{-1}$, the ratio is 0.784. The values from simulations are 0.726 and 0.817 respectively. For the 14 μm RDM, the experimental ratio at 204 Vs$^{-1}$ is 0.428 and at 50 Vs$^{-1}$ is 0.511. The values from simulations are 0.931 and 0.981, respectively. The deviation of experimental current from planar theory at fast scan rates can be explained by uncompensated resistance at the 55 μm RDMs. The 14 μm RDM cannot be explained completely by uncompensated resistance value given above.

Charging Current

Figure 16:
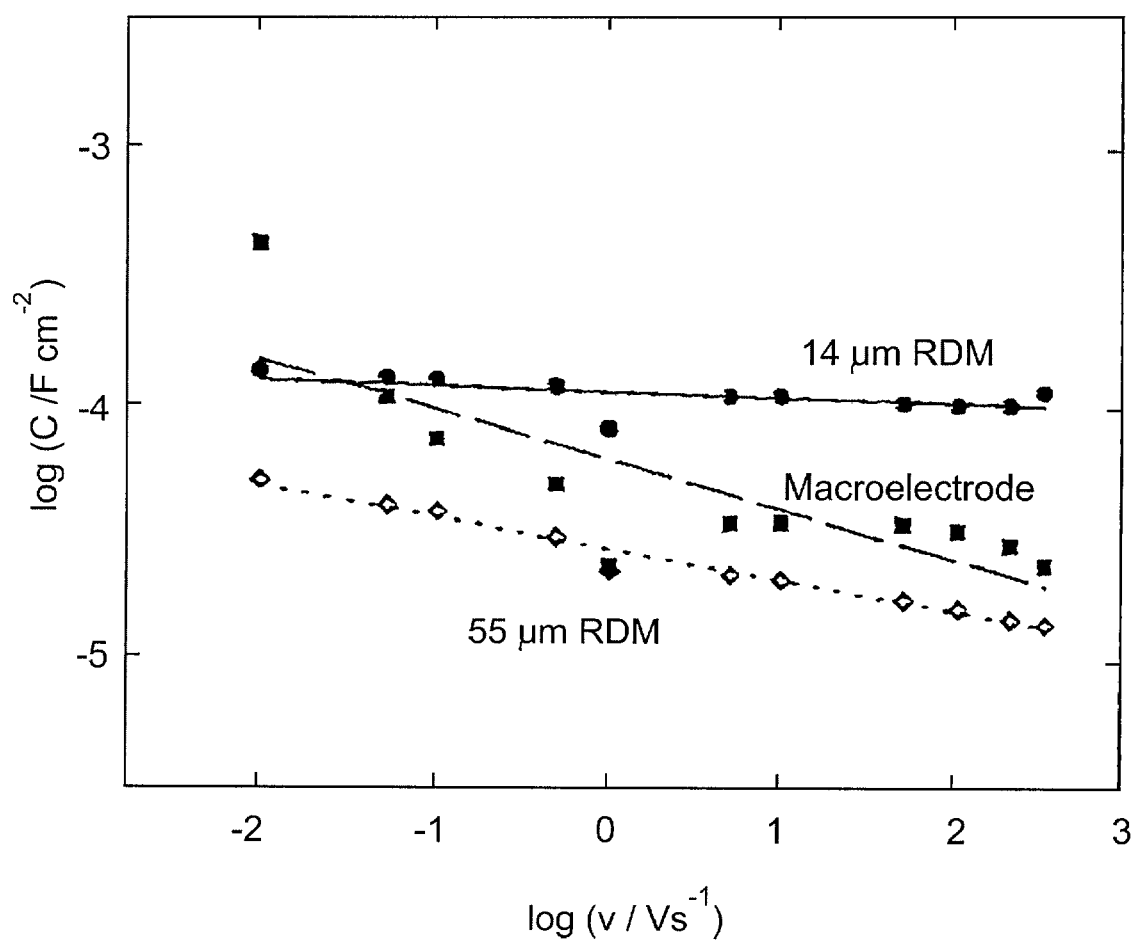
FIG. 16 shows the quality of fabrication and seal as determined by the dependence of capacitance density on scan rate. The charging current was measured from cyclic voltammograms in 0.5 M KNO $Ru_3$. Comparison is made to that from Au macroelectrode.

Capacitance studies were used to evaluate the quality of the construction of the microelectrodes. The charging current was measured from CV in 0.5 M KNO$_3$ electrolyte. The following equation was used to calculate the capacitive density.

$$C = i_c/vA \tag{5}$$

where $i_c$ is the charging current. FIG. 16 shows a log—log plot of the capacitance as a function of scan rate for an Au macroelectrode, 14 μm RDM, and 55 μm RDM. Representation of capacitance data in this form has been used previously to determine the quality of fabrication. Usually, the capacitance is considered to be independent of scan rate. However, even at the macroelectrode this is not the case. The slope for the RDMs is similar to that of the macroelectrode, indicating that the seal between the insulator and electrode is good, and no cracking has occurred. The capacitance values of the 14 and 55 μm RDMs are within a factor of 10 of each other and of the macroelectrode. The small differences may be caused by inaccurate determination of electrode area.

Convection Studies

Figure 17:
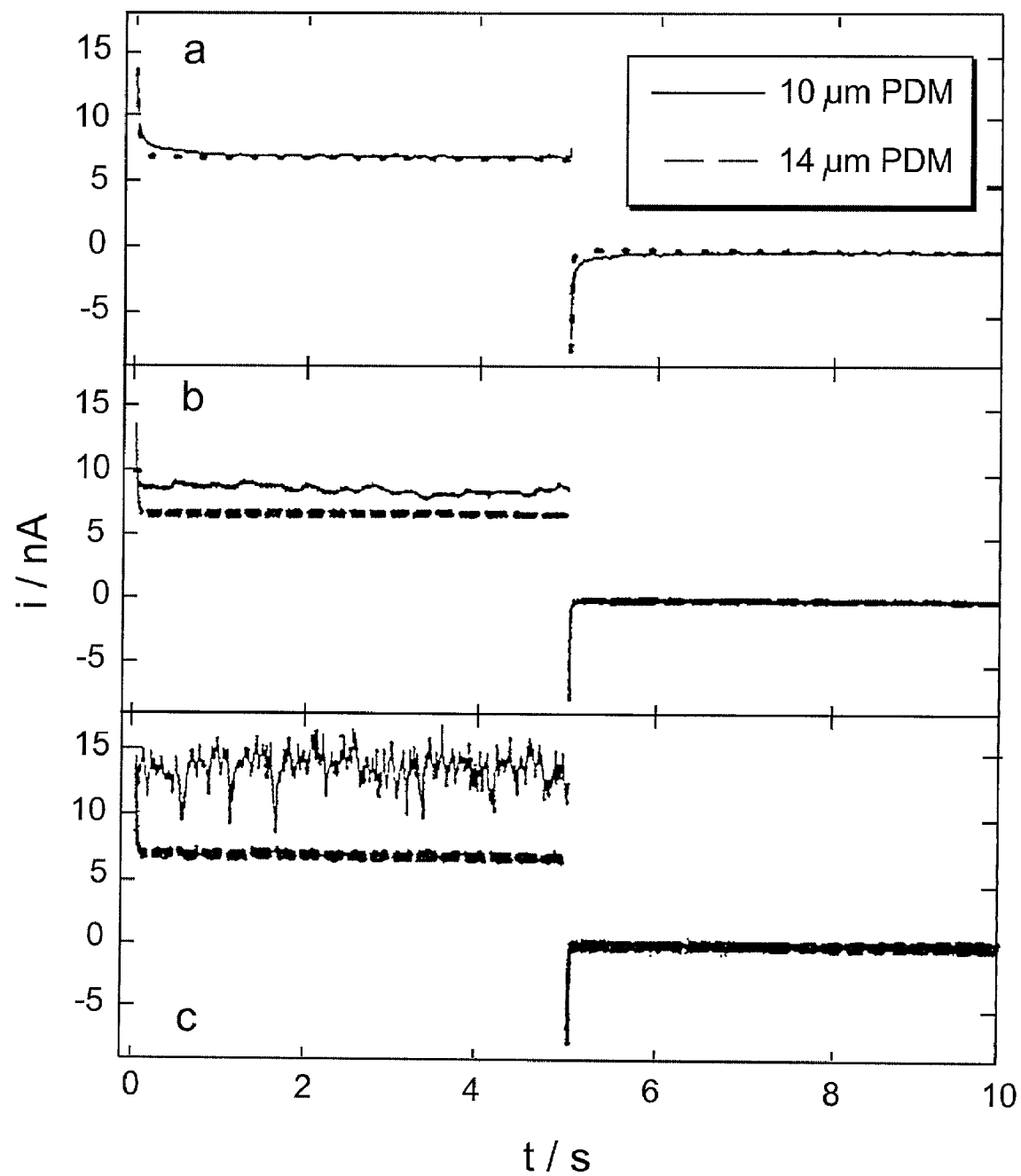
FIG. 17 shows a comparison of chronamperometric responses of a planar and disk microelectrode in 5 mM $Ru(NH_3)_6^{3+}$ and 0.5 M $KNO_3$ The solution is (a) static, (b) stirred at 70 rpm and (c) stirred at 150 rpm.

A simple set of experiments were conducted to demonstrate the utility of these microfabricated RDMs in convective systems. Chronoamperometry (CA) was carried out in a 5 mM Ru(NH$_3$)$_6^{3+}$ and 0.5 M KNO$_3$ solution. Both sizes of recessed disks were compared to a 10 μm PDM. FIG. 17 is an overlay of the 14 μm RDM and the 10 μm PDM tested in both static and solutions stirred at different rates, and is representative of all repetitions. In the static solution the current for the PDM is 7.30 nA, while the current for the RDM is 7.04 nA. The steady state current measured in the static solution can be used to determine the area of each electrode. Using Eq. 3, the effective diameter of the PDM is 9.70 μm. Using Eq. 2 for the RDM, the effective diameter is 15.5 μm.

FIG. 17 shows the response in a solution that was stirred at 70 rpm. The current measured with the PDM increased to 8.80±0.68 nA and the RDM decreased to 6.65±0.631 nA. FIG. 17 shows the response for a solution stirred at 150 RPM. The signal increases to 13.27±0.365 nA for the 10 μm PDM and the RDM increased to 7.184±0.227 nA. The signal for the 14 μm.

The performance of the RDM as an electrochemical detector is best evaluated by determining the signal-to-noise ratio (SNR). The SNR was calculated by dividing the average steady state current by the standard deviation of the steady state current during the reduction step. For the 10 μm PDM, the SNR at 70 rpm is 37.6±10.4 and at 150 rpm is 9.89±1.41. The SNR for the 14 μm RDM at 70 rpm is 116±24.7 and at 150 rpm is 46.0±12.9. This improvement in SNR is significant even though the depth of the electrode is only 4 μm and the diffusion layer extends well beyond the opening.

A similar set of experiments was carried out for the 55 μm RDM. Unlike the 14 μm RDM, the noise increased with stir rate just as if it were a PDM. This result is not surprising, although the depth of the cavity is the same. Because of the electrode's larger area, the center is less protected from convection than the 14 μm RDM. Others have reported the use of RDMs in convective solutions and noise free CA with cavities of approximately 90 μm for RDMs of 25 μm diameter. There is a correlation between noise and cavity depth with noise disappearing around a cavity depth of 50 μm for microelectrodes arrays with individual electrode diameters of 7 μm. The depth-to-diameter value of both of these systems is larger (3.6 and 7.1 respectively) than that of the microfabricated RDMs (0.29) generated in this work. Despite this difference, relatively noise free CA were obtained, however, there is still noise present that would be further eliminated with a deeper cavity.

EXAMPLE 2

All chemicals were reagent grade and used as received. Aqueous solutions were prepared with high purity deionized water (Milli-Q). A gold coin (Credit Suisse, 99.99%) and chromium plated tungsten rod (R.O. Mathis) served as sources for thermal evaporation. Silicon wafers (5", (100)) were donated by the High Density Electronics Center at the University of Arkansas. Potassium nitrate, sulfuric acid, and 30% hydrogen peroxide were obtained from Fisher Scientific. Hexaamine ruthenium(III) chloride was purchased from Aldrich Chemical Co. Positive photoresist (AZ4330RS) and photoresist developer (AZ400K) were obtained from Hoechst-Celanese. Photodefineable polyimide (Pyralin PI-2721) was purchased from DuPont.

Array Fabrication

Figure 4:
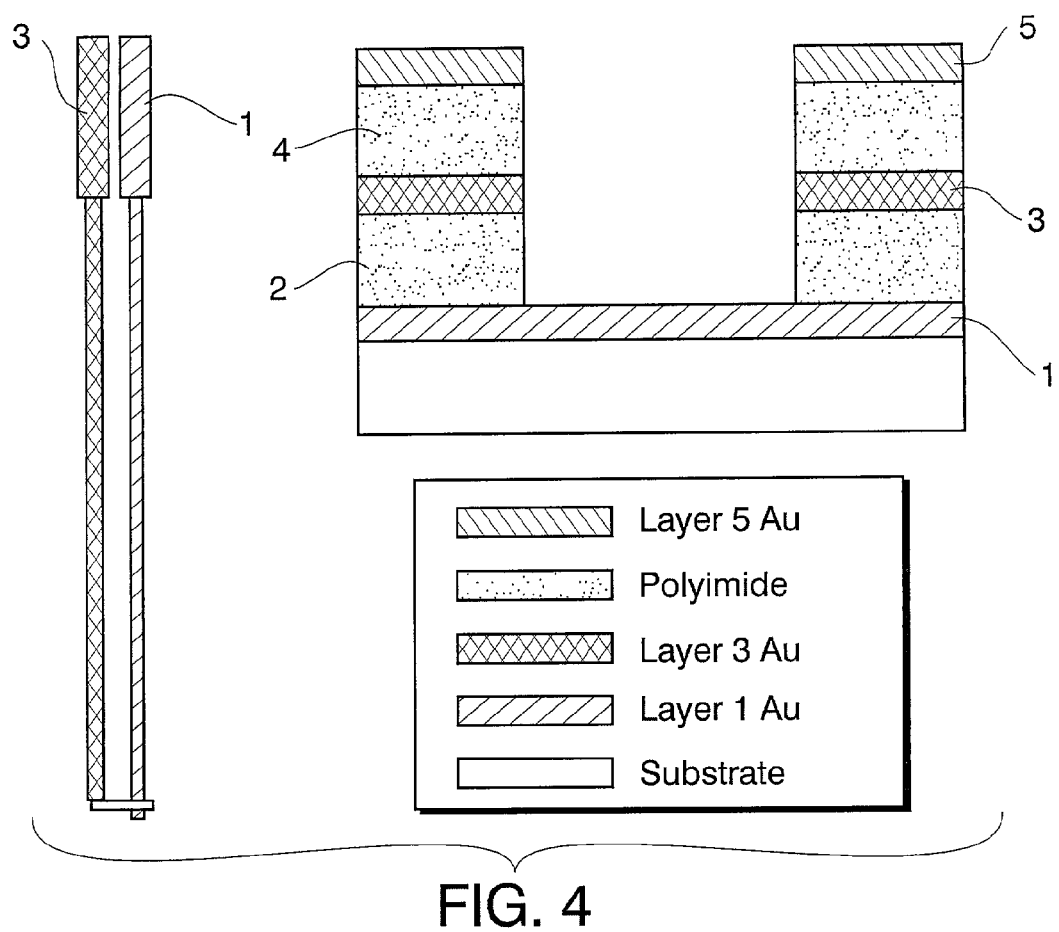
FIG. 4 shows top down and side view schematics of the cavity microelectrode system.

The fabrication of microcavity electrode arrays was accomplished through the use of photolithographic techniques developed for integrated circuit technology. A simplified version of this fabrication has been reported previously. The cavity reported here consists of 5 primary layers of material. A top down and side view schematic of the CMS are shown in FIG. 4. Layers 1, 3, and 5 are gold, with a Cr adhesion layer, while layers 2 and 4 are polyimide. Layers 1 and 3 serve as the microdisk and nanoband electrodes. Layer 5 helps maintain the definition of the cavity and prevent tapering during the etching steps. The arrays were generated by depositing and patterning each layer of conductor and insulator. This generated a set of contact lines separated by a sheet of insulator for each electrode. The last step in the fabrication was to create the cavities and expose the microelectrodes using dry etching procedures. Details of fabrication for each layer are listed below.

Layer 1. Both sides of a single crystal silicon wafer were coated with 3 μm of $SiO_2$ at 250° C. by plasma enhanced chemical vapor deposition (PECVD, Plasmatherm, System VII). Alternatively, the $SiO_2$ could be grown on the wafer by thermal oxidation at 650° C. for 8 hours. This served as an initial passivation layer between the electrodes and semiconductive silicon wafer. Layer 1 was patterned using a lift-off procedure as reported previously, leaving the appropriate pattern as shown in FIG. 4.

Layers 2 and 4. Wafers were spin-coated with photo-sensitive polyimide (4 μm). The polyimide film was exposed to 350 nm UV light for 12 s through a Karl Suss MA-150 mask aligner to cross-link the polymer leaving a continuous, defect free-insulator film. The polyimide was cured at 150° C. for 30 min, followed by 250° C. for 30 min. The wafer was allowed to cool to room temperature before the fabrication continued.

Layer 3. 15 Å Cr and 500 Å Au were deposited by thermal evaporation. The Au thickness of this layer 132 determines the width (w) of the tubular nanoband electrode. The wafer was spin-coated with 4 μm of photoresist. The photoresist was patterned by exposure through a second Cr mask. The Au and Cr were etched simultaneously in 50% aqua regia (3 HCl: 1 $HNO_3$: 4 $H_2O$). The absence of the ultra-thin Cr layer was verified through resistance measurements with a multimeter. The remaining photoresist was stripped with acetone after the Cr/Au layer had been etched. After rinsing, the wafer was dried for 30 min at 125° C. prior to coating with polyimide.

Layer 5. A top layer 5 of Au is essential to producing cavities with well-defined, vertical walls. Thermal evaporation was used to deposit 25 Å Cr and 1500 Å Au. Photoresist was deposited and patterned according to the procedure for layer 3 using a third Cr mask. The Au and Cr were etched with aqua regia as described above. The remaining photoresist was removed with acetone and the wafer rinsed thoroughly with deionized water.

Cavity Formation. Cavities were created using standard dry etching procedures. The wafer was spin-coated with photoresist (6 μm). The photoresist was patterned by exposure to UV light through a fourth Cr mask. Layer 5 was etched with RF $Ar^+$ sputtering for 5 min and layer 3 for 2 min using a 500 V DC potential with constant pressure (30 mT) and flow (50 sccm) of Ar. The polyimide was etched using reactive ion etching (RIE) with a mixture of $O_2$ (36 sccm) and $SF_6$ (4 sccm) at 300 mT and 300 W RF power for 13 min.

Microscopy

Physical characterization of the microcavities was performed with a combination of light and electron microscopy. A light microscope (Nikon Optiphot) equipped with a calibrated eye piece was used to measure the diameter of the cavities. Scanning electron microscopy (SEM, Hitachi S-2300) was used to obtain high resolution images of the cavities and the electrodes inside the cavities. Samples were grounded through conductive carbon tabs.

Electrochemical Characterization

Electrochemical measurements were made using a BAS-100B potentiostat, equipped with a PA-1 pre-amplifier (Bio-Analytical Systems). The system was controlled through a PC with BAS-100W software. A closed three electrode cell with Pt flag auxiliary and Ag/AgCl (sat'd KCl) reference electrode was used for cyclic voltammetry (CV). The 5.0 mM $Ru(NH_3)_6Cl_3$ and 0.5 M $KNO_3$ solutions were prepared immediately before use. The $Ru(NH_3)_6Cl_3/KNO_3$ solutions were purged with Ar for 20 min to minimize interference from oxygen reduction during electrochemical measurements. Capacitance was calculated by measuring charging current from cyclic voltammograms collected in 0.5 M $KNO_3$. The potential was cycled in a region (+400 mV to +100 mV vs Ag/AgCl (sat'd KCl)) where $O_2$ would not interfere with the measurement.

Scanning Electron Microscopy.

The initial characterization of the cavity microelectrode system was performed with scanning electron microscopy (SEM). A top down view of a cavity is shown in FIG. 5. The diameter of the cavity is 53 μm. SEM shows a cavity opening that is uniform and smooth. Only the protective Au of layer 5 and the disk microelectrode (layer 1) can be seen. A "halo" can be seen in layer 5. This is caused by partial exposure of layer 5 during the second RF sputtering step resulting in partial removal (the topmost 100's of Å) of Au where the photoresist has thinned around the rim of the cavity.

Faradaic Response

Figure 18:
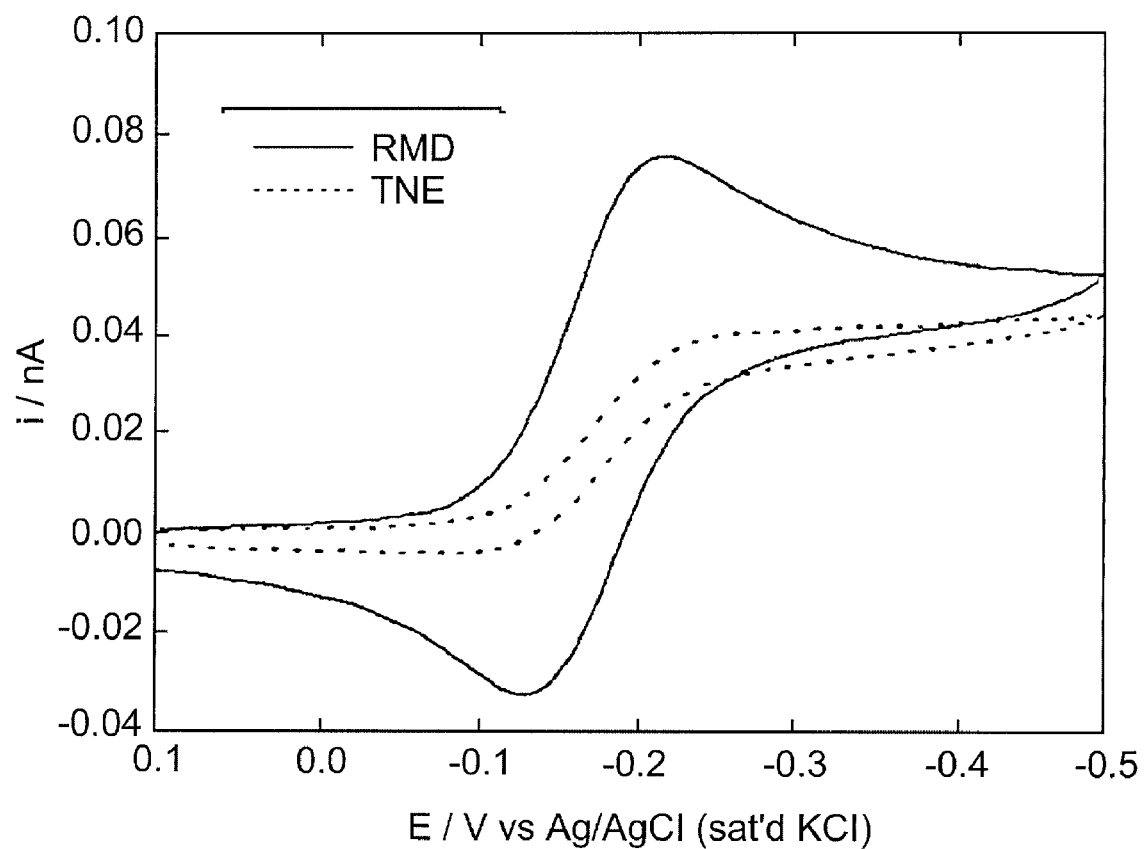
FIG. 18 shows an overlay of cyclic voltammograms (CVs) collected at the tubular nanoband electrode (TNE) and RDM inside of a single cavity.

Cyclic voltammetry was used to evaluate the electrochemical response of the recessed microdisk (RMD) and tubular nanoband electrode. FIG. 18 shows an overlay of cyclic voltammograms (CVs) collected at the tubular nanoband electrode and RDM inside of a single cavity. Band electrodes of this size should maintain pseudo-steady state behavior, while the RMDs should be peak-shaped.

The theory for both microelectrode geometries has been developed. The most commonly reported of the two geometries is the recessed disk, with models for linear and radial diffusion developed. Models describing the current at nanoband electrodes has also been discussed. Below, we compare the faradaic response at the electrodes that we have constructed to the current expected based upon the models.

Figure 19:
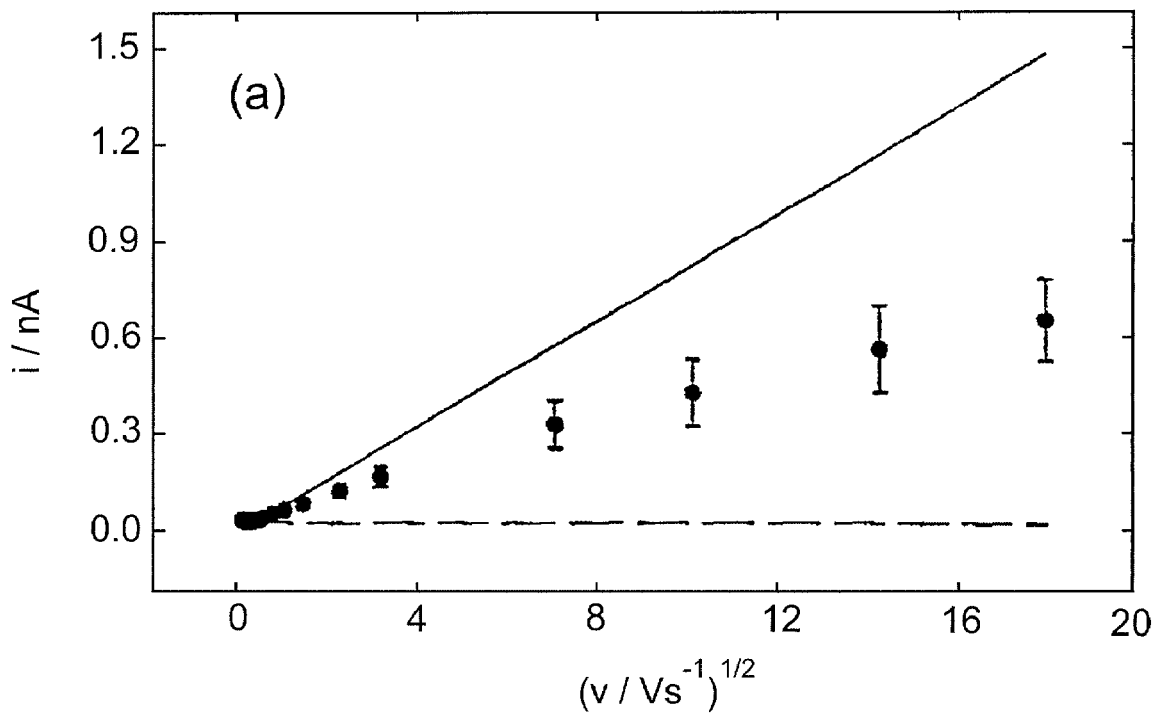
FIG. 19 shows a scan rate study from 0.01–327 $Vs^{-1}$ for RDMs in a solution of 5.0 mM $Ru(NH_3)_6^{3+}$ and 0.5 M $KNO_3$.
Figure 20:
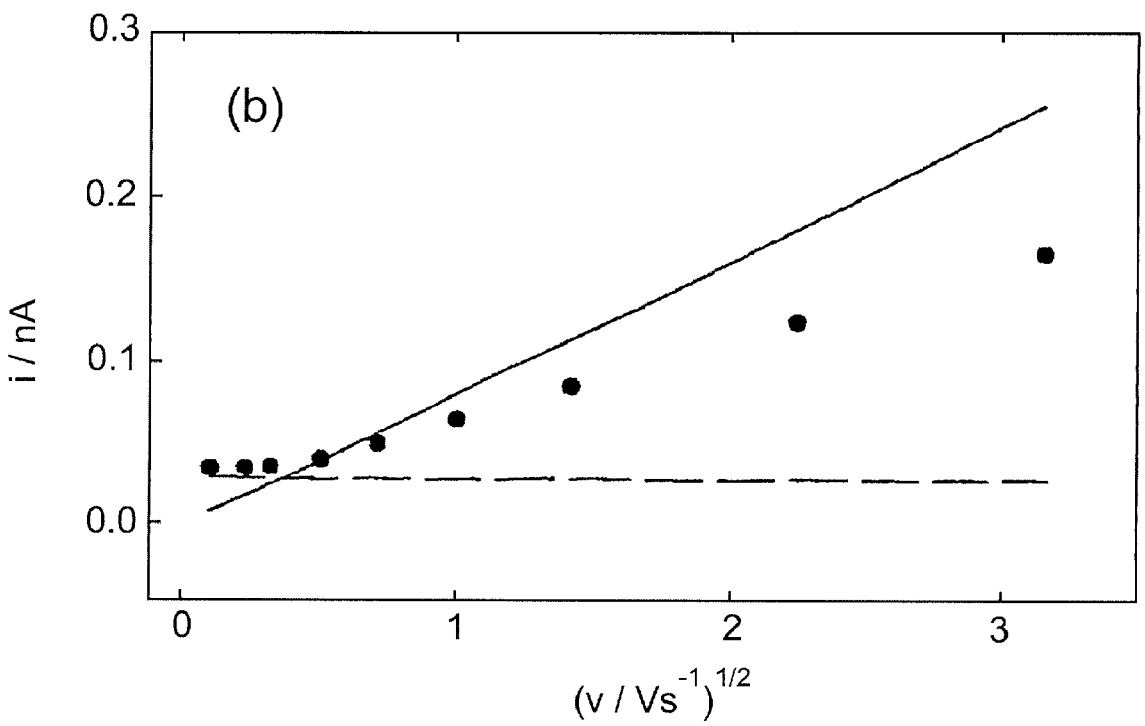
FIG. 20 is an expanded view of the region from 0.01–10 $Vs^{-1}$.

Recessed Microdisk Electrode. We have discussed the electrochemical response associated with 4 μm deep RMDs previously. In the work presented here, the RMDs are 8 μm deep (instead of 4 μm). FIG. 19 shows a scan rate study from 0.01–327 $Vs^{-1}$ for RDMs in a solution of 5.0 mM $Ru(NH_3)_6^{3+}$ and 0.5 M $KNO_3$. FIG. 20 is an expanded view of the region from 0.01–10 $Vs^{-1}$. At slow scan rates, the current follows radial diffusion theory. The experimental current (measured at 0.1 $Vs^{-1}$) is 36.65±5.10 nA is greater than the theoretical steady state current (29.32 nA) calculated for recessed disk microelectrodes. The RMDs maintain steady state behavior to 0.25 $Vs^{-1}$. At fast scan rates (>0.25 $Vs^{-1}$), the current increases, but does not follow predictions based upon linear diffusion models. For example, at 204 $Vs^{-1}$ the $i_{max}$ is 566.9±133.7 nA, which is substantially less than the theoretically calculated current, 1168 nA. This large deviation is due to uncompensated resistance in the system as reported previously.

Tubular Nanoband Electrodes

Nanoband electrodes have been studied and an equation (Equation 3) derived to predict current as a function of time for chronoamperometry.

$$i = 4nFC^*Dl/(\ln(64Dt)/w^2) \qquad (1)$$

where l is the length of the electrode, w is the width, F is Faraday's constant, D is the diffusion coefficient (7.8×10$^{-6}$ $cm^2s^{-1}$), C* is the concentration, and t is the time length of the experiment. This equation is based upon hemi-cylindrical diffusion. The length, l, is equal to the circumference ($2\pi r$) of the cavity. Unlike the steady state equation for disk microelectrodes, this equation predicts that the current will be dependent upon scan rate. Secondly, this system will never generate true steady state current because radial diffusion can only exist in two dimensions. While this equation was derived for planar band microelectrodes, it can be applied it to tubular band microelectrodes with little deviation from this theory.

Figure 21:
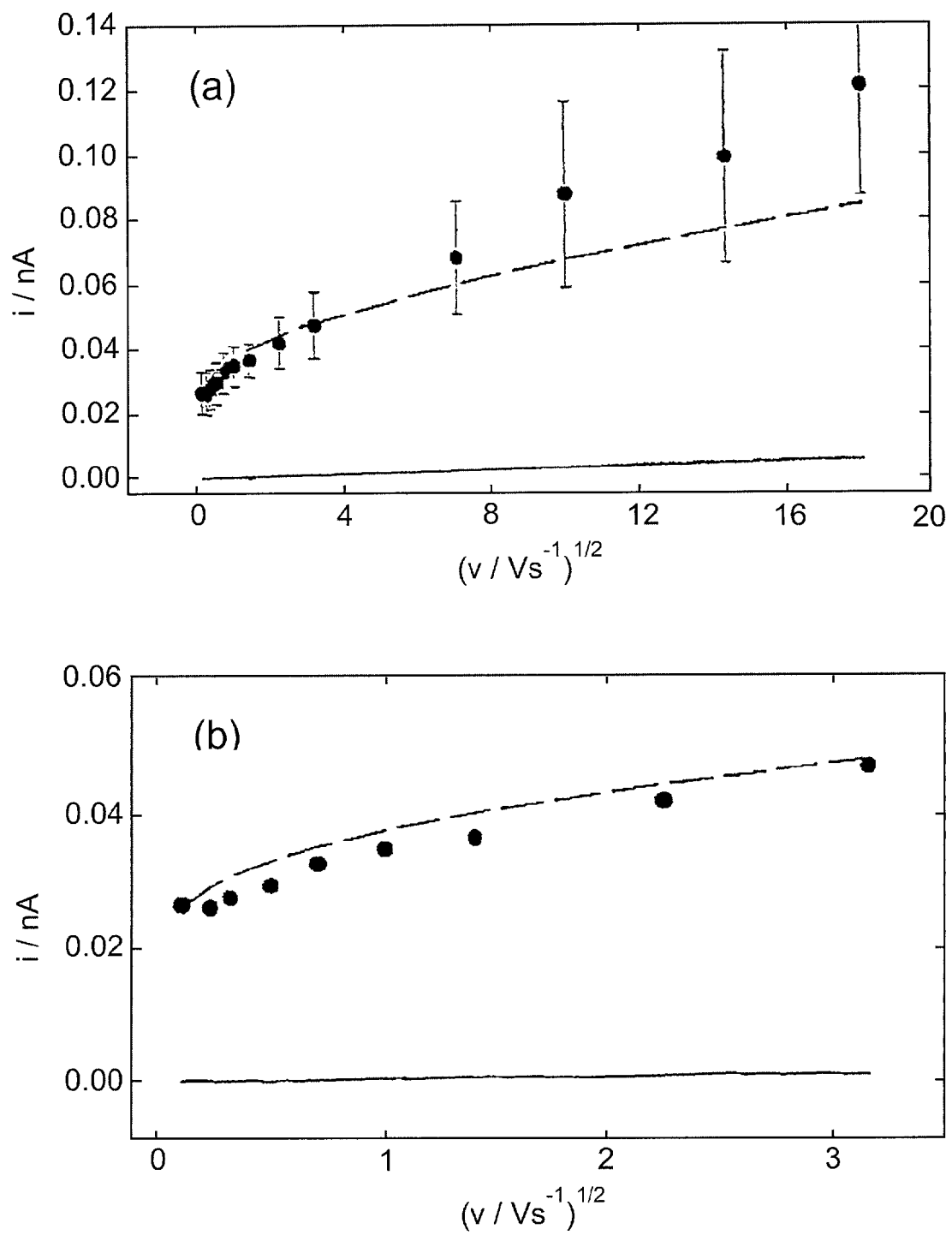
FIG. 21 shows a comparison of $i_{max}$ for the disk microelectrode to theoretical models for radial and linear diffusion.

A scan rate study was completed to compare the response of the nanoband electrodes to the theory predicted in Equation 1, and to linear diffusion models. FIG. 21 shows this comparison with 9a showing scan rates from 0.01 Vs$^{-1}$ to 327 Vs$^{-1}$, while 13b shows the region from 0.01–10 Vs$^{-1}$. First note the variation of theoretical current with scan rate as predicted. Also, the hemispherical diffusion current is larger than linear current throughout the scan rate window used in these experiments. The measured current, $i_{max}$, follows Equation 1 at slow scan rates (FIG. 21). As the scan rate increases, $i_{max}$ exceeds the predicted current. This has been reported previously for nano-band electrodes and may be the result of a small exposed edge on the electrode. It is possible that the RIE step used to etch the polyimide would leave such an edge. This edge would have a restricted diffusion layer and would not add to the current significantly at slow scan rates. At fast scan rates, the diffusion layer becomes thin enough that current from the exposed lip will add significantly to the current.

Fabrication Quality

Figure 22:
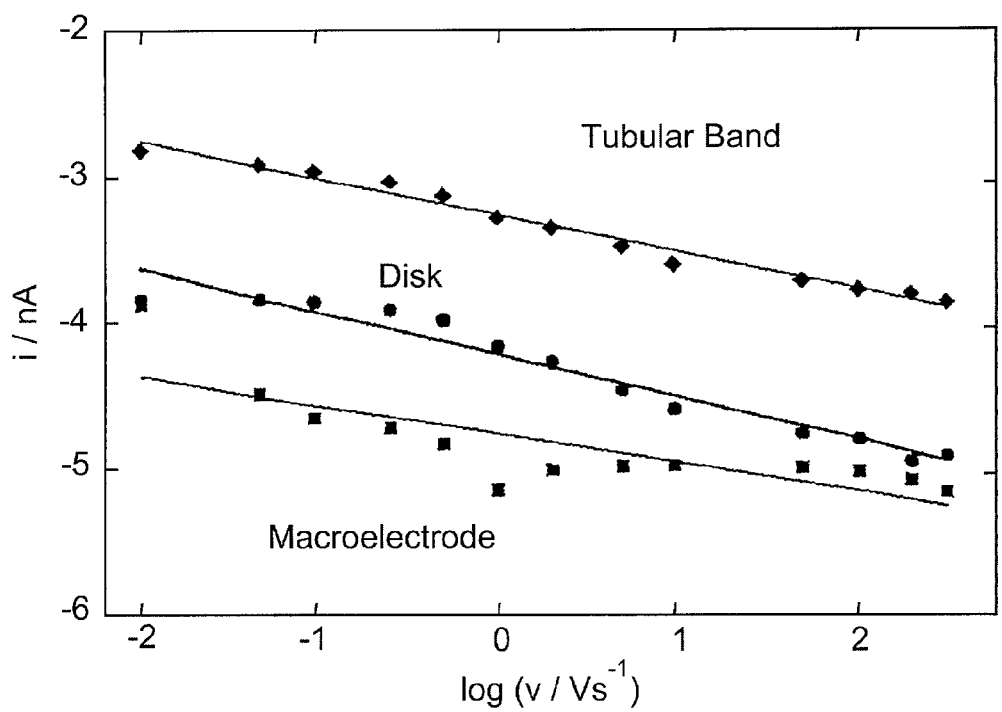
FIG. 22 shows a Log-log plot of capacitive density as function of scan rate for a macroelectrode and recessed disk microelectrode and tubular nanoband electrode.

The quality of the fabrication was evaluated from capacitance values. Capacitance was calculated from the charging current obtained from CV experiments in pure electrolyte (0.5 M KNO$_3$). The capacitance will have a large dependence upon scan rate if there is poor adhesion between the insulator and electrode or if there is cracking in the insulator around the electrode. The capacitive density was calculated and compared to a Au macroelectrode. FIG. 22 shows a log—log plot of three types of electrodes, a macro Au electrode on SiO$_2$, the RDM, and tubular nanoband electrode. Ideally, the capacitance should be independent of scan rate, however, the macroelectrode, which has no insulator, has a dependence. The scan rate dependence of both microelectrodes is close to that for the macroelectrode and is similar to that seen previously for the RDMs. This indicates that there is a good seal between the insulator and electrode and there is little or no cracking. The magnitude of the capacitance is greater for both of the microelectrodes This supports the suggestion above that more electrode area is exposed than the 500 Å wide band. If the area of the tubular nanoband was underestimated, it would make the reported capacitive density higher appear higher. This is also true of the disk electrode, however, small variations will not affect the capacitive density to the same extent.

EXAMPLE 3

All chemicals were reagent grade and used as received. Aqueous solutions were prepared with high purity deionized water (Milli-Q, model RG). A gold coin (Credit Suisse, 99.99%) and a chromium plated tungsten rod (R.D. Mathis) served as sources for thermal evaporation. Silicon wafers (5", (100)) were donated by the High Density Electronics Packaging Facility, University of Arkansas. Potassium nitrate, sulfuric acid, hydrochloric acid, silver nitrate, potassium iodide, sodium thiosulfate, nitric acid and 30% hydrogen peroxide were purchased from Fisher Scientific. Hexaamine ruthenium(lll) chloride and hydroquinone were obtained from Aldrich Chemical Co. Positive photoresist (AZ4330RS) and photoresist developer (AZ400K) were purchased from Hoechst-Celanese. Polyimide (Pyralin PI-2721, DuPont) was purchased from DuPont.

Cavity Microelectrode Construction.

The fabrication of the cavity electrode system (CES) has been described previously. In brief, the CES is made by depositing and patterning alternating layers of Au and polyimide on an oxidized Si wafer, with a total of five layers. A schematic of the CES is shown in FIG. 6. Layers 1, 3, and are Au, with a Cr adhesion layer. Layers 2 and 4 are a polymeric insulator, polyimide. After these layers have been deposited and patterned, a cavity is etched through the top 4 layers, exposing a 500 Å wide tubular nanoband electrode (TNE) and a recessed microdisk electrode (RMD). Two diameters of cavity are reported here, 13 μm and 53 μm. Both cavities are 8 μm deep.

Electrochemical Measurements

A BAS-100B potentiostat and PA-1 preamplifier controlled with BAS-1 a 100W electrochemical software were used to perform cyclic voltammetry (CV) and chronoamperometry (CA). For characterization experiments, a Pt flag auxiliary and macro Ag/AgCl (sat'd KCl) reference electrode were used to complete the three electrode system. Stirring studies involved CA and were performed on a Corning PC-320 stir plate with a ½" magnetic stir bar (Fisher Scientific) The cell volume was 40 mL and was not purged prior to CA. The rotation rate was determined by counting the rotations of the stir bar over a given time period.

Microreference Formation

Formation of a Ag/Agi pseudoreference microelectrode was accomplished following a procedure developed by Bratten et al and well known in the art. Ag was deposited for 1 s on the TNE at −0.5 V versus a Pt flag from a solution containing the complex ion [AgI$_2$]$^-$K$^+$. The complex ion was obtained in a solution of 0.1 M AgNO$_3$, 1 M KI and 0.25 mM Na$_2$S$_2$O$_3$. The Ag was oxidized in saturated KI for 0.5 s at +0.5 V versus a Pt flag. After formation of the reference electrode, the electrodes were rinsed thoroughly with deionized water, dried, and stored in a covered vial. Stability of the Ag/AgI pseudoreference was determined using cyclic voltammetry in 5.0 mM Ru(NH$_3$)$_6^{3+}$ and 0.5 M KNO$_3$ solution. The E° potential was compared to the potential determined using a macro Ag/AgCl (sat'd KCl) reference electrode.

Small Volume Analysis

The application of the CES to measurement of electroactive species in small volumes was accomplished using the Ag/AgI psuedoreference and layer 5 as the auxiliary electrode. A small volume of solution was placed on the cavity using an automatic pipette. Two solutions were tested using the CES. A 5.0 mM Ru(NH$_3$)$_6^{3+}$/0.5 M KNO$_3$ solution was used as the model system because of its well understood properties. The second analyte tested was hydroquinone. A 4.0 mM solution in 0.5 M KNO$_3$ solution buffered to pH 6.60 with 0.05 M phosphate buffer was analyzed.

Convection Studies

Convection studies were carried out using both diameters of CES. The internal reference and auxiliary electrodes were used. The protocol used for testing electrodes in convective systems has been reported previously. In brief, a solution of either 5.7 mM Ru(NH$_3$)$_6^{3+}$ and 0.5 M KNO$_3$ or 1.0 mM hydroquinone in pH 6.60 phosphate (0.05 M) buffer was placed in a cell containing a ½" magnetic stir bar. The electrodes were tested in both static solution and solution stirred at either 70 or 150 rotations per minute (rpm). Chronoamperometry (CA) was used to determine the effect of convection on faradaic current. For the $Ru(NH_3)_6^{3+}$, the potential was stepped from +0.2 V to −0.4 V vs Ag/AgI for 5 s. For the hydroquinone, the potential was stepped from +0.2 V to +0.75 V vs Ag/AgI for 5 s.

Results and Discussion

Figure 23:
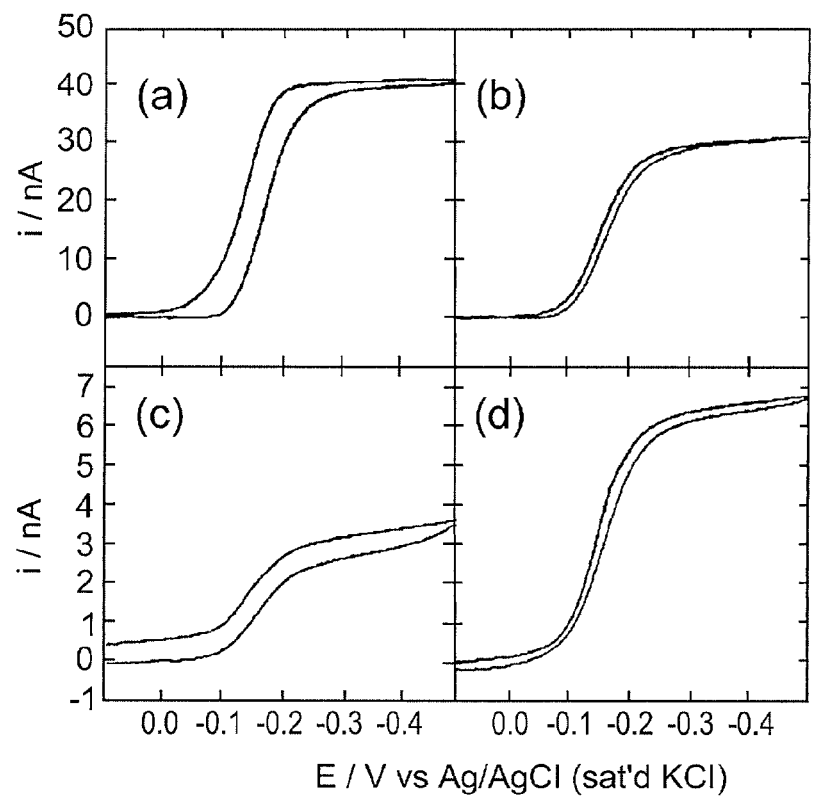
FIG. 23 compares CVs from an RMD and TNE in both 53 (a,b) and 13 μm (c,d) cavities.

The cavity electrode system (CES) was evaluated using cyclic voltammetry (CV) in $Ru(NH_3)_6^{3+}$ and 0.5 M $KNO_3$ solution. Cavities of two different diameters. 53 and 13 μm, were compared with models presented for each electrode geometry. The CES contains two electrodes, a tubular nanoband electrode (TNE) and a recessed disk microelectrode (RMD) in the configuration shown in FIG. 6. An exhaustive comparison to models for both electrodes in a 53 μm diameter cavities has already been reported. FIG. 23 compares CVs from an RMD and TNE in both 53 (a,b) and 13 μm (c,d) cavities.

At slow scan rates, the RMD in a 53 μm cavity has been shown previously to follow the model for radial diffusion to a planar microdisk electrode (PMD), while the RMD in a 13 μm cavity follows the model for radial diffusion to a RMD. The steady state current measured for the 53 μm RMD (FIG. 23) is 39.5±2.93 nA which matches closely with the predicted current (39.9 nA). The steady state current for the 13 μm RMD (FIG. 23) is 2.13±0.46 nA which is less than the predicted current (3.81 nA).

The electrochemical behavior of the TNE in a 53 μm diameter cavity has been described and found to follow models for radial diffusion to a band electrode. The comparison of a TNE to models for radial diffusion to a band electrode in a 13 μm cavity has not been reported. At 0.1 $Vs^{-1}$, the experimental current for the TNE in a 53 μm cavity is 25.8±4.2 nA, which matches with the predicted current (16.2 nA). For the TNE in a 13 μm cavity, the experimental current is 6.31±0.28 nA, which is greater than the predicted current (3.98 nA).

Formation and Stability of Ag/AgI Pseudoreference.

The ability to make accurate potential measurements in small volumes of samples requires the presence of a reference electrode. Others have reported the use of a Ag/AgI pseudoreference microelectrode for small volume measurements. Ag/AgI was deposited on the TNE and CV in 5.0 mM $Ru(NH_3)_6^{3+}$ and 0.5 M $KNO_3$ was used to characterize the system. Layer 5 was used as the auxiliary electrode to complete the electrochemical system. The standard reduction potential of AgI is −0.1519 V vs the normal hydrogen electrode (NHE) as compared to AgCl at +0.2223 V vs NHE. The experimentally determined reduction potential of $Ru(NH_3)_6^{3+}$ vs Ag/AgCl (sat'ed KCl) is −0.16±0.002 V, but −0.053±0.016 V vs the micro-Ag/AgI pseudoreference. The redox potential of $Ru(NH_3)_6^{3+}$ vs Ag/AgI, predicted by standard reduction potentials, should be +0.222 V. The 0.275 V shift in reference potential is probably due to the lack of $I^-$ in the supporting electrolyte solution.

Figure 24:
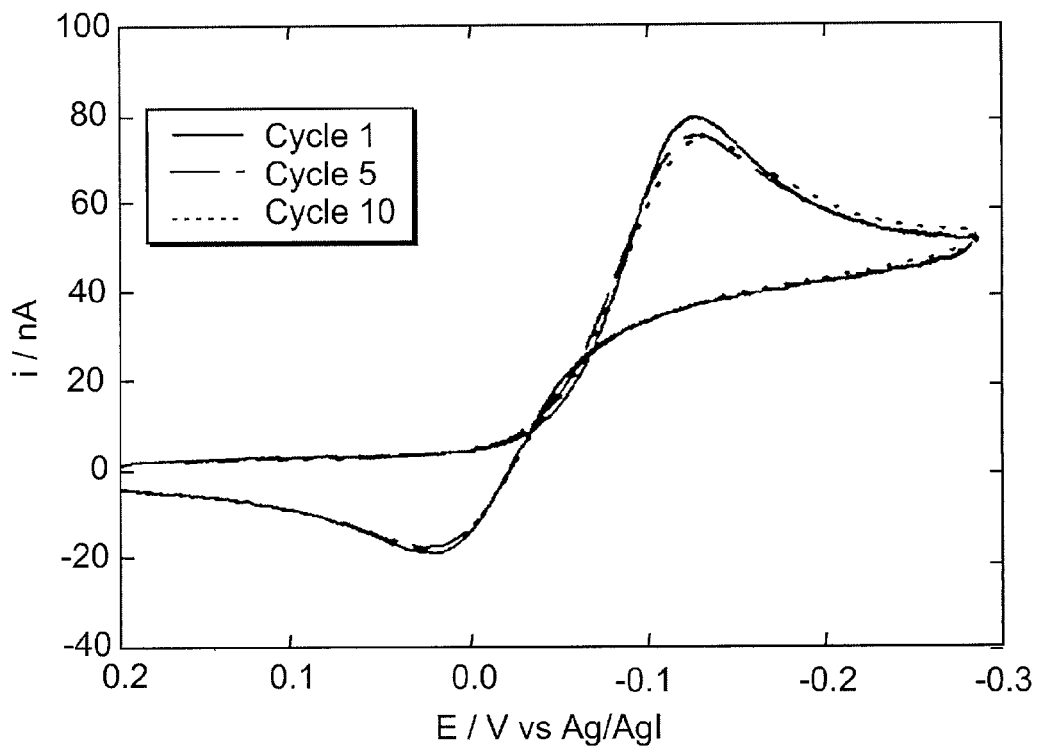
FIG. 24 shows three CVs (1, 5, and 10th cycles) collected at with a 53 um CES in 5.0 mM $Ru(NH_3)_6^{3+}$ and 0.5 M $KNO_3$ at 0.5 $Vs^{-1}$. The tubular nanoband electrode was modified to serve as a reference electrode. The disk was used as the working electrode. Bold larger #5 served as the counter-electrode.

After determining that the reference potential of the Ag/AgI pseudoreference electrode was more positive than predicted, a study was done to determine if the electrode was stable over time with multiple experiments. A simple study was done to determine the reliability of the Ag/AgI electrodes from run to run. A 53 μm cavity was placed in 5.0 mM Ru $H_3)_6^{3+}$ and 0.5 M $KNO_3$ solution and 10 CVs collected at 0.5 $Vs^{-1}$, allowing the system to go to open circuit between each cycle. The 53 μm cavity was chosen because the RMD draws more current than the TNE and therefore, the microreference in the 53 μm cavity should be less stable than the 13 μm CES. FIG. 24 shows an overlay of the first, fifth, and tenth cycles. The E° potential does not change between runs indicating that the pseudoreference electrode is stable in the absence of supporting $I^-$ ions.

Small Volume Analysis

Figure 25:
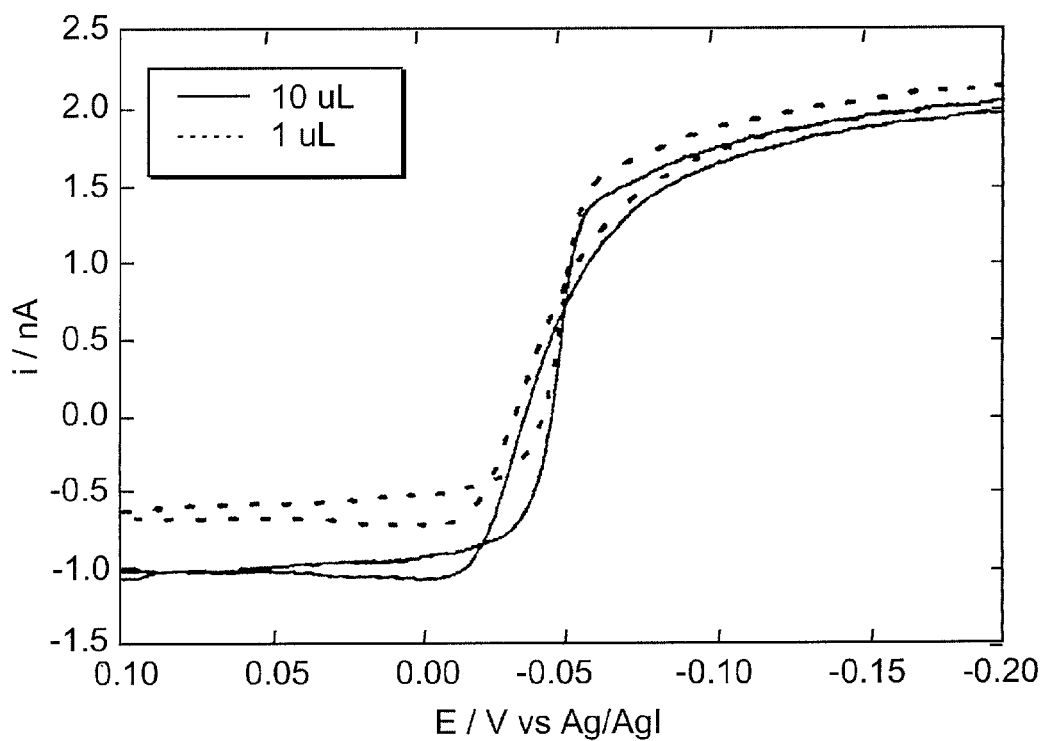
FIG. 25 shows CVs from a 13 um CES for 10 and 1 ul samples 5.0 mM $Ru(NH_3)_6^{3+}$ and 0.5 M $KNO_3$ of cycled at 0.1 $Vs^{-1}$. The self-centered electrochemistry in the small drops was carried out with electrodes defined as described in Figure caption 3.

The application of the CES to small volume analysis was first demonstrated with $Ru(NH_3)_6^{3+}$ as the analyte. FIG. 25 shows an overlay of CVs collected with an RMD in a 13 μm CES, in two different volumes, 10 and 1 μL. The response of the working electrode in these two volumes is essentially identical. The experimental current is 2.89±0.53 nA for the 10 μL sample and 2.67±0.46 nA for the 1 μL sample. E° for the 10 μL sample is −0.086±0.034 V and for the 1 μL sample is −0.123±0.063 V.

Figure 26:
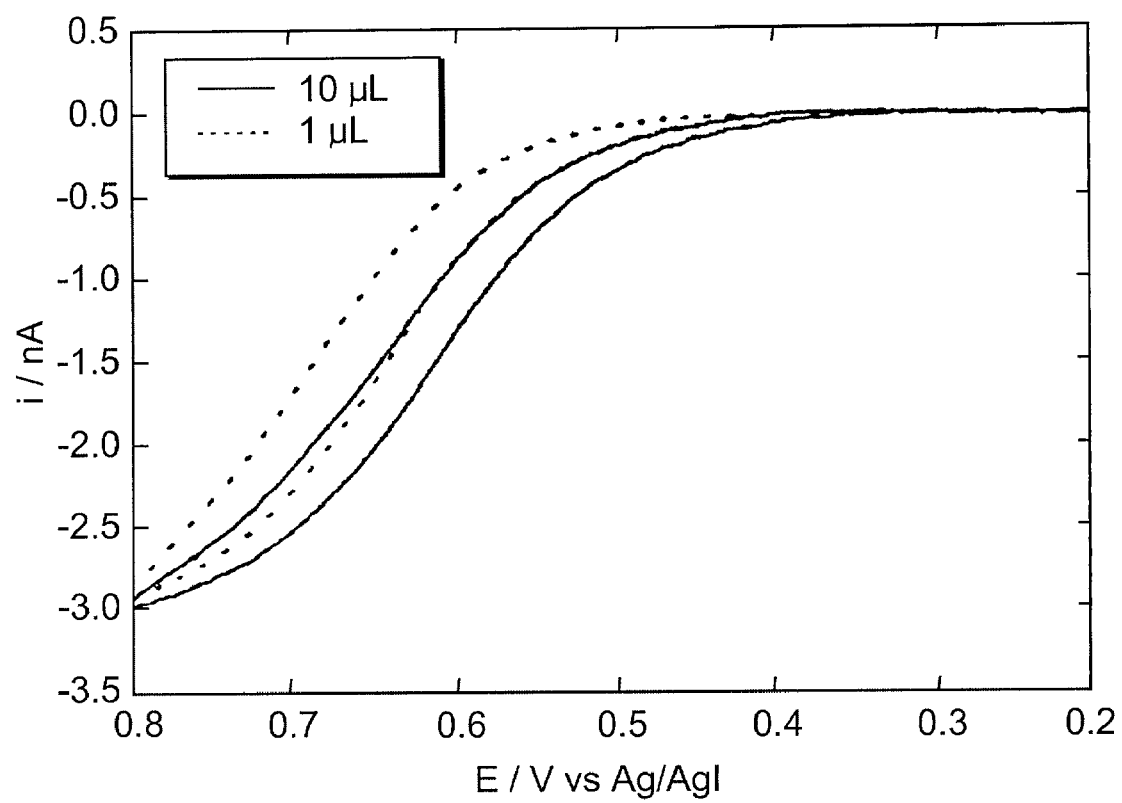
FIG. 26 shows CVs from 53 um CES for 10 and 1 uL samples of 4.0 mM hydroquinone in pH 6.60 phosphate (0.05M) buffer cycled at 0.1 $Vs^{-1}$. The self-contained electrochemistry in the small drops was carried out with electrodes defined as described in Figure caption 3.

The second small volume system tested was hydroquinone. Hyrdoquinone is a common moiety in pharmaceutical and biological compounds. The analysis of the 10 and 1 μL samples of hydroquinone is demonstrated in FIG. 26. The current for the two samples is within error, 2.91±0.84 nA for the 10 μL and 2.58±0.72 nA for the 1 μL.

Convection Studies

Both diameters of CES were tested in stirred solutions to demonstrate the advantageous nature of RMDs in convective systems. RMDs of similar diameter with a 4 μm depth have been tested previously. RMDs with a 14 μm diameter were found to provide a 4 fold improvement in signal-to-noise ratio (SNR) over planar microdisk electrodes (PMOs).

Figure 27:
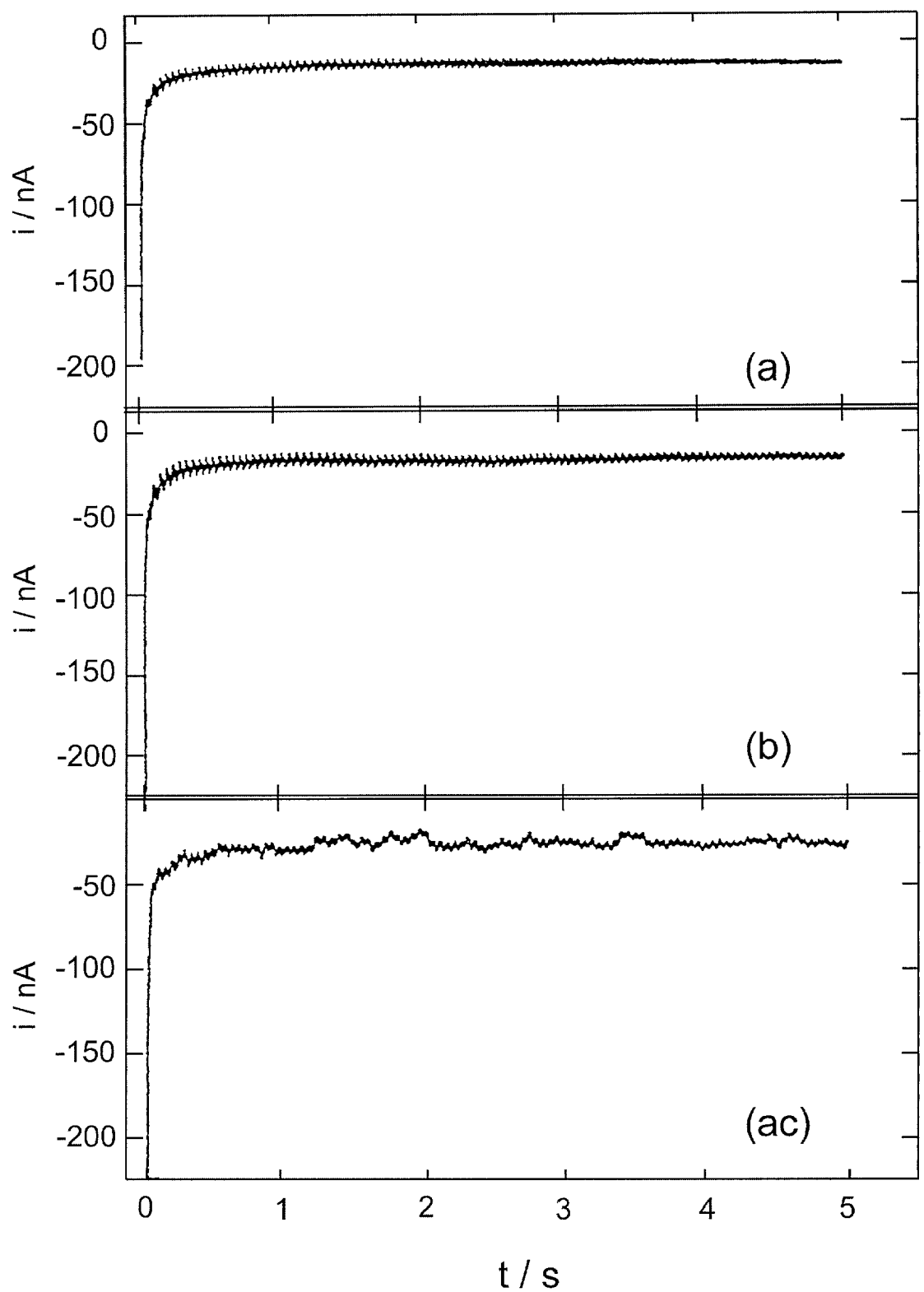
FIG. 27 shows a CA for a 53 um CES in 1.0 mM hydroquinone in 0.05 M phosphate buffer (pH 7.0). Static (a) and solutions stirred at either 70 (b) or 150 (c) rpm are shown. Electrochemistry was carried out with electrodes as defined in figure caption 3.
Figure 28:
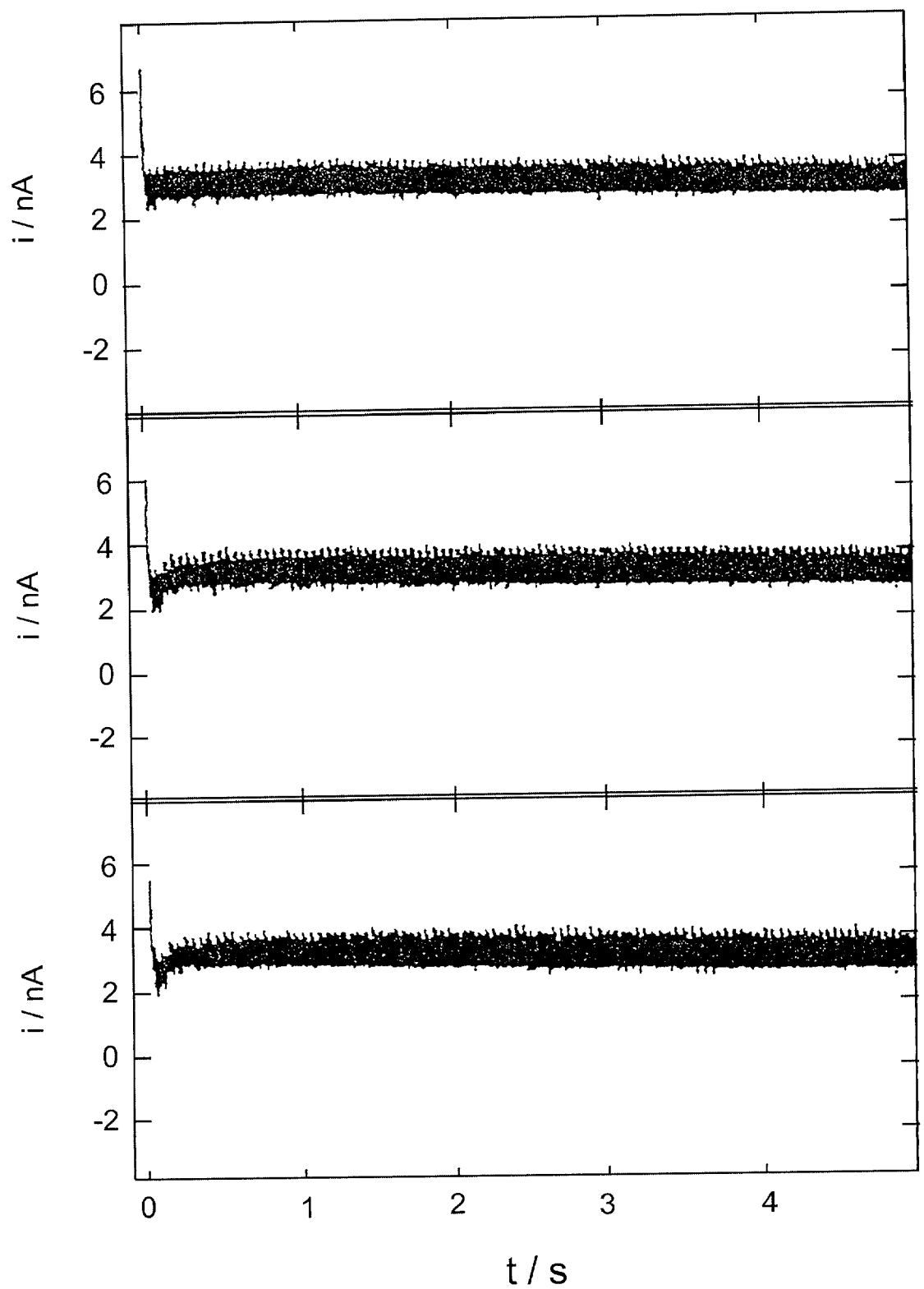
FIG. 28 shows a CA for a 13 urn CES in 5.7 mM $Ru(NH_3)_6^{3+}$ and 0.5 M $KNO_3$ solution. Static (a) and solutions stirred at either 70 (b) or 150 (c) rpm are shown. Electrochemistry was carried out with electrodes defined as in Figure caption 3.

To obtain an accurate measure of the effects of convection on the faradaic current, chronoamperometry (CA) was used. The potential was stepped from a region of non-faradaic current transfer to a region of either oxidation (hydroquinone) or reduction ($Ru(NH_3)_6^{3+}$). No data smoothing was employed and a lowpass filter with cutoff frequency of 2500 Hz was used to minimize electrical noise. FIG. 27 shows the oxidation step for hydroquinone in pH 7.0 phosphate buffer with a 53 μm CES in either static solution or solution stirred at 70 or 150 rotations-per-minute (rpm). The potential was stepped from 0.0 V to +0.6 V vs Ag/AgI for 5 s. The signal-to-noise ! atio (SNR) was calculated by first determining the steady state current between the 1st and 5th s of the potential step. The current was then divided by the standard deviation of the data during the same time duration. The noise present in the static solution is due to electrical noise. The SNR in static solution is 9.85±1.8. The SNR in a solution stirred at 70 rpm is 8.37±0.86 and at 150 rpm is 8.99±2.20. All three of these fall within error of each other. FIG. 28 shows a reduction step for $Ru(NH_3)_6^{3+}$ at a 13 μm CES for a static solution and solutions stirred at 70 and 150 rpm. The SNR was calculated following the procedure discussed above. For the static solution, the SNR is 5.30±2.7. For the solution stirred at 70 rpm, 5.60±2.44 and at 150 rpm, 5.93±2.39. Again, the SNRs are within error of each other independent of stirring.

EXAMPLE 4

Materials. Hexadecanethiol ($Cl_6SH$, Aldrich) solutions were prepared as described previously except with rigorous exclusion of airs The $C_{16}SH$ was filtered through alumina (Brockman, neutral, activity I) prior to the preparation of fresh derivatization solutions. Absolute ethanol (100%, Millennium Petrochemical), magnesium nitrate hexahydrate (99.995%, Aldrich), potassium nitrate (99.999%, Acros, N.J.), sulfuric acid (Fisher), methanol (HPLC grade, Fisher);

CHC$_3$ (HPLC grade, Fisher), and hydrogen peroxide (30%, Fisher) were used as received. Zero-grade argon and nitrogen (Air Products) were used to purge the solutions and maintain inert atmosphere in a glove bag (Instruments for Research and Industry, Cheltenham, P A) during surface derivatization. Milli-Q RG (Millipore) filtered water was used for all aqueous solutions and rinsing. Dimyristoyl phosphatidylcholine (DMPC), obtained from Avanti Polar Lipids, and gramicidin D (gD), obtained from Sigma Chemical Co., were used without further purification. Gramicidin D is a mixture of gramicidin A, B, and C, of which g.A is the major component.

Substrate Preparation. Gold substrates were prepared in an Edwards E306A thermal evaporator. Approximately 50 Å of chromium from chromium-plated tungsten rods (R.D. Mathis) was deposited as an adhesion layer, followed by 2000–2500 Å of gold (Canadian Maple Leaf, 99.9% or Credit Suisse, 99.99%) onto clean silicon wafers (Silicon Quest International). Immediately prior to modification by SAMs, gold substrates were cleaned in piranha solution, which is a 3:7 solution of 30% $H_2O_2$ and conc. $H_2SO_4$ Caution: This solution is very corrosive and must be handled with extreme care. Substrates were then rinsed thoroughly in DI water (Milli-Q RG).

Monolayer and Bilayer Preparations.

Self-assembled monolayers were formed by soaking Au substrates in derivatizing solutions of 1 mM $C_{16}SH$ or 0.1 mM gD in 1 mM $C_{16}SH$ (in ethanol) for 12 h. Electrodes were removed from solution and rinsed with AI-purged ethanol prior to performing experiments. Solution preparation and monolayer formation were performed in an Ar-purged glove-bag to minimize air-oxidation of thiolates. Samples were only exposed to air when placed in the dry, $CO_2$-free air-purged (Balston) PM-FTIRRAS chamber or when transferring to the XPS sample chamber.

Vesicle suspensions of DMPC and DMPC+gD (mole ratio: 28 DMPC to 1 gD) used for bilayer formations were prepared according to published methods. To 100 μg of dried gD (from 50 μM gD/$CH_3OH$ stock solution) 1.5 μmol DMPC (from 1 mg/10 μL DMPC/$CH_3OH$ stock), was cosolubilized along with 90 μL $CH_3OH$ and 100 μL $CHCl_3$. The solution was mixed and the resulting suspension was dried under vacuum overnight to remove the organic solvent. The dried gD/lipid mixtures were resuspended in 500 μL of Ar-purged DI water and sonicated for 2 h at 55° C. The gramicidin concentrations in vesicle solutions were determined by measuring the absorbance at 280 nm ($\epsilon$=20840 $M^{-1} cm^{-1}$) using an HP 8452A Diode Array spectrophotometer. Typical gD concentrations are from 0.9–1.4 mM. The conformation of gD in vesicles was determined by circular dichroism (CD) measurements that were obtained at room temperature using a JASCO 710A spectrometer. The characteristic positive peaks at 218–220 nm and 235–236 nm, a positive minimum at 229–230 nm and a negative ellipticity below 208 nm, indicate that gA exists in a β channel conformation in the DMPC vesicles.

Electrochemical Measurements.

The electrochemical cell consisted of a standard three-electrode system. The reference was a Ag/AgCl (saturated KCl) electrode. A platinum flag electrode served as the auxiliary electrode. Immediately prior to electrochemical experiments, solutions were purged thoroughly in a closed cell to minimize the presence of oxygen. Capacitance, C, of alkanethiol monolayers and hybrid bilayers were determined by two different methods, cyclic voltammetry and AC impedance. Cyclic voltammetry was performed using a computer-interfaced potentiostat (BioAnalytical Systems, 100B with 100W software), and was previously described. Cyclic voltammetry was performed over two different potential ranges: between 450 mV and 300 mV, and between 100 mV and –100 mV, in 0.1 M $KNO_3$ (reagent grade and 99.999%) and in 0.1 M $Mg(NO_3)_2$ (reagent grade and 99.995%). The equation $C=i_c/vA$ was used to calculate C. The $i_c$ is the cathodic or anodic charging current at a given potential (400 mV or 0.0 mV), v is the scan rate, and A is the electrode area.

AC impedance measurements were made using a EG&G PAR M273A potentiostat, M388 Electrochemical Impedance Systems software, and EG&G PAR M5210 lock-in amplifier. A sinusoidal ac signal was applied at frequencies between 10 and 64,000 Hz. Measurements were made in 0.1 M $KNO_3$ (99.999%) and 0.1 M $Mg(NO_3)_2$ (99.995%) with a 10 mV amplitude at 0.0 V vs Ag/AgCl (sat'd KCl) reference. Errors that are reported in tables or as bars in the plots represent one standard deviation.

Ellipsometry. The procedure for measuring film thickness was described previously. A Rudolph Research Model 43603 ellipsometer equipped with a 5 mW helium-neon laser light source (632.8 nm) and with a 700 angle of incidence was used to measure the monolayer and bilayer thicknesses. Six measurements were obtained at various sites on each freshly cleaned Au substrate and subsequently modified. The change in polarization state and phase change of the electric field associated with the light beam were determined. The averages of these measurements were used to calculate the film thickness on each modified substrate. A refractive index of 1.45 for hydrocarbon layers on gold was assumed. Errors that are reported in tables represent one standard deviation.

PM-FTIRRAS Spectroscopy. Infrared spectra of the modified electrodes were obtained with a Mattson Research Series polarization modulation Fourier-transform infrared spectrometer (PM-FTIRRAS). The FTIR beam was focused onto the sample at an incident angle of 77°. The beam was polarized and passed through a ZnSe Series II (Hinds) photoelastic modulator (PEM) operating at 37 kHz before reaching the sample. The reflected beam was detected using a liquid nitrogen cooled HgCdTe detector. Spectra were taken with 2 $cm^{-1}$ resolution, as indicated in figure captions. PM-FTIRRAS spectra were normalized by fitting the differential reflectance spectra to ninth order polynomial backgrounds using FitIT, curve fitting software (Mattson). After curve fitting, spectra were truncated and converted to absorbance using WmFirst macro written in-house under the specifications of Mattson.26.

X-ray Photoelectron Spectroscopy. The XPS spectra were obtained using Kratos Axis HSi spectrometer equipped with a monochromated A1Kα. source, 180° hemispherical analyzer and 5-channeltron detectors. The pressure in the analytical chamber during analysis was about $10^{-9}$ Torr. The sampling area was 0.4 mm×0.7 mm. Gold and modified-gold samples were attached to the sample holder with grounding screws. The selected regions of the spectra were normalized against the Au($4f_{7/2}$) peak height. For the gD and DMPC powder samples, a thick coating of finely ground powders of each samples were pressed into a double-sided tape and attached to a sample plate made from a Si wafer. Charge compensation with an electron flood gun was only used when analyzing the powder samples. All powder sample spectra were charge-corrected to bring the C(1s) hydrocarbon peak energy to 285.0 eV. The magnitude of the charge correction was 1.5

Characterization with ellipsometry. We have previously used ellipsometry to characterize gold surfaces that have been modified by fusion of phospholipid vesicles of DMPC with self-assembled monolayers of hexadecanethiol. Those results, which are duplicated in Table I, demonstrate that this procedure forms bilayers reproducibly. The first layer consists of a monolayer of 22.2±1.5 Å of hexadecanethiol (or 19.6±2.0 Å if formed in the presence of gD), and the second layer of phospholipids, which depending on the first layer and whether gA is present, increases the thickness by an additional 21 to 25 Å. Here, we report a more thorough analysis of these layers using ellipsometry, including exploration of the extent of vesicle physisorption and contribution of gD to total thickness of each layer. These results are also reported in Table I.

The results for the film formed on a bare gold sample that has been placed in a suspension of DMPC vesicles is 19.5±11.2 Å. The average thickness of physisorbed DMPC on gold is lower than that of a DMPC layer formed at a $C_{16}SH$ SAM. This could be due to lower coverage and less order. In addition, the large standard deviation implies that the DMPC physisorbed to gold is not uniformly distributed. Thus, it appears that the SAM is necessary to initiate reproducible and specific fusion of DMPC vesicles with the surface.

Based on surface coverage studies, the presence of gD in the thiol solution during assembly of $C_{16}SH$ onto gold appears to cause a decrease in the total $C_{16}SH$ that attaches to the surface. However, the average thickness for a SAM, formed with a gD in solution, is lower, but within error at 95% confidence of that of a pure $C_{16}SH$ SAM. To further investigate the effect of gD on the modified surfaces, we obtained additional ellipsometry results for hybrid bilayers in which gD was present during formation of only one of the two layers, either in the first layer, $gD+C_{16}SH$, or in the second layer, DMPC+gD. The thicknesses of these two types of hybrid bilayers are significantly different at the 95% confidence level. The presence of gD in the formation of the first layer has a significant impact on the structure of the bilayer. This is consistent with our previous surface coverage results and ellipsometry of the monolayers. However, when gD is present in forming both the first and second layers ($C_{16}SH+gD/DMPC+gD$) the total film thickness is the greatest of all of these combinations. This seems to indicate that DMPC+gD vesicles can fill in gaps or defects in the underlying layer better than DMPC alone. This may be due to the ability of gD to transfer from the phospholipid layer to the SAM layer, as it does in planar phospholipid bilayers.

Although ellipsometry serves as a sensitive measure of thickness, there remains unanswered questions about the composition and structure of the layers on the surface, especially in the presence of gD. In addition, the calculation of thickness from the ellipsometry measurements involves the assumption that the refractive index is the same for $C_{16}SH$, phospholipids, and gA. Thus, it is essential that other techniques be used to further elucidate the structure and verify the validity of the ellipsometry results.

Characterization with PM-FITRRAS. There has been a substantial number of structural analyses on phospholipid films performed in air by various infrared techniques. Many of these studies involve attenuated total reflectance (ATR) IR, in which the phospholipid films are deposited onto a substrate using LB-deposition methods or by casting films onto ATR plates, (not via vesicle fusion). One reason that vesicle fusion has not been used in ATR-IR is that the primer layer of alkanethiols do not covalently attach to the substrate material, which is usually Ge, ZnSe, or Si. Thin films of metal can be deposited onto the substrate material. However, the metal film must be partially transparent, and thus, may not be representative of the surface morphology of bulk metal. films. External reflectance, such as PM-FTIRRAS, eliminates such special requirements for the substrate. Thus, PM-FTIRRAS was used here to evaluate the structure and composition of the modified surfaces. Several IR bands of gA have different frequencies from DMPC and from $C_{16}SH$, so that we can monitor compositional variation in the hybrid bilayers. Table n summarizes the peak positions and assignments for PM-FTIRRAS spectra for films containing different combinations of $C_{16}SH$, gD, and DMPC, and for transmission FTIR spectra of gD and DMPC in a KBr pellet.

Figure 29:
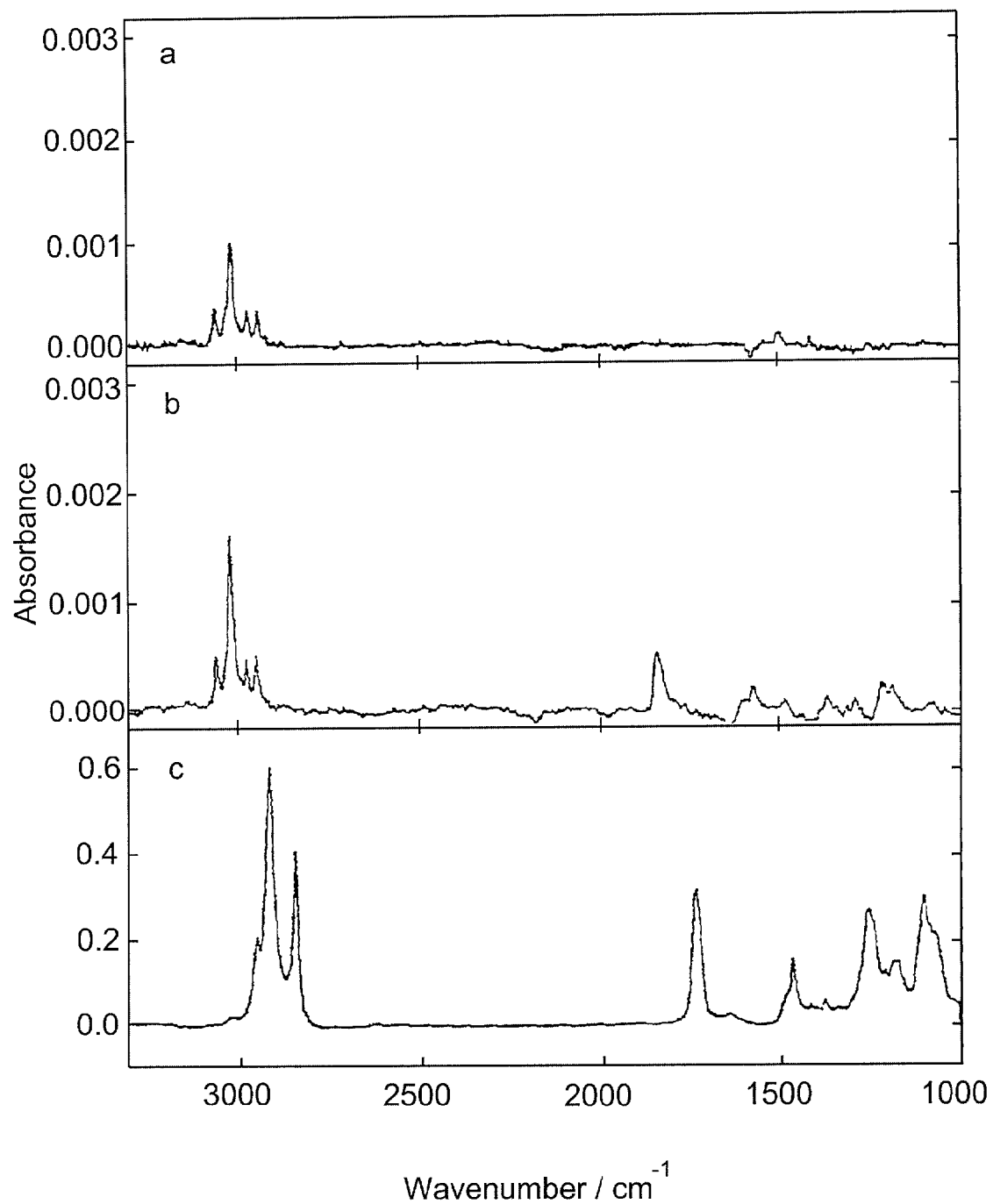
FIG. 29 shows the PM-FTIRRAS spectra of (a) ethanol-rinsed SAMs of $C_{16}$ SH and (b) $C_{16}$ SH/DMPC bilayer. Transmission IR (c) of dried DMPC in KBr pellet.

FIG. 29 shows representative IR spectra for $C_{16}SH$ SAMs, $C_{16}SH/DMPC$, bilayers, and DMPC dispersed in KBr. In the spectrum of a $C_{16}SH$ SAM (FIG. 29), the −0.0012 absorbance for the Vu $CH_2$ band is close to values reported for a monolayer coverage for $C_{16}SH$ on gold (−0.0014 AU). Other points to note in FIG. 1a are the hydrocarbon peak positions. The bands at 2964 cm$^{-1}$ and 2877 cm$^{-1}$ are assigned to the $CH_3$ asymmetric in-plane CH-stretching modes, respectively. Those at 2918 and 2850 cm$^{-1}$ are assigned to the asymmetric and symmetric $CH_2$ modes, respectively. These values are in good agreement, within ±1 cm$^{-1}$, of values reported in the literature for long-chain measurements.

The spectrum for a $C_{16}SH/DMPC$ hybrid bilayer is shown in FIG. 29. The absorbance values of the CH-stretching bands are essentially doubled from that of the SAM. We interpret this to mean that a bilayer has formed. These data are consistent with the ellipsometry measurements. The DMPC has 12 methylene carbons in the alkyl chains, not 15, and thus we would expect to see an 80% increase in the absorbance of the $CH_2$ bands, if no significant changes in orientation occur. The actual increase is 78.7±3.2% AU for the $CH_2$ $v_{as}$ band. We would expect a doubling of the $CH_3$ absorbances. The actual increase is 201.6±33.3% AU for the $CH_3$ $v_{va}$ band. Other evidence for the presence of phospholipids includes ester carbonyls at 1739 cm$^{-1}$ and the asymmetric $PO_2^-$ and symmetric $PO_2^-$ stretches at 1260 cm$^{-1}$ and 1100 cm$^{-1}$, respectively. The relative magnitude of the carbonyl stretch varies from sample to sample by ±0.0006 AU, which might be an indicator of small variations in the orientation of the head group. The only frequencies of the CH-stretching modes for the $C_{16}SH/DMPC$ bilayers that differ from those for the $C_{16}SH$ SAM are the $CH_3$ asymmetric (2962 cm$^{-1}$) and the $CH_2$ asymmetric (2917 cm$^{-1}$) modes. However, these are within the resolution of our measurements and might not be significant. In addition, if a monolayer consists of alkyl chains in all-trans configuration, the $v_{as}$ $CH_2$ band will occur at 2918 cm$^{-1}$, as compared to 2925 cm$^{-1}$ for films with a more disordered, liquid-like structure. Overall, our results indicate that the structure of the hydrocarbon chains in the DMPC layer are structurally similar to those in the SAM.

FIG. 29 shows the transmission IR spectra for DMPC in a KBr pellet for comparison. The ester carbonyl peak for DMPC in the KBr pellet (1745 cm$^{-1}$) is lower by 3 cm$^{-1}$ than that in the hybrid bilayer. Those bands for the $PO_2^-$ asymmetric stretching mode at 1252 cm$^{-1}$, and the $PO_2^-$ symmetric stretching mode, observed at 1092 cm$^{-1}$, are lower for DMPC in the KBr pellet than that in the hybrid bilayer by 8 cm$^{-1}$. The structure of DMPC in the hybrid bilayers is clearly different than in the powder form.

Figure 30:
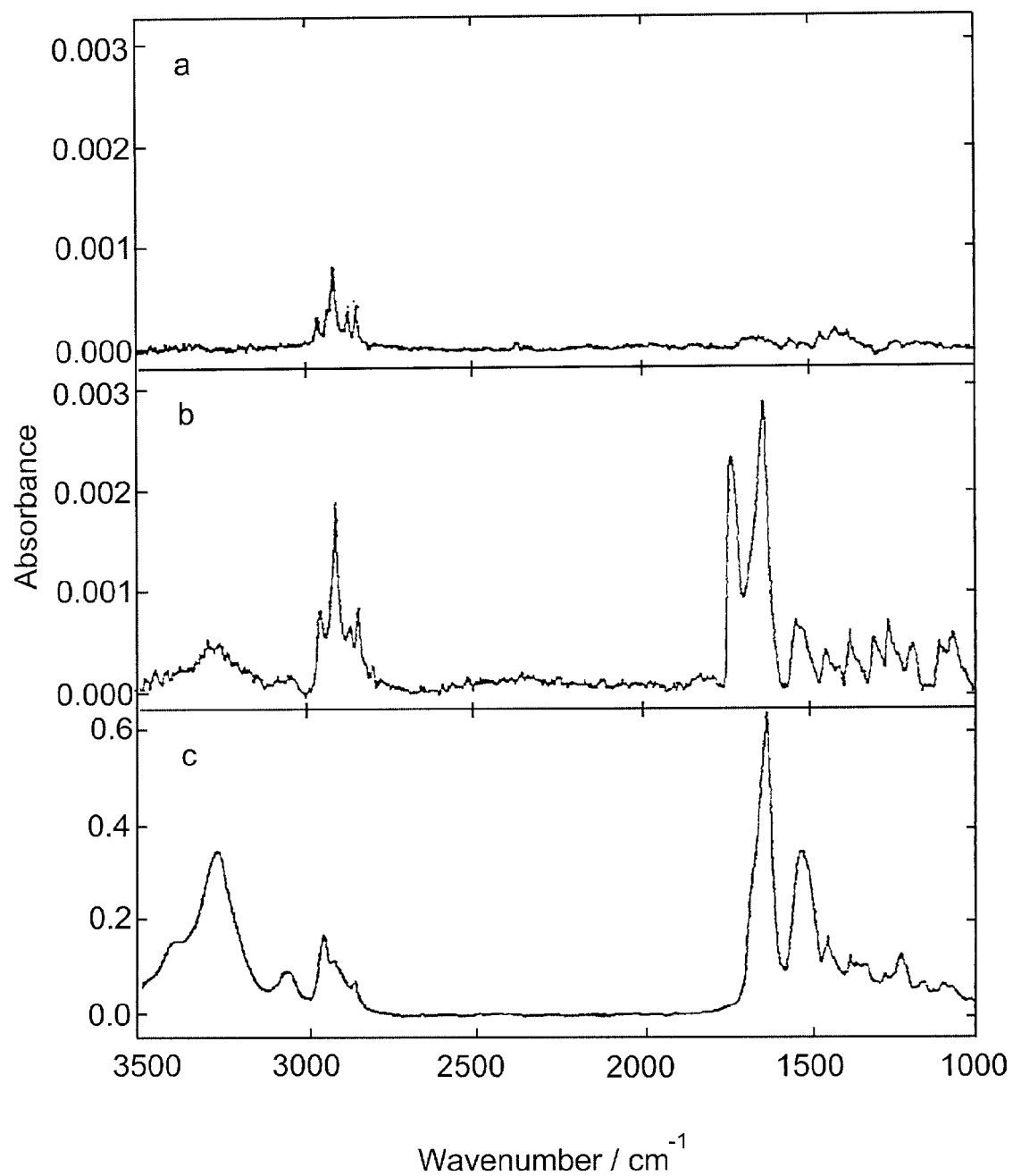
FIG. 30 shows PM-FTIRRAS spectra of (a) ethanol-rinsed SAM of $C_{16}$ SH+gD and (b) $C_{16}$ SH+gD/DMPC+gD bilayer. Transmission IR (c) of dried gD in a KBr pellet.
Figure 31:
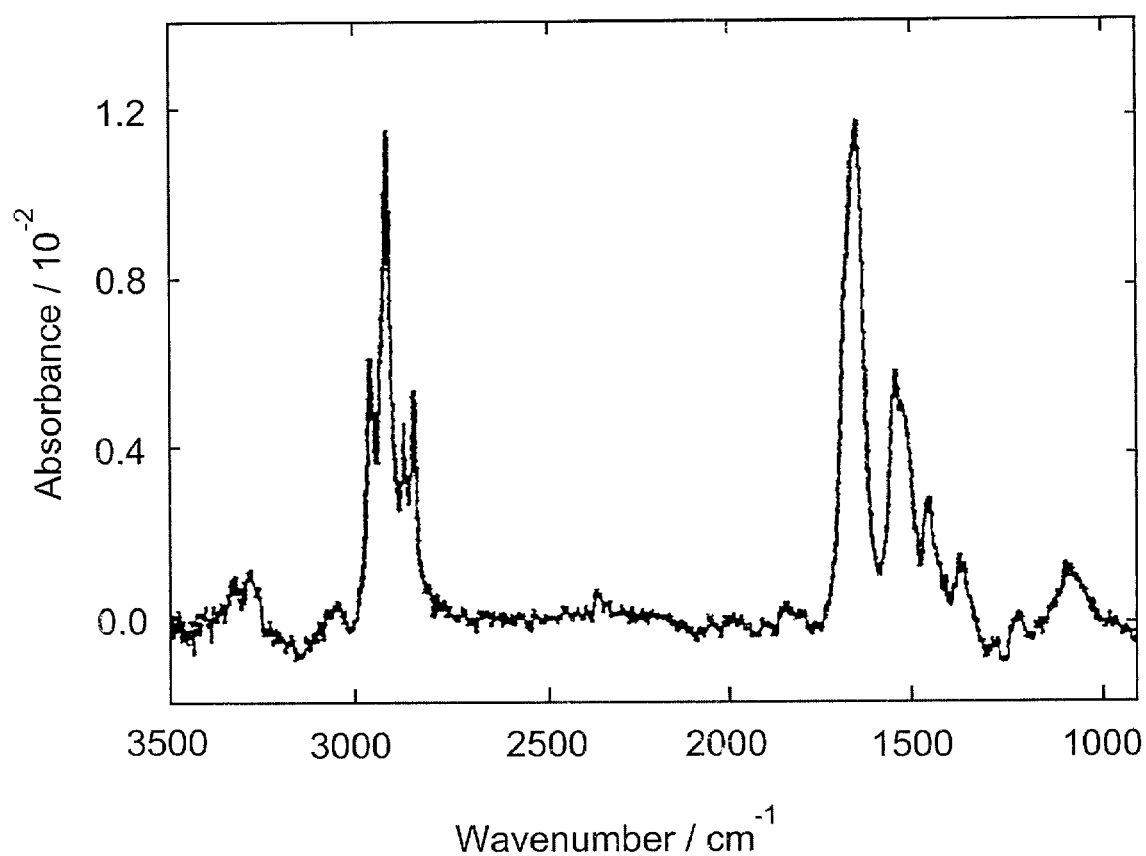
FIG. 31 shows PM-FTIRRAS spectrum of a gold substrate modified from a solution of $C_{16}$ SH+gD and water-rinsed.

FIG. 30 shows the PM-FTIRRAS spectra for the $C_{16}SH+gD$ monolayer, $C_{16}SH+gD/DMPC+gD$ bilayer, and the transmission spectrum of gD in a KBr pellet. In the spectrum for ethanol-rinsed $C_{16}SH+gD$ (FIG. 30), there are no characteristic IR bands for gA, which are the Amide I (C=O stretch) the Amide II (coupled CN stretch and NH bending), and Amide A (NH stretch) bands. Thus, it appears that gD is not present in sufficient concentrations in the SAMs formed from $C_{16}SH+gD$ to be detected. In addition, the absorbance for the CH-stretching modes is only approximately 90% of that for a SAM formed from $C_{16}SH$ alone. Interestingly, the frequencies of the CH-stretching modes are identical to those for the pure $C_{16}SH$ SAM. This indicates that any changes in the monolayer structure due to assembly in the presence of gD are not detectable with PM-FTIRRAS. We have included a PM-FTIRRAS spectrum for a film formed from a $C_{16}SH+gD$, followed by rinsing with water, instead of ethanol (FIG. 31). Our previous work demonstrated that an irreproducible number of multilayers form after a water rinse, because water does not solvate gA or $C_{16}SH$. A comparison of this spectrum and FIG. 30 provides two main points. First, it lends credibility to the fact that the IR bands for gA are easily detectable and comparable in absorbance to those of $C_{16}SH$ for films when in a 1:10 ratio (as in the solution). Second, it supports our earlier work that had only indirectly suggested that gD must be removed from the SAM during the ethanol rinse, perhaps leaving behind gaps or defects in that layer. The water rinse, however, causes multilayer formation, evidenced by a 7 times increase in the absorbance value in the CH-stretching region from that for an ethanol-rinsed sample.

FIG. 30 shows that in a bilayer of $C_{16}SH+gD/DMPC+gD$, the absorbance bands in the CH-stretching region is approximately two times the absorbance of monolayers. Gramicidin is present in the film this time, as demonstrated by the prominent Amide I peak at 1660 cm$^{-1}$, Amide II peak at 1546 cm$^{-1}$ and the weak, broad Amide A band at 3288 cm$^-$. Also present is the sharp band at 1739 cm$^-$ for the ester carbonyl of DMPC, as well as the peaks assigned to asymmetric and symmetric $PO_2^-$ stretching modes. The absorbance of ester carbonyl band is higher than that for the $C_{16}SH/DMPC$ bilayers. This may be an indication that there is some orientational change in the DMPC head group relative to the surface in the presence of gD The magnitude of this band does vary, however, from bilayer to bilayer by as much as 15% AU relative standard deviation.

FIG. 30 shows the transmission IR obtained from gD in a KBr pellet. The characteristic bands are the Amide A at 3278 cm$^{-1}$, the Amide I at 1637 cm$^{-1}$, and the Amide II 1536 cm$^{-1}$. These are lower in frequency by 10 cm$^{-1}$, 23 cm$^{-1}$, and 10 cm$^{-1}$, respectively than the corresponding bands in the hybrid bilayers containing gD. It has been reported that the frequency shift of the Amide I band suggests a change in environments around the gramicidin molecules and/or a conformational change caused by the introduction of gramicidin into the lipid layer.

XPS Analysis. XPS measurements were also used to extract information regarding surface composition for monolayers and bilayers. This method has a sensitivity of 0.01–0.3% of the elemental composition of the surface, and thus provides a complementary analysis method to IR, which is about a factor of 10 less sensitive for surface analysis. XPS spectra of O(1s), N(1s), C(1s), and S(2p) regions of $C_{16}SH$ SAMs were compared with those of SAMs formed from derivatizing solutions containing gD. The results of the O(1s), N(1s), C(1s), and S(2p) regions of each ethanol-rinsed $C_{16}SH$, ethanol-rinsed $C_{16}SH+gD$, and water-rinsed $C_{16}SH+gD$ self-assembled films are shown in FIGS. 25a, 25b, and 25c, respectively.

XPS analysis of the $C_{16}SH$ SAM (FIG. 32) shows a C(1s) at 284.9 eV for the aliphatic hydrocarbons. This value is comparable to reported literature value of 284.7 eV. Also the S(2p) doublet at 161.9 eV and 163.0 eV are consistent with reported values for thiolates bound to gold.

SAMs formed in the presence of gD, followed by an ethanol rinse, yield XPS spectra (FIG. 32) with peaks for C(1s) and S(2p) that are similar to those for the $C_{16}SH$ SAM alone. There are no new peaks for N(1s), O(1s), or for C(1s) that correspond to gD. Thus, these data are consistent with the PM-FTIRRAS data that show that the gD is removed from the surface during an ethanol rinse.

Figure 32:
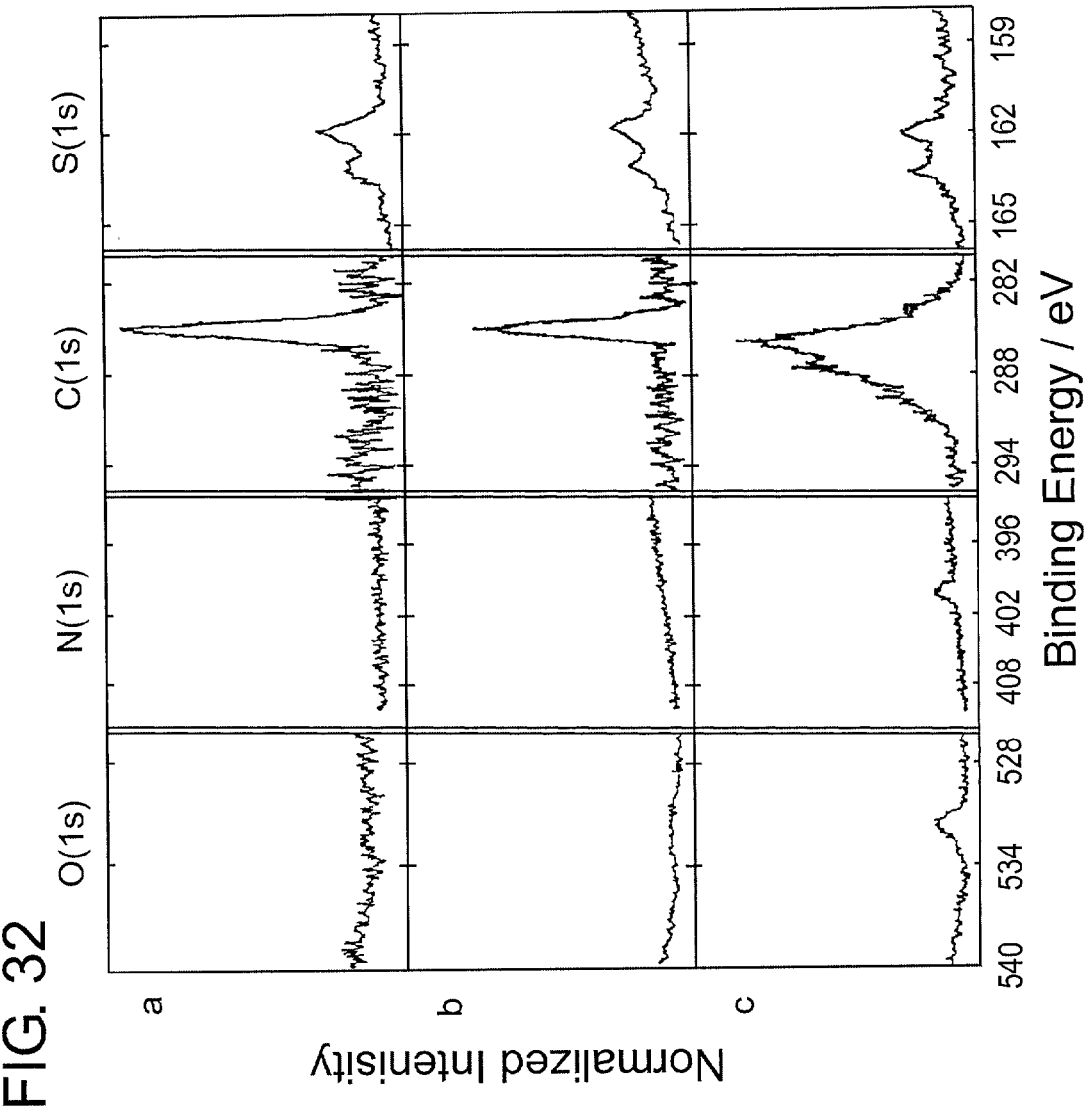
FIG. 32 shows XPS spectra of ethanol-rinsed SAMs of (a) $C_{16}$SH, (b) $C_{16}$SH+gD, and water-rinsed SAMs of (c) $C_{16}$SH+gD for O(1s), N(1s), C(1s), and S(2p).

An XPS analysis of water-rinsed samples of $C_{16}SH+gD$ is shown in FIG. 32. The strong O(1 s) peak at 531.6 eV and the N(1s) peak at 400.5 eV indicate the presence of the amide groups in gD. Also present is the shoulder at 286.6 eV representing the C(1s) emissions from the amide carbonyl groups. These results are consistent with the PM-FTIRRAS data and previous work.

Figure 33:
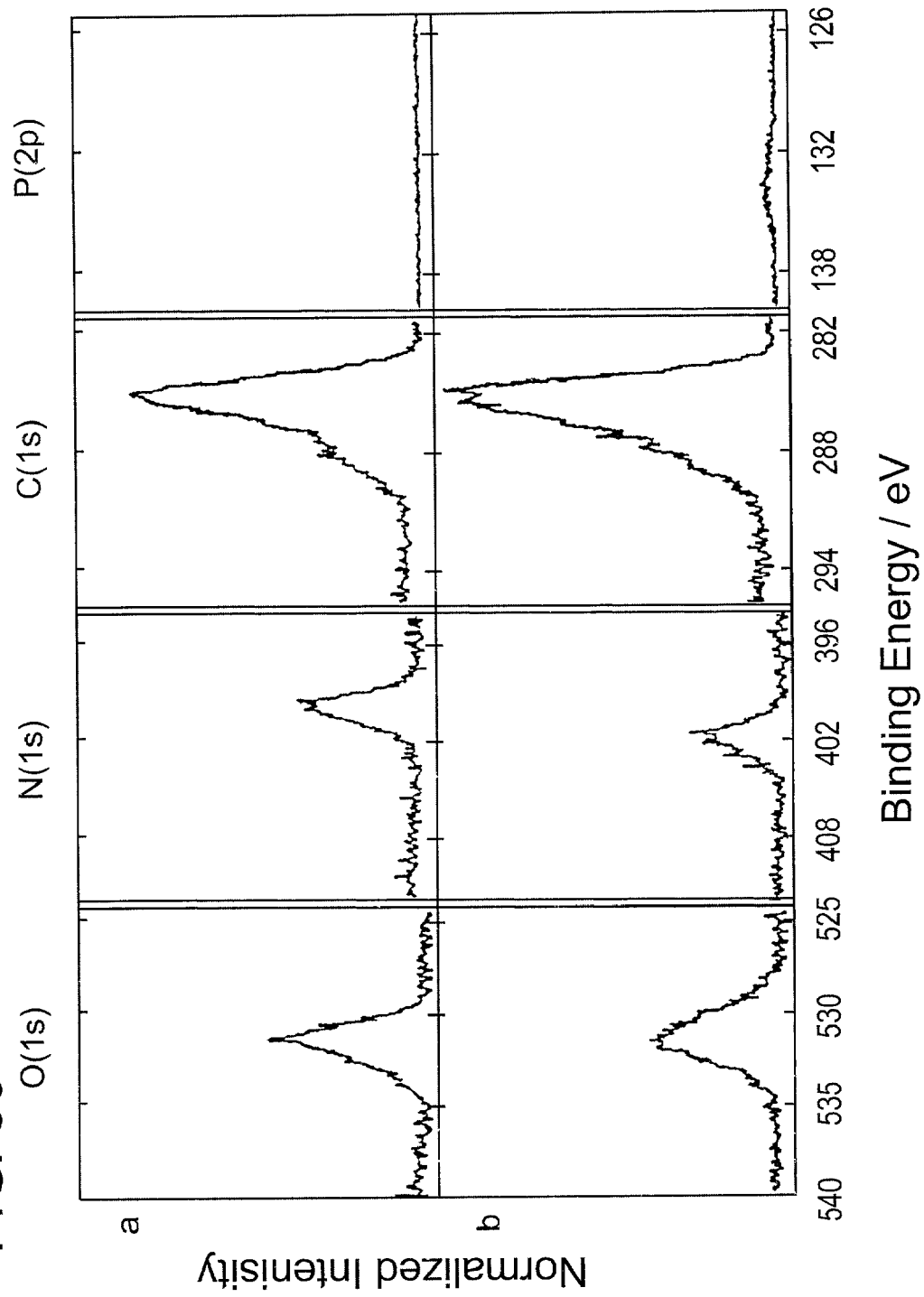
FIG. 33 shows XPS spectra of (a) gD powder and (b) DMPC powder for selected regions: of O(1s), N(1s), C(1s), and P(2p). (Charge compensation was used).

FIG. 33 shows the O(15), N(1s), and C(1s) XPS spectra of gD powder. The O(1s) peak for the gD powder appears at 531.4 eV. This value is in good agreement with values reported for poly(L-amino acids), 531.5–532.1 eV. As expected, we observe more than one C(1s) peak. The amide carbons (C—N and C=O) of the peptide backbone appear as a broad shoulder with peaks at 288.2 eV and 278.0 eV. These values are in agreement with literature values to within 0.4 eV and 0.1 eV for the C—N and C=OC(1s) regions, respectively. The N(1s) peak is observed for the amide groups in gD at 399.5 eV.

FIG. 33 shows the O(1s), N(1s), C(1s), and P(2p) XPS spectra for DMPC powder. The three chemical states that give C(1s) signals for phospholipids are those assigned to C—C and C—H at binding energy of 285.5 eV, C—O at 286.6 eV and O=C—O at 288.8 eV. The C(1s) region of the DMPC powder appears as a broad peak ranging from 286 eV to 289 eV. Also present is the N(1s) peak at 402.2 eV for the nitrogen of the lipid head group as well as the very weak and broad P(2p) peak at 134.2 eV.

The XPS analysis performed on the hybrid bilayers with and without gD yield irreproducible results. The presence of N(1s) and P(2p) peaks was sporadic from sample to sample. The PM-FTIRRAS spectra before and after XPS analysis of the same sample were identical. At this time, it is not clear why the XPS spectra are not as reproducible as the other characterization of these samples. Perhaps sample damage in the small X-ray irradiated area occurs and thus affect the XPS results, but is not sufficient to perturb enough of the sample to affect the IR analysis, which covers an area –110 times larger.

Capacitance in $KNO_3$ and $Mg(NO_3)_2$ Electrolyte. Electrochemical analysis provides additional information about the barrier properties of the modified surfaces to solution species. The capacitance at an electrode surface is highly dependent on composition of the electrolyte, solvent, nature of the electrode surface, and applied potential. There are numerous reports that draw general conclusions about SAMs and phospholipid layers based on AC impedance and other capacitance measurements such as cyclic voltammetry in simple electrolytes. However, many reports do not provide supporting analyses from other techniques. Here, we correlate our spectroscopic data to capacitance determinations and compare to the conclusions found in the literature. Potassium- and magnesium-containing nitrate salts were chosen to evaluate the relative permeation of mono- and dications through the films, respectively. Capacitance values were obtained by CV and ac impedance and are reported in Tables III and IV.

Overall, the capacitance data seem to be consistent with the spectroscopic data. Specifically, the decrease in capacitance from monolayers to bilayers is close to 50%, which is expected if the bilayer is double the thickness of the monolayer and if the molecules in the two layers are identical. There is a more dramatic change in capacitance for the gD-containing films (46% for $KNO_3$ and 54% for $Mg(NO_3)_2$ than for those without gD (40% for $KNO_3$ and 48% for $Mg(NO_3)_2$. This is consistent with ellipsometry that shows a 128% and 98% increase in thickness for bilayers with and without gD, respectively. Likewise, when IR indicates lower coverage of CH-containing molecules, the capacitance in $KNO_3$ increases, such as when comparing SAMs of $C_{16}SH$ to SAMs of $C_{16}SH+gD$ or when comparing bilayers of $C_{16}SH/DMPC$ to bilayers of $C_{16}SH+gD/DMPC+gD$.

The type of electrolyte can play a significant role. If spectroscopic analysis are unavailable, interpretation of capacitance may be difficult. However, determination of capacitance in different electrolytes can provide valuable insights into film structure and composition. For example, the relative capacitance trends in $Mg(NO_3)_2$, for films with and without gD, are opposite those of $KNO_3$ Possible reasons for this are described further below.

Capacitance values determined from the charging current in CV (100 mV/s), measured at 0.4 V, are shown in Table III for all versions of the modified electrodes. There are two sets of data. The first set of values was obtained in reagent grade 0.1 M $KNO_3$ and 0.1 M $Mg(NO_3)_2$ (from $Mg(NO_3)_2 \cdot 6 H_2O$) and for samples which were not protected from air during transfers to and from the electrochemical cell. These were reported previously. It has been suggested that SAMs air oxidize upon exposure to air, which may change the capacitance of the layers. Also, the impurities in the electrolytes used previously, and in particular those of the Mg-containing salt, may have led to capacitance values that could not be accurately predicted. Thus, a second set of capacitance values (Table III) were obtained in solutions prepared from higher purity salts, $KNO_3$ (99.999%) and $Mg(NO_3)_2 \cdot 6 H2O$ (99.995%), and for which samples had not been exposed to air at any point in the preparation or electrochemical analysis steps.

The first and second set of C values obtained in KNO3 are within error for a given film composition. In both cases, higher capacitance is obtained in $KNO_3$ when gD is present in the derivatizing solutions to form the monolayers (34–38%) and bilayers (14–24%). In $Mg(NO_3)_2$ there is a decrease in capacitance from $C_{16}$ SH SAMs to $C_{16}SH+gD$ SAMs. That decrease is 22% and 20% for the first set and second set, respectively. For bilayers, the decrease in capacitance in Mg(NO3)2 when gD is present is 26% and 17%, respectively. Although the absolute capacitance values for the Mg(NO3h electrolyte in the second set are lower than for the first set, the trends observed in the absence and presence of gD are similar and reproducible.

The monolayer-modified samples show a similar trend in capacitance with gD as the bilayers. Yet, it is known, based on the spectroscopic evidence described above, that the C16SH+gD monolayer does not contain significant amounts of gD. Thus, for that modified surface, one cannot propose that the selective permeation is based on ion channel conformation. Also, such structural and compositional changes may contribute to the selective-ion effect for bilayers with and without gD. Based on these results, it appears that the ion-selectivity of the films with gD are governed by film composition, not ion-channel conformation.

The capacitance values in Table III are higher than those reported by others for SAM and phospholipid modified electrodes. The capacitance for the $C_{16}SH/DMPC$ bilayer in purified 0.1 M $KNO_3$ is about 2.6 times greater than those reported for $C_{18}SH/POPC$ bilayers on Au in 0.010 M KCl and –1.6 times greater than for $C_{10}SH/POPC$ bilayer in TBS.

We believe that those differences are due to the manner in which the capacitance was determined, not because of large differences in sample preparation. We investigated this further by comparing the results from other electrochemical techniques for the monolayer-modified surfaces ($C_{16}SH$ and $C_{16}SH+gD$). The capacitance values from these experiments are reported in Table IV. The capacitances for $C_{16}SH$ and $C_{16}SH+gD$ SAMs using CV at 0.0 V were 49–53% lower in 0.1 M $KNO_3$ and 46–47% lower in 0.1 M $Mg(NO_3)_2$ than results obtained at 0.4 V. For example, the capacitance of $C_{16}SH$ SAM at 0.0 V in 0.1 M $KNO_3$ (99.999%) electrolyte was $1.53=0.06$ $\mu F/cm^2$, but is $3.05=0.07$ $\mu F/cm^2$ at 0.4 V. However, our value for CV at 0.0 V is still higher than Plant, reports the capacitance for $C_{16}SH$ monolayer in 0.010 M KCl is about 1.12 $\mu F/cm^2$ using ac impedance at 0.0 V.9 We also performed ac impedance at 0.0 V. The capacitance the $C_{16}SH$ SAMs ($0.90=0.08 \mu F/cm^2$) is in good agreement with those previously reported by others using the same technique.

The results from different electrochemical methods indicate that capacitance determinations are very technique-dependent. Because the $C_{16}SH$ SAM-capacitance that we obtained by ac impedance is comparable to literature values, we conclude that our sample preparation procedure must be valid. We have only obtained a complete set of capacitance data for both monolayers and bilayers using CV at 0.4 V (Table III). However, SAMs prepared from solutions of $C_{16}SH+gD$ exhibit the same trends in capacitance when compared to pure $C_{16}SH$ SAMs, regardless of the technique (see Table IV). Thus, although the absolute values are higher than those determined by other electrochemical methods, the relative values in Table III show the same trends.

EXAMPLE 5

Chemicals and Materials

A gold coin (Canadian Maple Leaf, 99.9%) and chromium-plated tungsten rods (R.D. Mathis) served as sources for thermal evaporation. Silicon wafers were obtained from Silicon Quest Internat (Santa Clara, Calif.). Absolute ethanol was obtained from Ultra Scientific. Hexadecanethiol ($C_{16}SH$), methanol, acetonitrile, chloroform, tetrabutylammonium hexafluorophosphate ($TBAPF_6$, 96%), silver nitrate, and lead nitrate were obtained from Aldrich Chemical Co. The $TBAPF_6$ was recrystallized from ethanol and dried over night in vacuum at 107° C. (22) Magnesium nitrate hexahydrate, potassium nitrate, potassium hydroxide, sulfuric acid, lithium perchlorate, and 30% hydrogen peroxide were obtained from Fisher Scientific. Gramicidin D (gD) was obtained from Sigma Chemical Co. Dimyristoyl phosphatidylcholine (DMPC) was obtained from Avanti Polar Lipids (Alabaster, Ala.). The 10-(ferrocenylcarbonyl)-decanethiol, $FcCOC_{10}SH$, was synthesized and purified as described in Everett et al. Purified gA was donated by Roger E. Koeppe, II, and his research group (University of Arkansas, Fayetteville, Ark.). Deionized (DI) water used was purified with a Milli-Q system. Unless otherwise specified, chemicals were used as received.

Fabrication of Working Electrodes

Silicon wafer substrates were cleaned for approximately 15–20 minutes in a solution of 7:3 (v/v) concentrated $H_2SO_4$ and 30% $H_2O_2$. respectively, and rinsed thoroughly with DI water. The wafers were dried under $N_2$ and oven-dried at 100° C. for 10 min. About 100 Å of chromium was thermally evaporated as an adhesion layer followed by 1500–2500 Å of gold using an Edwards E306A Coating System.

Derivatizing Solutions and Monolayer Preparation

Solutions of 1 mM $C_{16}SH$ were prepared by first filtering $C_{16}SH$ through a plug of alumina, followed by diluting with 100% ethanol. Solutions of 1 mM $FcCOC_{10}SH$ were prepared in 100% ethanol. Immediately after preparation, solutions were purged for 12–25 minutes with and stored under Ar to minimize disulfide formation. Gramicidin-containing organothiol solutions ($C_{16}SH$+gD or $FcCOC_{10}SH$+gD) were prepared prior to use by dissolving gD or purified gA in the organothiol solution. Unless otherwise specified, derivatizing solutions consisted of a mole ratio of 10 organothiol to 1 gD. Gramicidin D is a mixture of gA. gB and gC. in which gA is a major component of the mixture (~85%). Because similar results were obtained for both gD and purified gA, we do not distinguish between gA and gD in this paper.

SAMs were formed by soaking gold electrodes in derivatizing solutions for about 24 h under Ar. Electrodes were removed from solution and rinsed with water or ethanol prior to performing experiments.

Vesicles and Bilayer Preparation

Solutions of vesicles of DMPC+gD (mole ratio: 28 DMPC to 1 gD) were prepared. Lipid (140 µmol–50 µmol) was added from stock methanol solution to dried gD (10 nmol–1 µmol). The total volume was brought to 200 µL by the addition of a 50:50 mixture of methanol and chloroform.

The solution was mixed and the resulting suspension was dried under vacuum overnight to remove the organic solvent. The dried gramicidin/lipid mixtures were resuspended in 500 µL of Ar-purged water and sonicated for 2 h at 55° C. using a Branson W-185 cell disrupter (power level 5) fitted with a Model431-A cup horn accessory. Samples were centrifuged in an Eppendorf Centrifuge 5415C at 12,500 rpm for 5 min at room temperature. The gramicidin concentrations in the supernatant were determined by measuring the absorbance at 280 nm using a HP 8452A Diode Array spectrophotometer. Solutions of vesicles of DMPC alone (no gD) were prepared as above. The conformation of gD in vesicles was determined by circular dichroism (CD) measurements that were obtained at room temperature using a JASCO 710A spectrometer.

To form hybrid bilayers, electrodes were first modified with self-assembly from $C_{16}SH$ and $C_{16}SH$+gD solutions and rinsed with ethanol. The SAM-coated electrodes were soaked in aqueous suspensions of either DMPC or DMPC+ gD vesicles for about 24 h and rinsed with water. Hybrid bilayers were prepared immediately prior to use.

Our supported hybrid bilayers consist of a first layer that is a SAM of hexadecanethiol and a second layer formed from vesicles of DMPC that are suspended in an aqueous Solution. The advantage of these structures is that they better mimic biomembranes than a monolayer. More importantly, the vesicles provide a convenient way to deliver membrane proteins to a surface. Unbound vesicles can be rinsed away with water. Therefore, the proteins which are only slightly soluble in water and which are incorporated into the film will not be rinsed away. DMPC was chosen because it is known to form vesicles in which gA is in a channel forming configuration. Each DMPC consists of two butadecyl chains and a hydrophilic head group containing ammonium and phosphate moieties.

Supported Hybrid Bilayers Formed from SAMs and Vesicles

Figure 34:
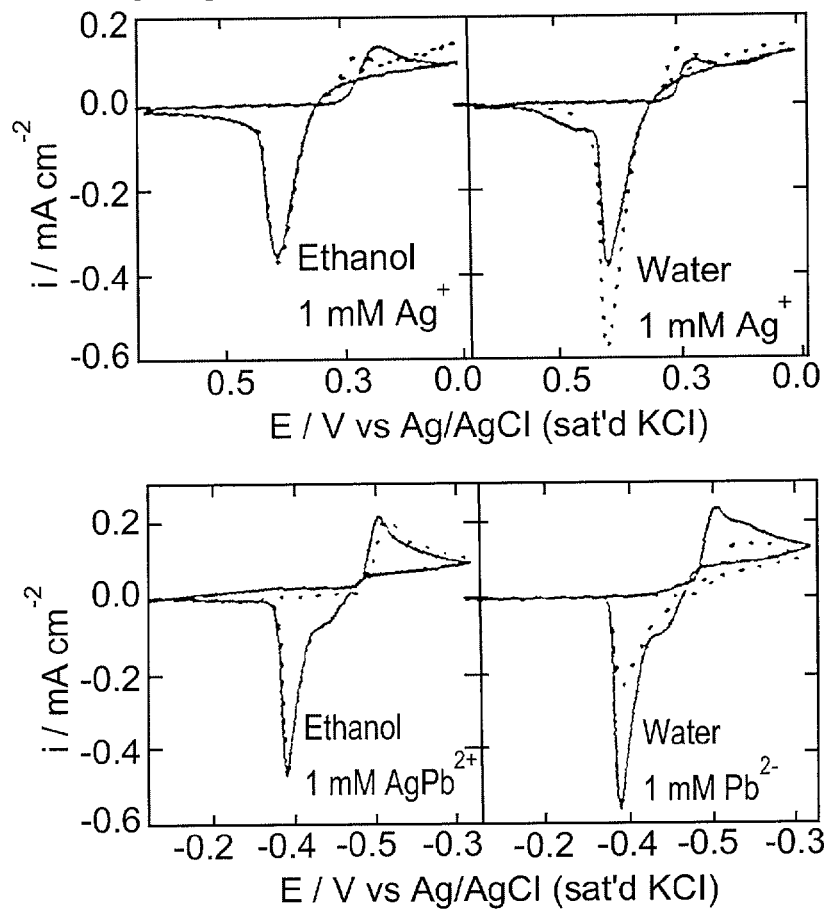
FIG. 34 shows CV of $Ag^+$ and $Pb^{2+}$ at electrodes modified with hexadecanethiol, with and without gD, and rinsed with ethanol or water.
Figure 35:
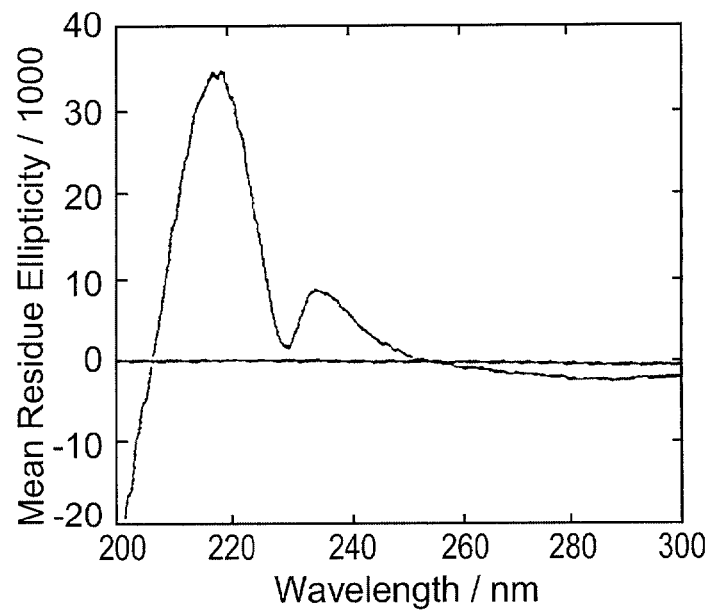
FIG. 35 shows a CD spectra indicating that gA in the vesicles is in the β channel conformation.

Bilayers were constructed by allowing phospholipid vesicles to assemble from an aqueous suspension onto ethanol-rinsed, SAM-modified electrodes (FIG. 34). CD spectra indicate that gA in the vesicles is in the β channel conformation (FIG. 34). The β channel conformation gives a unique CD spectrum which is characterized by positive peaks at 218–220 nm and 235–236 nm, a positive minimum at 229–230 nm and a negative ellipticity below 208 nm (FIG. 35). A water rinse rather than an organic solvent rinse, flushes away free vesicles but will not remove gD that has partitioned from vesicles into surface-confined films.

Film Thickness

Ellipsometry results for monolayers and bilayers are shown in the thickness of films of $C_{16}SH$/DMPC is 21–25 Å higher than for $C_{16}SH$ alone, essentially twice that of monolayers. The layer of DMPC should have a thickness of about 19.6 Å. The experimental C value for DMPC is slightly larger than the predicted value. This difference might narrow if a more accurate refractive index were used. The small deviation from the predicted value may be due to minute differences between the structure of supported hybrid bilayers and planar phospholipid bilayers. The thickness of films of $C_{16}SH$+gD/DMPC+gD is within error of those without gD. The gD must not cause a large enough change in film structure in either monolayers or bilayers to affect thickness.

These data show more convincingly than the capacitance data that the DMPC-formed films are indeed bilayers, and not disorganized films composed of multiple layers of organothiols and phospholipids.

Electrochemical response to $Fe(CN)_6^{3-}$.

Figure 14:
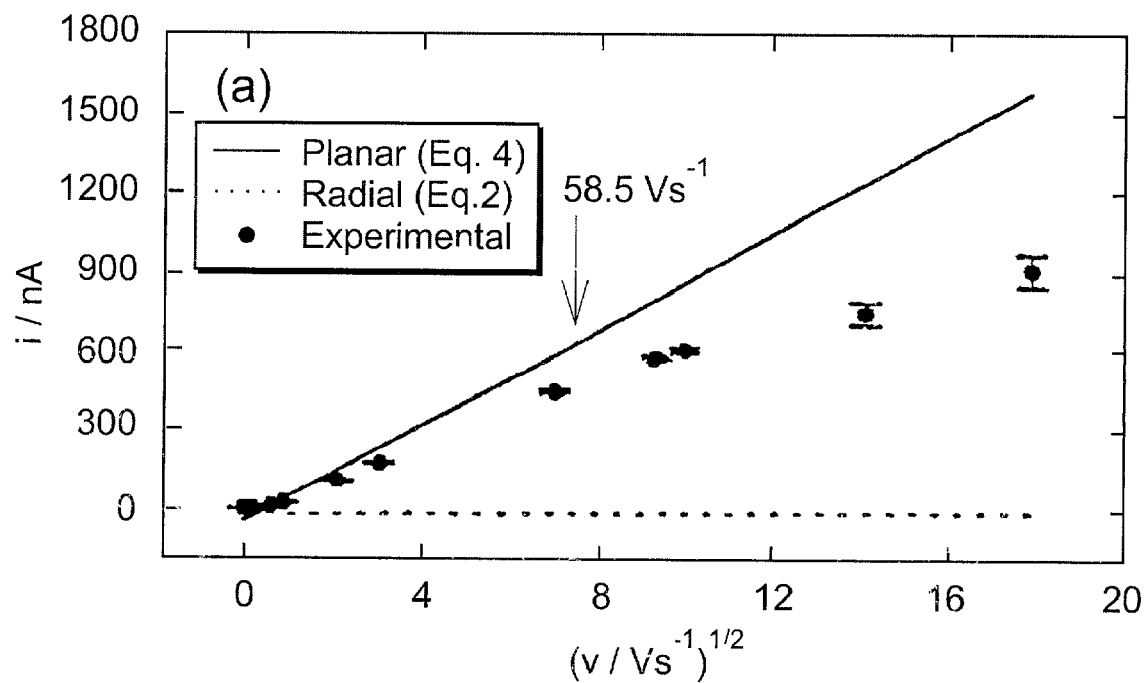
FIG. 14 shows a comparison of maximum current taken from CV in 5 mM $Ru(NH_3)_6^{3+}$ and 0.5 M $KNO_3$ at a 55 um RDM to radial and linear diffusion models; (b) is an enlargement of the region between 0.01 and 10 $Vs^{-1}$.
Figure 14B:
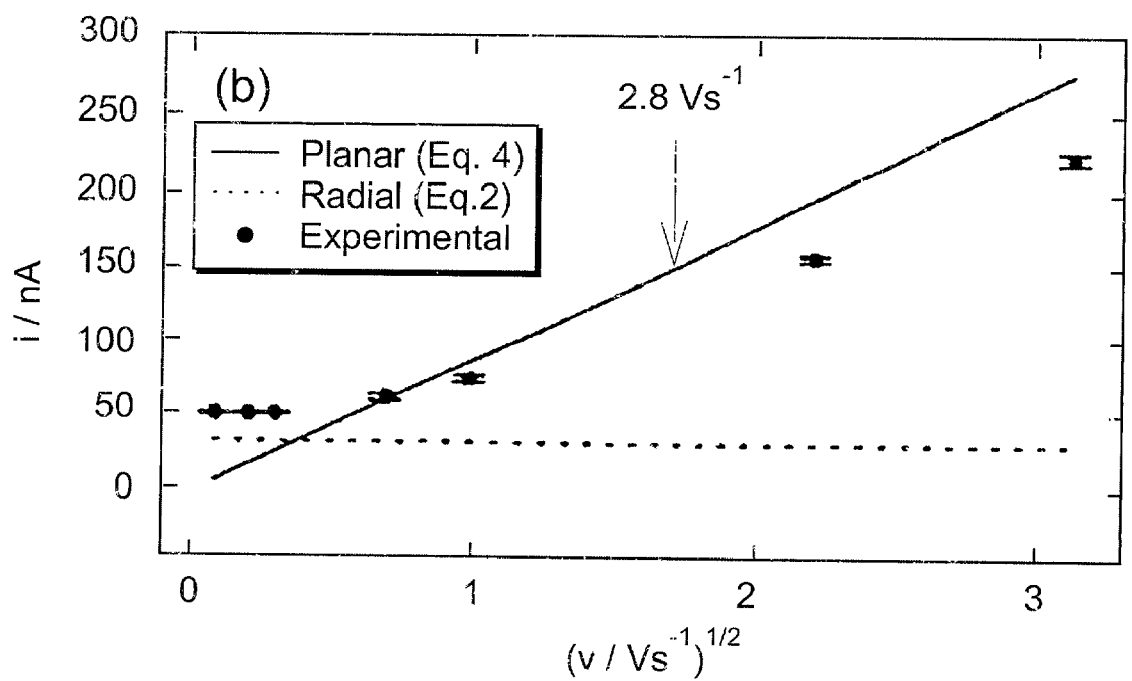
Figure 15:
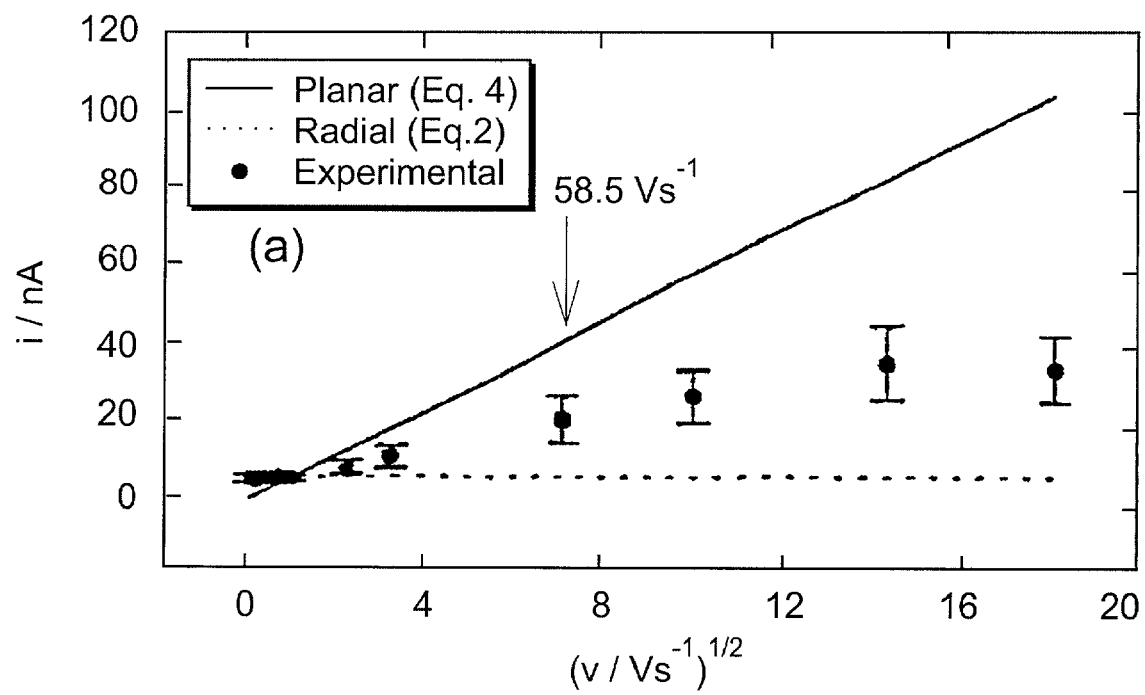
FIG. 15 shows a comparison of maximum current from CV in 5 mM $Ru(NH_3)_6^{3+}$ and 0.5 M $KNO_3$ at a 14 um RDM to radial and linear diffusion models; (b) is an enlargement of the region between 0.01 and 10 Vs $Ru^{-1}$.
Figure 15:
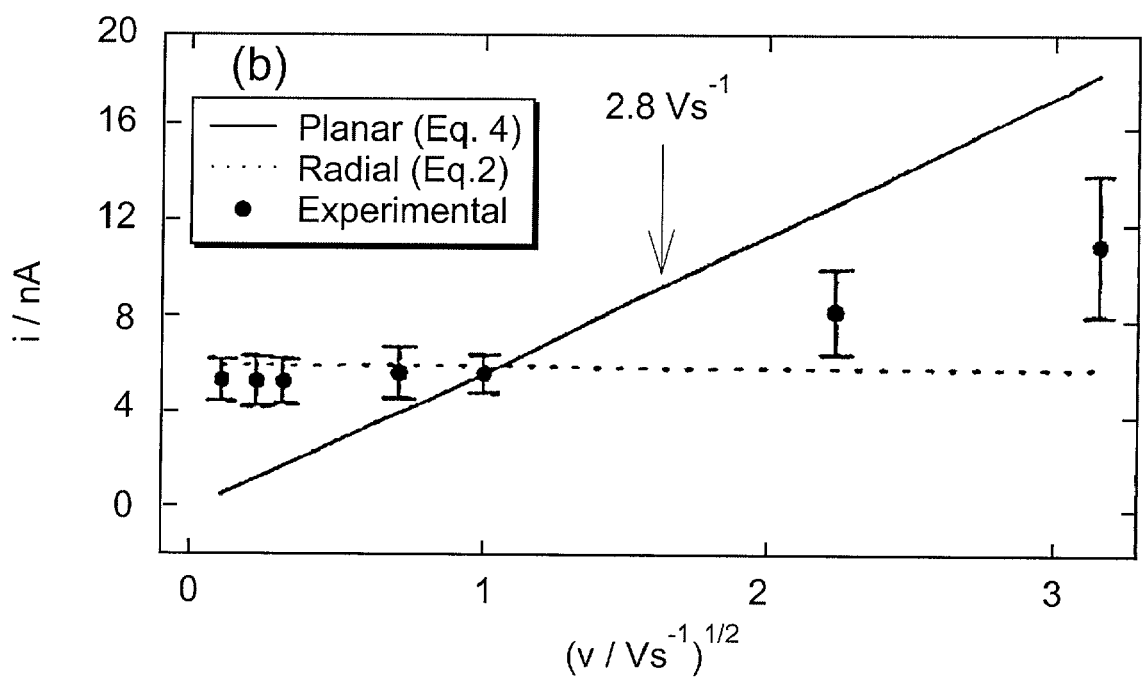

The electrochemical sensitivity to the redox probe $Fe(CN)_6^{3-}$ was investigated for monolayers (ethanol-rinsed) and hybrid bilayers. $Fe(CN)_6^{3-/4-}$ is a better redox couple than $Ag^{+/0}$ and $Pb^{2/0}$ because it stays soluble in Solution. However, $Fe(CN)_6^{3-/4-}$ is much larger and has a higher charge than the elemental ions. Thus, it is less likely to permeate through small defects in the films. FIG. 14 compares the faradaic response of $Fe(CN)_6^{3-}$ at bare and modified electrodes. At bare gold, the $Fe(CN)_6^{3-}$ gives the typical one-electron, reversible electrochemical response. Monolayer and bilayer-modified electrodes block $Fe(CN)_6^{3-}$ from reaching the surface. FIGS. 5b and 5c show expanded CV responses for modified electrodes in the absence and presence of gD, respectively. There is a small faradaic current in the bilayer film that contains gD. This could be due to permeation of $Fe(CN)_6^{3-}$ through the film and due to defects caused by the presence of gD.

Capacitance in $KNO_3$ and $Mg(NO_3)_2$ Electrolyte

Capacitance values in $KNO_3$ and $Mg(NO_3)_2$ were compared to evaluate the relative permeation of elemental mono- and dications through the films. This should be less destructive than electrochemical deposition and oxidation of $Ag^+$ and $Pb^{2+}$.

Capacitance values for clean, bare Au electrodes in 0.1 M $KNO_3$ and 0.1 M $Mg(NO_3)_2$ are 7.3.8±1.7 and 51.0±2.2 µF/cm², respectively. The capacitance for $KNO_3$ is close to that predicted by theory, 72 µF/cm², for a 1:1 electrolyte at 0.1 M. The capacitance in $Mg(NO_3)_2$ should be higher than in $KNO_3$, because there are three ions for every molecule, instead of two, and one of the ions has a +2, instead of a +1, charge. However, the Mg(NO$_3$)$_2$*6H$_2$O is hygroscopic, and thus, the actual concentration should be much lower than 0.1 M. This could yield a capacitance that is lower than expected in Mg(NO$_3$)$_2$, offsetting the contributions from increased charge and ion number. We obtained comparable capacitance values for Mg(NO$_3$)$_2$ and KNO$_3$ at annealed gold (no adhesion layer) on mica and on gold (with a Cr adhesion layer) on glass. Thus, we are certain that the electrodes and the silicon water substrates are not adding unusual capacitive behavior. Reports of typical C values for bare gold in the literature give values from about 30 μF/cm$^2$ to 100's μF/cm$^2$, which supports the values that are reported here. Capacitance is highly dependent on composition of the electrolyte, solvent, nature of the electrode surface, and applied potential. It is important to note that our capacitance values and the trends with modification are consistent and reproducible.

Whereas, the present invention has been described in relation to the drawings attached hereto, it should be understood that other and further modifications, apart from those shown or suggested herein, may be made within the spirit and scope of this invention.

What is claimed is:

1. A 3-dimensional microfabricated device, comprising:

at least one microcavity;

an Au layer surrounding said microcavity in an etched region of insulator and wherein a bottom of the device is lined with an insulator layer;

a lipid bi-layer suspended over said microcavity and said Au layer; and wherein edges of said lipid bi-layer suspended over said microcavity are anchored via inter-molecular forces to alkanethiol self assembled monolayers tethered to said Au layer.

2. The 3-dimensional microfabricated device of claim 1 having a hole in said bottom for minimizing osmotic effects.

3. The 3-dimensional microfabricated device of claim 1 having a multiple well array.

* * * * *